US011629385B2

(12) United States Patent
Salahudeen et al.

(10) Patent No.: US 11,629,385 B2
(45) Date of Patent: Apr. 18, 2023

(54) TUMOR ORGANOID CULTURE COMPOSITIONS, SYSTEMS, AND METHODS

(71) Applicant: Tempus Labs, Inc., Chicago, IL (US)

(72) Inventors: Ameen Salahudeen, Oak Park, IL (US); Verónica Sánchez Freire, Chicago, IL (US); Brandon L. Mapes, Chicago, IL (US)

(73) Assignee: Tempus Labs, Inc., Chicago, IL (US)

( * ) Notice: Subject to any disclaimer, the term of this patent is extended or adjusted under 35 U.S.C. 154(b) by 8 days.

(21) Appl. No.: 16/693,117

(22) Filed: Nov. 22, 2019

(65) Prior Publication Data

US 2021/0155989 A1    May 27, 2021

(51) Int. Cl.

| | |
|---|---|
| *C12Q 1/68* | (2018.01) |
| *C12P 19/34* | (2006.01) |
| *C12Q 1/6886* | (2018.01) |
| *C12N 5/071* | (2010.01) |
| *G16H 50/30* | (2018.01) |
| *C12M 1/32* | (2006.01) |
| *G01N 33/50* | (2006.01) |
| *G16B 20/20* | (2019.01) |
| *C12N 5/09* | (2010.01) |
| *C12Q 1/02* | (2006.01) |
| *C12Q 1/6806* | (2018.01) |
| *C12Q 1/6816* | (2018.01) |
| *C12Q 1/6844* | (2018.01) |
| *C12Q 1/6869* | (2018.01) |

(52) U.S. Cl.
CPC .......... *C12Q 1/6886* (2013.01); *C12M 23/12* (2013.01); *C12N 5/0691* (2013.01); *C12N 5/0693* (2013.01); *C12Q 1/025* (2013.01); *C12Q 1/6806* (2013.01); *C12Q 1/6816* (2013.01); *G01N 33/5091* (2013.01); *G16B 20/20* (2019.02); *G16H 50/30* (2018.01); *C12N 2500/25* (2013.01); *C12N 2501/11* (2013.01); *C12N 2501/117* (2013.01); *C12N 2501/119* (2013.01); *C12N 2501/33* (2013.01); *C12N 2501/998* (2013.01); *C12N 2501/999* (2013.01); *C12N 2509/10* (2013.01); *C12N 2521/10* (2013.01); *C12N 2527/00* (2013.01); *C12N 2533/52* (2013.01); *C12N 2533/54* (2013.01); *C12N 2533/90* (2013.01); *C12Q 1/6844* (2013.01); *C12Q 1/6869* (2013.01)

(58) Field of Classification Search
CPC ............ C12N 2513/00; C12N 2503/02; C12N 2503/04; C12N 5/0671; C12N 5/0677
See application file for complete search history.

(56) References Cited

U.S. PATENT DOCUMENTS

2015/0329829 A1    11/2015 Shen et al.

FOREIGN PATENT DOCUMENTS

| | | |
|---|---|---|
| EP | 2 412 800 A1 | 2/2012 |
| EP | 2 743 345 A1 | 6/2014 |
| WO | WO 2009/022907 A2 | 2/2009 |
| WO | WO 2010/090513 A2 | 8/2010 |
| WO | WO 2012/014076 A2 | 2/2012 |
| WO | WO 2012/168930 A2 | 12/2012 |
| WO | WO 2013/093812 A2 | 6/2013 |
| WO | WO 2014/159356 A1 | 10/2014 |
| WO | WO 2015/173425 A1 | 11/2015 |
| WO | WO 2016/083612 A1 | 6/2016 |
| WO | WO 2016/083613 A2 | 6/2016 |
| WO | WO 2017/149025 A1 | 9/2017 |
| WO | WO 2017/220586 A1 | 12/2017 |

OTHER PUBLICATIONS

Li, X. et al. "Organoid cultures recapitulate esophageal adenocarcinoma heterogeneity providing a model for clonality studies and precision therapeutics" Nature Communications, (2018) 9:2983, pp. 1-13 (Year: 2018).*
Supplementary Materials for "Patient-derived organoids model treatment response of metastatic gastrointestinal cancers" (published Feb. 23, 2018, Science 359, 920) from https://science.sciencemag.org/content/suppl/2018/02/21/359.6378.920.DC1 47 pages printed (Year: 2018).*
Yancovitz, M. et al. "Intra- and Inter-Tumor Heterogeneity of BRAFV600E Mutations in Primary and Metastatic Melanoma" PLoS ONE, Jan., 2012, vol. 7, issue 1 (Year: 2012).*
Ou, S.-H. I. et al. "Liquid Biopsy to Identify Actionable Genomic Alterations" American Society of Clinical Oncology Educational Book 38 (May 23, 2018) 978-997 (Year: 2018).*
Bronkhorst, A. J. et al. "Characterization of the cell-free DNA released by cultured cancer cells", Biochimica et Biophysica Acta 1863 (2016) 157-165 (Year: 2016).*
Supplementary Information for Li, X. et a, Nature Communications vol. 9, Article No. 2983 (Jul. 30, 2018), online at https://www.nature.com/articles/s41467-018-05190-9#Sec26, 11 printed pages. (Year: 2018).*
Nam, M.-O. et al. "Effects of a small molecule R-spondin-1 substitute RS-246204 on a mouse intestinal organoid culture" Oncotarget, 2018, vol. 9, (No. 5), pp. 6356-6368 (Published: Dec. 26, 2017). (Year: 2017).*
Matsumoto, N. et al. "C3a Enhances the Formation of Intestinal Organoids through C3aR1" Front Immunol. Sep. 4, 2017;8:1046. (Year: 2017).*

(Continued)

*Primary Examiner* — Stephen T Kapushoc
(74) *Attorney, Agent, or Firm* — Morgan, Lewis & Bockius LLP

(57) ABSTRACT

Provided herein are novel organoid culture media, organoid culture systems, and methods of culturing tumor organoids using the subject organoid culture media. Also provided herein are tumor organoids developed using such organoid culture systems, methods for assessing the clonal diversity of the tumor organoids, and methods for using such tumor organoids, for example, for tumor modelling and drug development applications. In particular embodiments, the tumor organoid culture media provided herein is substantially free of R-spondins (e.g., R-spondin1).

20 Claims, 21 Drawing Sheets

(56) References Cited

OTHER PUBLICATIONS

M. Kim, et al., "Patient-derived lung cancer organoids as in vitro cancer models for therapeutic screening" Nature Communications vol. 10, Article No. 3991 (2019), Published: Sep. 5, 2019. (Year: 2019).*
Eke et al. "Radiobiology goes 3D: How ECM and cell morphology impact on cell survival after irradiation", Radiotherapy and Oncology, vol. 99, pp. 271-278 (2011).
Breslin et al. "Three-dimensional cell culture: the missing link in drug discovery", Drug Discovery Today, vol. 18, Nos. 5/6 (2013).
Driehuis et al. "Oral Mucosal Organoids as a Potential Platform for Personalized Cancer Therapy", Cancer Discovery, vol. 9, pp. 852-871 (2019).
Tuveson et al. "Cancer modeling meets human organoid technology", Science, vol. 364, pp. 952-955 (2019).
Eder et al. :3D Hanging Drop Culture to Establish Prostate Cancer Organoids, 3D Cell Culture: Methods and Protocols, Methods in Molecular Biology, vol. 1612, pp. 167-175, Year: 2017.
Andor et al. "Pan-cancer analysis of the extent and consequences of intra-tumor heterogeneity", Nat Med., vol. 22, pp. 105-113 (2016).
Bein et al. "Microfluidic Organ-on-a-Chip models of Human Intestine", Cellular and Molecular Gastroenterology and Heptatology, vol. 5, No. 4, pp. 659-668 (2018).
Ben-David et al. "Genetic and Trascriptional evolution alters cancer cell line drug response", Nature, vol. 560, pp. 325-330 (2018).
Boj et al. "Organoid Models of Human and Mouse Ductal Pancreatic Cancer", Cell, vol. 160, pp. 324-338 (2015).
Bozic et al. "Timing and heterogeneity of mutations associated with drug resistance in metastic cancers" PNAS, vol. 111, No. 45, pp. 15964-15968 (2014).
Brayer et al. "Recurrent Fusions in MYB and MYBL1 Define a Common, Transcription Factor-Driven Oncogenic Pathway in Salivary Gland Adenoid Cystic Carcinoma" Cancer Discov., vol. 6, pp. 176-187 (2016).
Broutier et al. "Human Primary Liver Cancer-derived Organoid Cultures for disease modelling and drug screening" Nat. Med., vol. 23, pp. 1424-1435 (2017).
Pflug et al. "TRUmiCount: correctly counting absolute numbers of molecules using unique molecular identifiers", Bioinformatics, vol. 24, pp. 3137-3144 (2018).
Chomczynski et al. "The single-step method of RNA isolation by acid guanidinium thiocyanate-phenol-chloroform extraction: twenty-something years on", Nature Protocols, vol. 1, No. 2, pp. 581-585 (2006).
Chowell et al. "When (distant) relatives stay too long: implications for cancer medicine", Genome Biology, vol. 17, pp. 1-3 (2016).
Rio et al. "Enrichment of Poly(A) mRNA Using Immobilized Oligo(dT)", Cold Spring Harbor Laboratory Press, vol. 2010, Issue 7, pp. 1-3 (2010).
Mootha et al. "PGC-1α-responsive genes involved in oxidative phosphorylation are coordinately downregulated in human diabetes", Nature genetics, vol. 34, pp. 267-273 (2003).
Burgess et al. "RNA extraction from self-assembling peptide hydrogels to allow qPCR analysis of encapsulated cells" PLOS ONE, pp. 1-19, (2018).
De Lau et al. "The R-spondin protein family", Genome Biology, vol. 13, pp. 1-10 (2012).
Ozsolak et al. "Direct RNA sequencing", Nature, vol. 461, pp. 814-818 (2009).
Finotello et al. "Measuring differential gene expression with RNA-seq: challenges and strategies for data analysis", Briefings in Functional Genomics, vol. 14, pp. 130-142 (2014).
Ganesh et al. "A rectal cancer organoid platform to study individual responses to chemoradiation", Nature Medicine, Year: 2019.
Gao et al. "Organoid cultures derived from patients with advanced prostate cancer", Cell, vol. 159, pp. 176-187 (2014).
Goodspeed et al. "Tumor-Derived Cell Lines as Molecular Models of Cancer Pharmacogenomics", Mol. Cancer. Res., vol. 14, pp. 3-13 (2016).
Gramont et al. "Novel TGF-β inhibitors ready for prime time in onco-immunology", Oncoimmunology, vol. 6, pp. e1257453 (2017).
Jabs et al. "Screening drug effects in patient-derived cancer cells links organoid responses to genome alterations", Mol. Systems Biology, vol. 13, pp. 1-16 (2017).
Kivioja et al. "Counting absolute numbers of molecules using unique molecular identifiers", Nature Methods, vol. 9, No. 1, pp. 72-74 (2012).
Landau et al. "Evolution and impact of subclonal mutations in chronic lymphocytic leukemia", Cell, vol. 152, pp. 714-726 (2013).
Lee et al. "Tumor evolution and drug response in patient-derived organoid models of bladder cancer", Cell, vol. 173, pp. 515-528 (2018).
Lin et al. "mRNA/cDNA Library Construction Using RNA-Polymerase Cycling Reaction", Methods in Molecular Biology, vol. 221, pp. 129-143, Year: 2003.
Liu et al. "The Cross-contaminated Cell Lines of Adenoid Cystic Carcinoma: A Crucial Concern", Translational Surgery, vol. 2, pp. 10-13 (2017).
Maley et al. "Genetic clonal diversity predicts progression to esophageal adenocarcinoma", Nature Genetics, vol. 38, pp. 468-473 (2006).
McConnell et al. "Construction of a representative cDNA library from mRNA isolated from mouse oocytes", FEBS, vol. 195, pp. 199-202 (1986.
McCune and Grace "Distance Measures", Chapter 6, pp. 45-57 (2002).
Yan et al. "A Comprehensive Human Gastric Cancer Organoid Biobank Captures Tumor Subtype Heterogeneity and Enables Therapeutic Screening", Cell Stem Cell, vol. 23, pp. 882-897 (2018).
Nagalakshmi et al. "The Transcriptional Landscape of the Yeast Genome Defined by RNA Sequencing", Science, vol. 320, pp. 1344-1349 (2008).
Nagle et al. "Patient-derived tumor organoids for prediction of cancer treatment response", Seminars in Cancer Biology, vol. 15, pp. 258-264 (2018).
Shendure et al. "Next-generation DNA sequencing", Nature Biotechnology, vol. 26, pp. 1135-1145 (2008).
Niederst et al. "Bypass Mechanisms of Resistance to Receptor Tyrosine Kinase Inhibition in Lung Cancer", Sci Signal, vol. 6, pp. 1-12 (2014).
Garalde et al. "Highly parallel direct RNA sequencing on an array of nanopores", Nature Methods, vol. 15, pp. Year: 2018.
Oh et al. "An improved method for constructing a full-length enriched cDNA library using small amounts of total RNA as a starting material", Experimental and Molecular Medicine, vol. 35, pp. 586-590 (2003).
Ooft et al. "Patient-derived organoids can predict response to chemotherapy in metastatic colorectal cancer patients", Science Translational Medicine, vol. 11, pp. 1-9 (2019).
Pereira et al. "The somatic mutation profiles of 2,433 breast cancers refines their genomic and transcriptomic landscapes", Nature Communications, vol. 7, pp. 1-15 (2016).
Poeckh et al. "Adsorption and elution characteristics of nucleic acids on silica surfaces and their use in designing a miniaturized purification unit", Anal. Biochem., vol. 15, pp. 253-262 (2008).
Puca et al. "Patient derived organoids to model rare prostate cancer phenotypes", Nature Communications, vol. 9, pp. 1-10 (2018).
Duda et al. "Pattern Classification", Second Edition, 738 pages, Year: 2001.
Drost et al. "Organoids in cancer research", Nature Reviews, vol. 18, pp. 407-418 (2018).
Sachs et al. "A Living Biobank of Breast Cancer Organoids Captures Disease Heterogeneity", Cell, vol. 172, pp. 373-386 (2018).
Fuji et al. "A Colorectal Tumor Organoid Library Demonstrates Progressive Loss of Niche Factor Requirements during Tumorigenesis", Cell Stem Cell, vol. 18, pp. 827-838 (2016).
Serrati et al. "Next-generation sequencing: advances and applications in cancer diagnosis". OncoTargets and Therapy, vol. 9, pp. 7355-7365 (2016).
Subramanian et al. "Gene set enrichment analysis: A knowledge-based approach for interpreting genome-wide expression profiles", PNAS, vol. 102, No. 43, pp. 15545-15550 (2005).

(56) References Cited

OTHER PUBLICATIONS

Islam et al. "Quantitative single-cell RNA-seq with unique molecular identifiers", Nature Methods, vol. 11, No. 2, pp. 163-166 (2014).
Urbischek et al. "Organoid culture media formulated with growth factors of defined cellular activity", Scientific Reports, vol. 9, pp. 1-11 (2019).
Van De Wetering et al. "Prospective derivation of a Living Organoid Biobank of colorectal cancer patients", Cell, vol. 161, pp. 933-945 (2015).
Vlachogiannis et al. "Patient-derived organoids model treatment response of metastatic gastrointestinal cancers", Science, vol. 359, pp. 920-926 (2018).
Wang et al. "RNA-Seq: a revolutionary tool for transcriptomics", Nat Rev Genet., vol. 10, pp. 57-63 (2009).
Xu et al. "Organoid technology and applications in cancer research", Journal of Hematology & Oncology, vol. 11, pp. 1-15 (2018).
Yao et al. "Patient-Derived Organoids Predict Chemoradiation Responses of Locally Advanced Rectal Cancer", Cell Press, vol. 26, pp. 1-10 (2020).
Zhang et al. "Intra-tumor Heterogeneity in Localized Lung Adenocarcinomas Delineated by Multi-region Sequencing", Science, vol. 346, pp. 256-259 (2014).
Korenchuk et al. "VCaP, A Cell-Based Model System of Human Prostate Cancer", In Vivo, vol. 15, pp. 163-168 (2001).
Cardea's Tech+Bio Infrastructure, Cardea Bio | Graphene-based, Biology-gated Transistor Technology, https://cardeabio.com/technology/, 4 pages.
Ashford, Molika, "Harvard Team Advancing Algorithmic Signature to Improve PARP Inhibitor Patient Selection", genomeweb, Apr. 18, 2019, 3 pages.
Brenan, Lisa, et al. "Phenotypic characterization of a comprehensive set of MAPK1/ERK2 missense mutants", Cell Rep., Oct. 18, 2016, 23 pages.
Dijkstra, Krijn K., et al. "Generation of Tumor-Reactive T Cells by Co-culture of Peripheral Blood Lymphocytes and Tumor Organoids", CellPress, Sep. 6, 2018, Cell 174, pp. 1586-1598.
Findlay, Gregory M., et al. "Saturation Editing of Genomic Regions by Multiplex Homology-Directed Repair", Nature, Sep. 4, 2014, 24 pages.
Findlay, Gregory M., et al. "Accurate classification of BRCA1 variants with saturation genome editing", Nature, Oct. 2018, 32 pages.
Giacomelli, Andrew O., et al. "Mutational processes shape the landscape of TP53 mutations in human cancer", Nat Genet, Oct. 2018, 20 pages.
Gulhan, Doga C., et al. "Detecting the mutational signature of homologous recombination deficiency in clinical samples", Technical Report, Nature Genetics, vol. 51, May 2019, pp. 912-919.
Jenkins, et al. "Ex Vivo Profiling of PD-1 Blockade Using Organotypic Tumor Spheroids", Cancer Discov., Feb. 2018, 36 pages.
Kohsaka, Shinji, et al. "A method of high-throughput functional evaluation of EGFR gene variants of unknown significance in cancer", Science Translational Medicine | Research Resource, Med. 9, Nov. 15, 2017, 12 pages.
Matreyek, Kenneth A., et al. "Multiplex Assessment of Protein Variant Abundance by Massively Parallel Sequencing", Nat Genet., Jun. 2018, 27 pages.
Mighell, Taylor L., et al. "A Saturation Mutagenesis Approach to Understanding PTEN Lipid Phosphatase Activity and Genotype-Phenotype Relationships", The American Journal of Human Genetics 102, May 3, 2018, pp. 943-955.
Sato, Toshiro, et al. "Single Lgr5 stem cells build crypt—villus structures in vitro without a mesenchymal niche", Nature, vol. 459, May 14, 2009, pp. 262-265.
Sato, Toshiro, et al. "Long-term Expansion of Epithelial Organoids From Human Colon, Adenoma, Adenocarcinoma, and Barrett's Epithelium", Gastroenterology, vol. 141, No. 5, Nov. 2011, pp. 1762-1772.
Neal, James T., et al. "Organoid Modeling of the Tumor Immune Microenvironment", Cell 175, 2018, pp. 1972-1988.
Fujii, et al. "A Colorectal Tumor Organoid Library Demonstrates Progressive Loss of Niche Factor Requirements During Tumorigenesis", Cell Stem Cell 18, 827-838, Jun. 2, 2016.

* cited by examiner

TUMOR ORGANOID CULTURE COMPOSITIONS, SYSTEMS, AND METHODS

TECHNICAL FIELD

The present disclosure relates generally to methods of culturing tumor organoid, methods for assessing clonal diversity in such tumor organoids, and methods for using the cultured tumor organoids to inform cancer treatment.

BACKGROUND

The development of effective cancer treatment regimens continues to remain a major hurdle in cancer research. While traditional cancer models such as traditional two-dimensional (2D) cell line cultures and patient-derived tumor xenografts (PDTXs) have made tremendous contributions in cancer research, these models are limited for clinical research and drug development. Such models oftentimes poorly recapitulate the original tumor source and cannot accurately predict treatment responses in vivo. For example, 2D culture models lack many crucial signaling factors, such as cell-cell and cell-matrix interactions that contribute to essential cellular functions in proliferation, differentiation and survival. Beslin and O'Driscoll, *Drug Discov. Today* 18:240-249 (2013); and Eke and Cordes, *Radiother. Oncol.* 99 271-278 (2011). Two-dimensional (2D) culture models are also generally derived from single clones and, therefore, do not recapitulate the complete diversity of tumors, which often consists of many different cell types. Goodspeed et al., *Mol. Cancer Res.* 14:3-131 (2016). Moreover, the genetic composition and cell behavior of monolayer cell lines change over time. Therefore, the 2D cultures cannot cover the full genetic spectrum of tumor types, resulting in misrepresentation of the original tumor and non-physiological responses. Ben-David et al., *Nature* 560:325-30 (2018); Korenchuk et al., *In Vivo* 15:163-168 (2001): and van de Wetering et al., *Cell* 161: 933-945 (2015). PDTXs are utilized widely for drug discovery, biomarker detection and preclinical drug evaluation in cancer research. However, the transplantation success rate for PDTXs is relatively low, while resource requirements and costs for producing such PDTXs are relatively high. Nagle et al., *Seminars in Cancer Biology* 53:258-264 (2018). Further, mouse biology and physiology can alter the genetic composition of the xenograft. Ben-David et al., *Nat Genet* 49:1567-1575 (2017). Thus PDTXs model often times fail to recapitulate source tumors.

Tumor organoids (TOs) are three dimensional cultures of cancerous cells derived from tumor tissues and are similar to the original cancer source in terms of genome and function. Tumor organoids can imitate the pathological characteristics of primary tissue at the organ level and better simulate the tumor in vivo as compared to traditional models. Further, tumor organoid inheritance and morphology remain stable after many generations. Thus, tumor organoids potentially provide a powerful tool in cancer research and personalized treatment. Such tumor organoid systems can be used, for example, for drug discovery and clinical treatment response studies, as well as for disease modelling and development studies. Tumor organoid models have been developed for several different types of cancers including stomach cancer (Vlachogiannis et al., *Science* 359: 920-6 (2018)), intestinal cancer (Vlachogiannis et al., *Science* 359: 920-6 (2018)), liver cancer (Broutier et al., *Nat. Med.* 23:1424-34 (2017)), pancreatic cancer (Boj et al., *Cell* 160: 324-38 (2015)), breast cancer (Sachs et al., *Cell* 172:373-86 (2018)), bladder cancer (Lee et al., *Cell* 173:515-28 (2018)), prostate cancer (Gao et al., *Cell.* 159:176-187 (2014); and Puca et al., *Nat. Commun.* 9:2404 (2018)), and head and neck cancer (Driehuis et al., *Cancer Discovery* 9:852-871 (2019)).

A critical component of the development of tumor organoids is the formulation of organoid culture media that contain essential growth factors. Growth factors used in such media, generally include R-spondins (e.g., R-spondin1), which potentiate Wnt pathway activity in epithelial cells. The production of growth factors, including R-spondins, typically relies on the use of eukaryotic expression systems to ensure correct disulphide bond formation and macromolecular folding. In eukaryotic expression systems, growth factors are typically secreted into the cell culture media from the expression hosts, and the conditioned media containing the growth factor (e.g., R-spondin) is then diluted directly into the organoid culture media. R-spondin expressing cell lines, however, are not widely available and the use of conditioned media presents the problems of batch-to-batch variation of growth factor activity. Commercially available purified growth factors can also be used to supplement organoid culture media. These purified growth factors, however, are expensive for medium to large scale applications, such as genetic and chemical library screening or clinical biobanking. Moreover, culturing tumor organoids typically requires using different culture media for different tumor organoid types, and each culture medium generally contains a multitude of different growth factors. See Tuveson and Clevers *Science* 364:952-955 (2019). Drost and Clevers. *Nature Reviews Cancer* 18:407-418 (2018); Xu et al., Journal of Hematology & *Oncology* 11:116 (2018).

In cancers, somatic variants accumulate in different populations of cells during clonal expansion over the course of disease, thereby creating a mixture of cancer cell clones in the tumor with genetic and morphological heterogeneity. Tumor clonal diversity can arise due to random mutations that occur during cell divisions of cancer cells or through mutational events stimulated by various exposures.

While a few clones may dominate the composition of a tumor, minor subclones can determine the clinical course of disease progression and recurrence. See, e.g., Landau et al., *Cell* 152(4):714-726 (2013); Maley et al., *Nat Genet.* 38:468-73 (2006): Chowell et al., *Genome Biol.* 17:1-4 (2016); and Bozic et al., *Proc Natl Acad Sci USA* 111: 15964-8 (2014). Several studies have shown that there is a clear association between a greater number of detectable subclonal populations and poorer clinical outcome in lower grade glioma, and cancers of the prostate, kidney, head and neck, breast, and lung. See, e.g., Zhang et al., *Science* 346:256-9 (2014); Andor et al., *Nat Med.* 22:105-113 (2015); and Pereira et al., *Nat Commun.* 7:11479 (2016).

Clonal heterogeneity contributes to drug resistance; anticancer treatments can act as a strong selective pressure and drive the emergence of drug-resistant subclones that allow the tumor to persist. For example, several studies of cancer patients who have lapsed, revealed that tumor cells in the relapsed-associated clone were often present as undetected subclones in the primary tumor before the initiation of therapy, suggesting that driver mutations in these subclonal populations are selected for during therapy. Therefore, a tumor organoid that recapitulates the clonal diversity of its source tumor advantageously provides a powerful tool for the development of anti-cancer therapies and personalized treatment regimens.

Thus, there remains need for improved reagents for culturing tumor organoids, tumor organoid lines for additional cancers that can be used for cancer research, and methods to validate whether the tumor organoid faithfully recapitulates the features of the patient's original source tumor.

SUMMARY

Provided herein are novel organoid culture media, organoid culture systems, and methods of culturing tumor organoids using the subject organoid culture media. Also provided herein are tumor organoids developed using such organoid culture systems, methods for assessing the clonal diversity of such tumor organoids, and methods for using such tumor organoids, for example, for tumor modelling and drug development applications. The tumor organoid culture media provided herein can be advantageously used to culture more than one type of tumor organoid and require fewer growth factors as compared to traditional organoid culture media. In some embodiments, the tumor organoid culture media provided herein is substantially free of R-spondins (e.g., R-spondin1). As such, in some embodiments, the subject organoid growth media reduce problems associated with traditional organoid culture media including, for example, growth factor production, variability in activity, component costs, large-scale use, and the masking of cancer therapeutic vulnerabilities in vitro due to the inappropriate presence of redundant growth factors enabling non-physiologic bypass survival mechanisms. See, e.g., Niederst and Engelman, *Science Signaling* 6(294): re6 (2013). In some embodiments, the subject organoid culture medium support the growth and development of tumor organoids that exhibit similar clonal diversity to the source cancer from which the tumor organoid is derived. Thus, in some embodiments, the subject tumor organoid provided herein recapitulates the clonal diversity of its source tumor. Such a tumor organoid provides a useful model for the development of anti-cancer therapies and personalized treatment regimens.

In a first aspect, provided herein is a method for culturing a tumor organoid. The method includes the steps of: a. obtaining a tumor tissue from a source cancer; b. dissociating the tumor tissue into a plurality of dissociated tumor cells; and c. culturing the dissociated tumor cells in an organoid culture system comprising an organoid culture medium, thereby forming the tumor organoid. In exemplary embodiments, the organoid culture medium is substantially free of R-spondins. In some embodiments, the method further includes the step of: d. measuring the tumor cell heterogeneity of the tumor organoid. In several embodiments, the method also includes the step of: e. comparing the tumor cell heterogeneity of the tumor organoid with the tumor cell heterogeneity of the source cancer. In some embodiments, the source cancer is an anal cancer, a basal cell skin cancer, a squamous cancer, a breast cancer, a bladder cancer, a cervical cancer, a colon cancer, an endometrial cancer, a head and neck cancer, a hepatobiliary cancer, a kidney cancer, a gastric cancer, a lung cancer, a mesothelial cancer of the pleural cavity, a mesothelial cancer of the peritoneal cavity, an ovarian cancer, prostate cancer, or a rectal cancer.

In another aspect, provided herein is a method for culturing a tumor organoid. In some embodiments, the method includes the following steps: a. obtaining a tumor tissue; b. dissociating the tumor tissue into a plurality of dissociated tumor cells; and c. culturing the dissociated tumor cells in an organoid culture system that includes an organoid culture medium, thereby forming the tumor organoid. In particular embodiments, the organoid culture media includes a plurality of organoid growth factors, wherein the plurality of organoid growth factors includes: i) Noggin, ii) a combination of EGF, and Noggin, or iii) a combination of EGF, Noggin, FGF7 and FGF10, and where the organoid culture medium is substantially free of R-spodin. In some embodiments, the method further includes the step of: d. measuring the tumor cell heterogeneity of the tumor organoid. In several embodiments, the method also includes the step of: e. comparing the tumor cell heterogeneity of the tumor organoid with the tumor cell heterogeneity of the source cancer. In some embodiments, the source cancer is an anal cancer, a basal cell skin cancer, a squamous cancer, a breast cancer, a bladder cancer, a cervical cancer, a colon cancer, an endometrial cancer, a head and neck cancer, a hepatobiliary cancer, a kidney cancer, a gastric cancer, a lung cancer, a mesothelial cancer of the pleural cavity, a mesothelial cancer of the peritoneal cavity, an ovarian cancer, prostate cancer, or a rectal cancer.

In certain embodiments, the organoid culture media further includes one or more molecular inhibitors that include a Rho kinase inhibitor, a transforming growth factor-beta inhibitor, a MAP kinase inhibitor or combinations thereof.

In some embodiments, the one or more molecular inhibitors includes the Rho kinase inhibitor, and wherein the Rho kinase inhibitor is Y27632. In certain embodiments, the one or more molecular inhibitors includes the transforming growth factor-beta inhibitor, and the transforming growth factor-beta inhibitor is A-83-01.

In exemplary embodiments, the one or more molecular inhibitors includes the MAP kinase inhibitor, and the MAP kinase inhibitor is a P38 inhibitor. In particular embodiments, the P38 inhibitor is SB202190.

In some embodiments, the one or more molecular inhibitors includes the Rho kinase inhibitor Y27632, the transforming growth factor-beta inhibitor A-83-01, and the MAP kinase inhibitor SB202190.

In one aspect, provided herein is a method for culturing a tumor organoid. The method includes the steps of: a. obtaining a tumor tissue from a source cancer; b. dissociating the tumor tissue into a plurality of dissociated tumor cells; and c. culturing the dissociated tumor cells in an organoid culture system that includes an organoid culture medium, thereby forming the tumor organoid. In some embodiments, the organoid culture media includes a plurality of growth factors, wherein the plurality of growth factors is: i) Noggin, ii) a combination of EGF and Noggin, or iii) a combination of EGF, Noggin, FGF7 and FGF10.

In some embodiments, the method further includes the step of: d. measuring the tumor cell heterogeneity of the tumor organoid. In several embodiments, the method also includes the step of: e. comparing the tumor cell heterogeneity of the tumor organoid with the tumor cell heterogeneity of the source cancer. In some embodiments, the source cancer is an anal cancer, a basal cell skin cancer, a squamous cancer, a breast cancer, a bladder cancer, a cervical cancer, a colon cancer, an endometrial cancer, a head and neck cancer, a hepatobiliary cancer, a kidney cancer, a gastric cancer, a lung cancer, a mesothelial cancer of the pleural cavity, a mesothelial cancer of the peritoneal cavity, an ovarian cancer, prostate cancer, or a rectal cancer.

In certain embodiments, the organoid culture media further includes one or more molecular inhibitors that include a Rho kinase inhibitor, a transforming growth factor-beta inhibitor, a MAP kinase inhibitor or combinations thereof.

In some embodiments, the one or more molecular inhibitors includes the Rho kinase inhibitor, and wherein the Rho kinase inhibitor is Y27632. In certain embodiments, the one or more molecular inhibitors includes the transforming growth factor-beta inhibitor, and the transforming growth factor-beta inhibitor is A-83-01. In exemplary embodiments, the one or more molecular inhibitors includes the MAP kinase inhibitor, and the MAP kinase inhibitor is a P38 inhibitor. In particular embodiments, the P38 inhibitor is SB202190.

In some embodiments, the one or more molecular inhibitors includes the Rho kinase inhibitor Y27632, the transforming growth factor-beta inhibitor A-83-01, and the MAP kinase inhibitor SB202190.

In some embodiments, of the culturing methods provided herein, the organoid culture media further includes: a) a chemically-defined, minimal culture medium; b) L-glutamine; c) a serum replacement supplement; d) N-acetyl-L-cysteine; and e) nicotinamide. In particular embodiments, the chemically-defined, minimal culture medium is Dulbecco's Modified Eagle Medium, Roswell Park Memorial Institute 1640 Medium, Ham's F-12 Medium, or a combination thereof.

In exemplary embodiments, the serum replacement supplement includes holo-transferrin, insulin, superoxide dismutase, catalase enzyme, carnitine, putrescine, glutathione, galactose, corticosterone, ethanolamine, linoleic acid, linolenic acid, selenite, tri-iodothyronine, tocopherol, and progesterone. In other embodiments, the serum replacement supplement comprises insulin and holo-transferrin.

In several embodiments, the organoid culture media further includes an antibiotic. In some embodiments, the antibiotic is penicillin streptomycin.

In some embodiments, the plurality of organoid growth factors include EGF, and Noggin and the cancer source is squamous cancer, lung cancer, colon cancer, gastric cancer, esophageal cancer, head and neck cancer, or colon cancer.

In several embodiments, the plurality of organoid growth factors include EGF, Noggin, FGF7, and FGF10 and the cancer source is a breast cancer, lung cancer, gastric cancer, colon cancer, esophageal, or liver cancer.

In particular embodiments, the organoid culture system further includes an extracellular matrix substitute. In some embodiments, the extracellular matrix substitute includes one or more recombinant proteins selected from collagen, laminin, fibronectin and gelatin. In certain embodiments, extracellular matrix substitute comprises one or more basement membrane extracts.

In several embodiments, the culturing is performed in a hang drop system. In particular embodiments, the culturing is performed on an artificial scaffold. In exemplary embodiments, the artificial scaffold is a microbead or a microwell. In some embodiments, the culturing is performed in an emulsion droplet using a microfluidic system.

In some embodiments of the culturing methods provided herein, the method further includes subculturing the tumor organoid following the culturing. In certain embodiments, the method includes cryopreserving the tumor organoid following the culturing.

In another aspect, provided herein are organoid culture media for culturing tumor organoids. In exemplary embodiments, the organoid culture media are free of R-spondins.

In some embodiments, the organoid culture medium includes a plurality of organoid growth factors, wherein the plurality of organoid growth factors includes: a) Noggin, b) a combination of EGF, and Noggin, or c) a combination of EGF, Noggin, FGF7 and FGF10, and wherein the organoid culture medium is substantially free of R-spondins.

In some embodiments, the organoid culture medium includes a plurality of organoid growth factors, wherein the plurality of organoid growth factors is: a) Noggin, b) a combination of EGF, and Noggin, or c) a combination of EGF, Noggin, FGF7 and FGF10, and wherein the organoid culture medium is substantially free of R-spondins.

In certain embodiments, the organoid culture media further includes one or more molecular inhibitors that include a Rho kinase inhibitor, a transforming growth factor-beta inhibitor, a MAP kinase inhibitor or combinations thereof.

In some embodiments, the one or more molecular inhibitors includes the Rho kinase inhibitor, and wherein the Rho kinase inhibitor is Y27632. In certain embodiments, the one or more molecular inhibitors includes the transforming growth factor-beta inhibitor, and the transforming growth factor-beta inhibitor is A-83-01. In exemplary embodiments, the one or more molecular inhibitors includes the MAP kinase inhibitor, and the MAP kinase inhibitor is a P38 inhibitor. In particular embodiments, the P38 inhibitor is SB202190.

In some embodiments, the one or more molecular inhibitors includes the Rho kinase inhibitor Y27632, the transforming growth factor-beta inhibitor A-83-01, and the MAP kinase inhibitor SB202190.

In some embodiments, of the culturing methods provided herein, the organoid culture media further includes: a) a chemically-defined, minimal culture medium; b) L-glutamine; c) a serum replacement supplement; d) N-acetyl-L-cysteine; and e) nicotinamide. In particular embodiments, the chemically-defined, minimal culture medium is Dulbecco's Modified Eagle Medium, Roswell Park Memorial Institute 1640 Medium, Ham's F-12 Medium, or a combination thereof.

In exemplary embodiments, the serum replacement supplement includes holo-transferrin, insulin, superoxide dismutase, catalase enzyme, carnitine, putrescine, glutathione, galactose, corticosterone, ethanolamine, linoleic acid, linolenic acid, selenite, tri-iodothyronine, tocopherol, and progesterone. In other embodiments, the serum replacement supplement comprises insulin and holo-transferrin.

In several embodiments, the organoid culture media further includes an antibiotic. In some embodiments, the antibiotic is penicillin streptomycin.

In another aspect, provided herein are three dimensional tumor organoids and tumor organoid compositions that include a plurality of cells derived from an adenoid cystic carcinoma (ACC).

In some embodiments, the three dimensional tumor organoid includes cells derived from an adenoid cystic carcinoma (ACC). The tumor organoid includes a plurality of heterogeneous cells and has similar clonal diversity as compared to the adenoid cystic carcinoma. In some embodiments, the tumor organoid exhibits similar histologic architecture as compared to the ACC.

In certain embodiments, the composition includes: i) a three dimensional tumor organoid comprising cells derived from an adenoid cystic carcinoma (ACC), wherein the tumor organoid comprise an NFIB-MYBL1 fusion; and ii) an extracellular matrix component. The tumor organoid includes a plurality of heterogeneous cells and has similar clonal diversity as compared to the adenoid cystic carcinoma. In some embodiments, the tumor organoid has increased gene expression of one or more of the following as compared to wildtype salivary gland tissue: EN1, PRAME, SOX11, SOX4, CDK4, POU3F2 and CCNB1.

In certain embodiments, the composition includes: a) a three dimensional tumor organoid comprising a plurality of cells derived from an adenoid cystic carcinoma (ACC); and b) an organoid culture medium, wherein the organoid culture medium is substantially free of R-spondins. In some embodiments, the organoid culture media includes a plurality of organoid growth factors, wherein the plurality of organoid growth factors is: a) Noggin, b) a combination of EGF, Noggin, FGF7 and FGF10, or c) a combination of EGF, Noggin, Wnt-3A, and R-spondin1. In some embodiments, the the tumor organoid includes an NFIB-MYBL1 gene fusion. In exemplary embodiments, the tumor organoid has increased gene expression of one or more of the following as compared to wildtype salivary gland tissue: EN1, PRAME, SOX11, SOX4, CDK4, POU3F2 and CCNB1. In several embodiments, the plurality of cells have a similar clonal diversity as compared to the ACC.

In some embodiments, the composition includes a) a three dimensional tumor organoid that includes a plurality of cells derived from an adenoid cystic carcinoma; and b) an organoid culture medium according to any of the organoid culture medium provided herein. In certain embodiments, the tumor organoid includes an NFIB-MYBL1 gene fusion. In some embodiments, the tumor organoid has increased gene expression of one or more of the following as compared to wildtype salivary gland tissue: EN1, PRAME, SOX11, SOX4, CDK4, POU3F2 and CCNB1.

In certain embodiments of the tumor organoid that includes a plurality of cells derived from an adenoid cystic carcinoma (ACC) described herein, the plurality of cells have a similar clonal diversity as compared to the ACC. In particular embodiments, such tumor organoids are substantially free of HeLa cells. In some embodiments, the tumor organoids are completely free of HeLa cells.

In another aspect, provided herein are compositions that include a three dimensional tumor organoid cell line and an organoid culture medium that is substantially free of R-spondins. In some embodiments, the composition includes: a) a three dimensional tumor organoid cell line; and b) an organoid culture medium. In some embodiments of this composition, the organoid culture medium is substantially free of R-spondins, and the three dimensional tumor organoid cell line includes a plurality of cells derived from an anal cancer, a basal cell skin cancer, a squamous cancer, a breast cancer, a bladder cancer, a cervical cancer, a colon cancer, an endometrial cancer, a head and neck cancer, a hepatobiliary cancer, a kidney cancer, a gastric cancer, a lung cancer, a mesothelial cancer of the pleural cavity, a mesothelial cancer of the peritoneal cavity, an ovarian cancer, prostate cancer, or a rectal cancer.

In some embodiments, the composition includes: a) a three dimensional tumor organoid that includes cells derived from a squamous cancer; and b) an organoid culture medium that includes a plurality of organoid growth factors, wherein the plurality of organoid growth factors includes EGF, and Noggin, and wherein the organoid culture medium is substantially free of R-spondins. In exemplary embodiments, the squamous cancer is squamous cell non-small cell lung carcinoma.

In certain embodiments, the composition includes: a) a three dimensional tumor organoid cell line that includes a plurality of cells derived from an adenocarcinoma; and b) an organoid culture medium that includes a plurality of organoid growth factors, wherein the plurality of organoid growth factors is: i) a combination of EGF, and Noggin, ii) a combination of EGF, Noggin, FGF7 and FGF10, or iii) a combination of EGF, Noggin, Wnt-3A, and R-spondin. In exemplary embodiments, the organoid culture medium is substantially free of any additional organoid growth factors. In some embodiments, the adenocarcinoma is adenocarcinoma non-small cell lung carcinoma.

In another embodiment, the composition includes; a) a three dimensional tumor organoid cell line that includes a plurality of cells derived from an ovarian cancer; and b) an organoid culture medium that includes a plurality of organoid growth factors, wherein the plurality of organoid growth factors is: i) a combination of EGF, and Noggin, ii) a combination of EGF, Noggin, FGF7 and FGF10, or iii) a combination of EGF, Noggin, Wnt-3A, and R-spondin1. In exemplary embodiments, the wherein organoid culture medium is substantially free of any additional organoid growth factors.

In certain embodiments, the composition includes: a) a three dimensional tumor organoid cell line that includes a plurality of cells derived from a breast cancer; and b) an organoid culture medium that includes a plurality of organoid growth factors, wherein the plurality of organoid growth factors includes EGF, Noggin, FGF7, and FGF10, and wherein the organoid culture medium is substantially free of R-spondins.

In some embodiments, the composition includes: a) a three dimensional tumor organoid cell line that includes a plurality of cells derived from a head and neck cancer; and b) an organoid culture medium that includes a plurality of organoid growth factors, wherein the plurality of organoid growth factors includes EGF, and Noggin, and wherein the organoid culture medium is substantially free of R-spondins.

In several embodiments, the composition includes: a) a three dimensional tumor organoid cell line that includes a plurality of cells derived from a gastric cancer; and b) an organoid culture medium that includes a plurality of organoid growth factors, wherein the plurality of organoid growth factors is: i) a combination of EGF, and Noggin, ii) a combination of EGF, Noggin, FGF7 and FGF10, or iii) a combination of EGF, Noggin, Wnt-3A, and R-spondin1, and wherein the organoid culture medium is substantially free of any additional organoid growth factors.

In certain embodiments, the composition includes: a) a three dimensional tumor organoid cell line that includes cells a plurality of cells derived from a colon cancer; and b) an organoid culture medium that includes a plurality of organoid growth factors, wherein the plurality of organoid growth factors is: i) a combination of EGF, and Noggin, ii) a combination of EGF, Noggin, FGF7 and FGF10, or iii) a combination EGF, Noggin, Wnt-3A, and R-spondin1, and wherein the organoid culture medium is substantially free of any additional organoid growth factors.

In some embodiments, the composition includes: a) a three dimensional tumor organoid cell line that includes a plurality of cells derived from a liver cancer; and b) an organoid culture medium that includes a plurality of organoid growth factors, wherein the plurality of organoid growth factors is: i) a combination of EGF, Noggin, FGF7 and FGF10, or ii) a combination of EGF, Noggin, Wnt-3A, and R-spondin1, and wherein the organoid culture medium is substantially free of any additional organoid growth factors.

In several embodiments, the composition includes: a) a three dimensional tumor organoid cell line that includes a plurality of cells derived from a lung cancer; and b) an organoid culture medium comprising a plurality of organoid growth factors, wherein the plurality of organoid growth factors is: i) a combination of EGF, and Noggin, ii) a combination of EGF, Noggin, FGF7 and FGF10, or iii) a combination of EGF, Noggin, Wnt-3A, and R-spondin1, and wherein the organoid culture medium is substantially free of any additional organoid growth factors.

In some embodiments, the composition includes: a) a three dimensional tumor organoid cell line that includes a plurality of cells derived from an esophageal cancer; and b) an organoid culture medium comprising a plurality of organoid growth factors, wherein the plurality of organoid growth factors is: i) a combination of EGF, and Noggin, ii) a combination of EGF, Noggin, FGF7 and FGF10, or iii) a combination of EGF, Noggin, Wnt-3A, and R-spondin1, and wherein the organoid culture medium is substantially free of any additional organoid growth factors.

In other embodiments, the composition includes: a) a three dimensional tumor organoid cell line that includes a plurality of cells derived from an endometrial cancer; and b) an organoid culture medium that includes a plurality of organoid growth factors, wherein the plurality of organoid growth factors is: i) a combination of EGF, and Noggin, ii) a combination of EGF, Noggin, FGF7 and FGF10, or iii) a combination of EGF, Noggin, Wnt-3A, and R-spondin1, and wherein the organoid culture medium is substantially free of any additional organoid growth factors.

In certain embodiments of these compositions, the organoid culture media further includes one or more molecular inhibitors that include a Rho kinase inhibitor, a transforming growth factor-beta inhibitor, a MAP kinase inhibitor or combinations thereof.

In some embodiments, the one or more molecular inhibitors includes the Rho kinase inhibitor, and wherein the Rho kinase inhibitor is Y27632. In certain embodiments, the one or more molecular inhibitors includes the transforming growth factor-beta inhibitor, and the transforming growth factor-beta inhibitor is A-83-01. In exemplary embodiments, the one or more molecular inhibitors includes the MAP kinase inhibitor, and the MAP kinase inhibitor is a P38 inhibitor. In particular embodiments, the P38 inhibitor is SB202190.

In some embodiments, the one or more molecular inhibitors includes the Rho kinase inhibitor Y27632, the transforming growth factor-beta inhibitor A-83-01, and the MAP kinase inhibitor SB202190.

In some embodiments, of the culturing methods provided herein, the organoid culture media further includes: a) a chemically-defined, minimal culture medium; b) L-glutamine; c) a serum replacement supplement; d) N-acetyl-L-cysteine; and e) nicotinamide. In particular embodiments, the chemically-defined, minimal culture medium is Dulbecco's Modified Eagle Medium, Roswell Park Memorial Institute 1640 Medium, Ham's F-12 Medium, or a combination thereof.

In exemplary embodiments, the serum replacement supplement includes holo-transferrin, insulin, superoxide dismutase, catalase enzyme, carnitine, putrescine, glutathione, galactose, corticosterone, ethanolamine, linoleic acid, linolenic acid, selenite, tri-iodothyronine, tocopherol, and progesterone. In other embodiments, the serum replacement supplement comprises insulin and holo-transferrin.

In several embodiments, the organoid culture media further includes an antibiotic. In some embodiments, the antibiotic is penicillin streptomycin.

In another aspect, provided herein is a method of evaluating an effect of a cancer therapeutic agent. The method includes the steps of: a) applying the therapeutic agent to any of the tumor organoid compositions provided herein; and b) after applying the cancer therapeutic agent to the composition, measuring a property of the culture of the tumor organoid cell line, thereby evaluating the effect of the cancer therapeutic agent. In some embodiments, the cancer therapeutic agent is an antibody or a small molecule drug. In particular embodiments, the effect evaluated is an efficacy, pharmacokinetic property, or toxicity of the cancer therapeutic. In certain embodiments, the measured property of the culture is selected from the group consisting of cell mortality, a transcriptional profile, a proteomic profile, clonal diversity, an epigenetic profile, cell morphology, a growth rate, an abundance of extracellular protein in the culture, 3-dimensional cell-cell architecture, biochemical changes in metabolites and non-metabolites, cellular membrane potential, mitochondrial membrane potential of the cultured cells, morphology or architectural changes, upregulation of autophagy, chromosomal changes in ploidy in cultured tumor cells, chromosomal breakage, telomere length changes, cytoskeletal and cell motility changes.

In some embodiments, the method further includes the steps of: c) measuring the property of a culture of the tumor organoid cell line which has not been exposed to the cancer therapeutic agent; and d) comparing the measured property of the culture that was exposed to the cancer therapeutic agent with the measured property of the culture that was not exposed to the cancer therapeutic agent.

In another aspect, provided herein is a method of evaluating an effect of a cancer therapeutic agent, the method includes the steps of: a) culturing tumor cells in an organoid culture medium, wherein the organoid culture media includes a plurality of organoid growth factors, wherein the plurality of organoid growth factors consists of one of the following combinations of organoid growth factors: i) Noggin, ii) a combination of EGF and Noggin, iii) a combination of EGF, Noggin, FGF7 and FGF10, and iv) a combination of EGF, Noggin, Wnt-3A, R-spondin1, FGF7 and FGF10, thereby generating a culture comprising a plurality of tumor organoids; b) exposing the plurality of tumor organoids to the cancer therapeutic agent; and c) after exposing the plurality of tumor organoids to the cancer therapeutic agent, measuring a property of the plurality of tumor organoids, thereby evaluating the effect of the cancer therapeutic agent.

In certain embodiments of these compositions, the organoid culture media further includes one or more molecular inhibitors that include a Rho kinase inhibitor, a transforming growth factor-beta inhibitor, a MAP kinase inhibitor or combinations thereof.

In some embodiments, the one or more molecular inhibitors includes the Rho kinase inhibitor, and wherein the Rho kinase inhibitor is Y27632. In certain embodiments, the one or more molecular inhibitors includes the transforming growth factor-beta inhibitor, and the transforming growth factor-beta inhibitor is A-83-01. In exemplary embodiments, the one or more molecular inhibitors includes the MAP kinase inhibitor, and the MAP kinase inhibitor is a P38 inhibitor. In particular embodiments, the P38 inhibitor is SB202190.

In some embodiments, the one or more molecular inhibitors includes the Rho kinase inhibitor Y27632, the transforming growth factor-beta inhibitor A-83-01, and the MAP kinase inhibitor SB202190.

In some embodiments, of the culturing methods provided herein, the organoid culture media further includes: a) a chemically-defined, minimal culture medium; b) L-glutamine; c) a serum replacement supplement; d) N-acetyl-L-cysteine; and e) nicotinamide. In particular embodiments, the chemically-defined, minimal culture medium is Dulbecco's Modified Eagle Medium, Roswell Park Memorial Institute 1640 Medium, Ham's F-12 Medium, or a combination thereof.

In exemplary embodiments, the serum replacement supplement includes holo-transferrin, insulin, superoxide dismutase, catalase enzyme, carnitine, putrescine, glutathione, galactose, corticosterone, ethanolamine, linoleic acid, linolenic acid, selenite, tri-iodothyronine, tocopherol, and progesterone. In other embodiments, the serum replacement supplement comprises insulin and holo-transferrin.

In several embodiments, the organoid culture media further includes an antibiotic. In some embodiments, the antibiotic is penicillin streptomycin.

In some embodiments, the method further includes the steps of: d) measuring the property of a culture of the tumor organoid cell line which has not been exposed to the cancer therapeutic agent; and e) comparing the measured property of the culture that was exposed to the cancer therapeutic agent with the measured property of the culture that was not exposed to the cancer therapeutic agent.

In another aspect, provided herein is a method for evaluating the clonal diversity of a tumor organoid cell line using genomic variant profiles. In some embodiments, the method includes: a) obtaining a tumor sample from a subject; b) determining a reference genomic variant profile, wherein the reference genomic variant profile includes, for each respective somatic variant in a plurality of somatic variants identified in a reference, a relative abundance value for the respective somatic variant in the reference genome; c) culturing the tumor organoid cell line that includes at least one tumor organoid in an organoid culture medium, wherein each respective tumor organoid in the tumor organoid cell line is derived from one or more cells of the tumor sample; d) determining a first organoid genomic variant profile of the tumor organoid cell line, wherein the first organoid genomic variant profile includes, for each respective somatic variant in a plurality of somatic variants identified in the tumor organoid cell line, a relative abundance value for the respective somatic variant in the tumor organoid culture; and e) evaluating the similarity or dissimilarity between the reference genomic variant profile and the first organoid genomic variant profile.

In some embodiments, the reference is the tumor sample. In certain embodiments, the tumor sample is a solid tumor sample. In several embodiments, the tumor sample includes biopsied material from a plurality of regions of a tumor. In particular embodiments, the tumor sample includes biopsied material from a plurality of tumors from the subject. In exemplary embodiments, the reference is a liquid biological sample obtained from the subject.

In some embodiments, the reference genomic profile is determined using nucleic acids isolated from the reference. In certain embodiments, the first organoid genomic variant profile is determined using nucleic acids isolated from the at least one tumor organoid. In certain embodiments, the first organoid genomic variant profile is determined using nucleic acids isolated from the organoid culture medium. In some embodiments, isolated nucleic acids comprise DNA. In certain embodiments, the isolated nucleic acids comprise RNA.

In several embodiments, the method includes evaluating a property of the tumor organoid cell line. In some embodiments the property is evaluated over the course of a set time period. In certain embodiments, the time period is at least 1, 5, 10, 15, 20, 25, 30, 35, 40, 45, 50, 55, or 60 minutes. In several embodiments, the time period is at least 1, 2, 3, 4, 5, 6, 7, 8, 9, 10, 11, 12, 13, 14, 15, 16, 17, 18, 19, 20, 21, 22, 23, or 24 hours. In some embodiments, the time period is at least 1, 2, 3, 4, 5, 6, or 7 days. In some embodiments, the time period is at least 1, 2, 3, or 4 weeks. In several embodiments, the time period is at least 1, 2, 3, 4, 5, 6, 7, 8, 9, 10, 11 or 12 months. In some embodiments, the time period is at least 1, 2, 3, 4, 5, 6, 7, 8, 9, 10 years. In some embodiments, a cellular growth characteristic of the tumor organoid cell line is evaluated over time. In certain embodiments, a morphological property of the tumor organoid cell line is evaluated over time. A particular embodiments, a physiological property of the tumor organoid cell line is evaluated over time. In exemplary embodiments, a clonal diversity of the tumor organoid cell line is evaluated over time.

In some embodiments, the method further includes: f) exposing the tumor organoid cell line to a therapeutic agent; and g) after exposing the tumor organoid cell line to a therapeutic agent, evaluating a property of the exposed tumor organoid cell line.

In exemplary embodiments, prior to the exposing f), the method includes confirming that the first organoid genomic variant profile satisfies a threshold level of similarity with the reference genomic variant profile.

In some embodiments, the evaluating g) includes: determining a second organoid genomic variant profile of the tumor organoid cell line after exposure of the tumor organoid cell line to the therapeutic agent, wherein the second organoid genomic variant profile includes, for each respective somatic variant identified in a plurality of somatic variants identified in the tumor organoid cell line after exposure to the therapeutic agent, a relative abundance value for the respective somatic variant; and evaluating a difference or similarity between the first organoid genomic variant profile and the second organoid genomic variant profile.

In some embodiments, the second organoid genomic variant profile is determined using nucleic acids isolated from the at least one tumor organoid in the tumor organoid cell line after exposure of the tumor organoid cell line to the therapeutic agent. In certain embodiments, the second organoid genomic variant profile is determined using nucleic acids isolated from the organoid culture medium after exposure of the tumor organoid cell line to the therapeutic agent. In exemplary embodiments, evaluating the difference or similarity includes determining which somatic variants experienced a threshold level of change between the first organoid genomic variant profile and the second organoid genomic variant profile. In some embodiments, evaluating the difference or similarity includes inputting the first organoid genomic variant profile and the second organoid genomic variant profile, or a difference between the first organoid genomic variant profile and the second organoid genomic variant profile, into a classifier trained to distinguish between a plurality of tumor classifications.

In certain embodiments, the method further includes assigning a therapy to the subject based on a property of the tumor organoid cell line. In some embodiments, the threshold level of similarity is a threshold concordance between the first organoid genomic variant profile and the second organoid genomic variant profile.

In some embodiments of the method, the organoid culture medium includes: i) a plurality of organoid growth factors, wherein the plurality of organoid growth factors includes of one of the following combinations of organoid growth factors: a) Noggin, b) a combination of EGF and Noggin, c) a combination of EGF, Noggin, FGF7 and FGF10, d) a combination of EGF, Noggin, Wnt-3A, and R-spondin1, and e) a combination of EGF, Noggin, Wnt-3A, R-spondin1, FGF7 and FGF10; and ii) a plurality of molecular inhibitors that include a Rho kinase inhibitor, a transforming growth factor-beta inhibitor and a MAP kinase inhibitor.

In some embodiments, the one or more molecular inhibitors includes the Rho kinase inhibitor Y27632, the transforming growth factor-beta inhibitor A-83-01, and the MAP kinase inhibitor SB202190.

In some embodiments, of the culturing methods provided herein, the organoid culture media further includes: a) a chemically-defined, minimal culture medium; b) L-glutamine; c) a serum replacement supplement; d) N-acetyl-L-cysteine; and e) nicotinamide. In particular embodiments, the chemically-defined, minimal culture medium is Dulbecco's Modified Eagle Medium, Roswell Park Memorial Institute 1640 Medium, Ham's F-12 Medium, or a combination thereof.

In exemplary embodiments, the serum replacement supplement includes holo-transferrin, insulin, superoxide dismutase, catalase enzyme, carnitine, putrescine, glutathione, galactose, corticosterone, ethanolamine, linoleic acid, linolenic acid, selenite, tri-iodothyronine, tocopherol, and progesterone. In other embodiments, the serum replacement supplement comprises insulin and holo-transferrin.

In several embodiments, the organoid culture media further includes an antibiotic. In some embodiments, the antibiotic is penicillin streptomycin.

In another aspect, provided herein is a method for evaluating the clonal diversity of a tumor organoid cell line using transcript profiles. The method includes the steps of: a) obtaining a tumor sample from a subject; b) determining a reference transcript profile, wherein the reference transcript profile includes, for each respective transcript in a plurality of transcripts identified in a reference, a relative abundance value for the respective transcript in the reference; c) culturing the tumor organoid cell line comprising at least one tumor organoid in an organoid culture medium, wherein each respective tumor organoid in the tumor organoid cell line is derived from one or more cells of the tumor sample; d) determining a first organoid transcript profile of the tumor organoid cell line, wherein the first organoid transcript profile includes, for each respective transcript in a plurality of transcripts identified in the tumor organoid cell line, a relative abundance value for the respective transcript in the tumor organoid culture; and e) evaluating the similarity or dissimilarity between the reference transcript profile and the first organoid transcript variant profile.

In some embodiments, the reference is the tumor sample. In certain embodiments, the tumor sample is a solid tumor sample. In several embodiments, the tumor sample includes biopsied material from a plurality of regions of a tumor. In particular embodiments, the tumor sample includes biopsied material from a plurality of tumors from the subject. In exemplary embodiments, the reference is a liquid biological sample obtained from the subject.

In some embodiments, the reference genomic profile is determined using nucleic acids isolated from the reference. In certain embodiments, the first organoid genomic variant profile is determined using nucleic acids isolated from the at least one tumor organoid. In certain embodiments, the first organoid genomic variant profile is determined using nucleic acids isolated from the organoid culture medium. In exemplary embodiments, the isolated nucleic acids include mRNA.

In several embodiments, the method includes evaluating a property of the tumor organoid cell line. In some embodiments, a cellular growth characteristic of the tumor organoid cell line is evaluated over time. In some embodiments the property is evaluated over the course of a set time period. In certain embodiments, the time period is at least 1, 5, 10, 15, 20, 25, 30, 35, 40, 45, 50, 55, or 60 minutes. In several embodiments, the time period is at least 1, 2, 3, 4, 5, 6, 7, 8, 9, 10, 11, 12, 13, 14, 15, 16, 17, 18, 19, 20, 21, 22, 23, or 24 hours. In some embodiments, the time period is at least 1, 2, 3, 4, 5, 6, or 7 days. In some embodiments, the time period is at least 1, 2, 3, or 4 weeks. In several embodiments, the time period is at least 1, 2, 3, 4, 5, 6, 7, 8, 9, 10, 11 or 12 months. In some embodiments, the time period is at least 1, 2, 3, 4, 5, 6, 7, 8, 9, 10 years. In certain embodiments, a morphological property of the tumor organoid cell line is evaluated over time. In particular embodiments, a physiological property of the tumor organoid cell line is evaluated over time. In exemplary embodiments, a clonal diversity of the tumor organoid cell line is evaluated over time.

In some embodiments, the method further includes the steps of: f) exposing the tumor organoid cell line to a therapeutic agent; and g) after exposing the tumor organoid cell line to a therapeutic agent, evaluating a property of the exposed tumor organoid cell line.

In exemplary embodiments, the evaluating g) includes: determining a second organoid transcript profile of the tumor organoid cell line after exposure of the tumor organoid cell line to the therapeutic agent, wherein the second organoid transcript profile includes, for each respective transcript identified in a plurality of transcripts identified in the tumor organoid cell line after exposure to the therapeutic agent, a relative abundance value for the respective transcript; and evaluating a difference or similarity between the first organoid transcript profile and the second organoid transcript profile. In certain embodiments, the second organoid transcript profile is determined using nucleic acids isolated from the at least one tumor organoid in the tumor organoid cell line after exposure of the tumor organoid cell line to the therapeutic agent. In some embodiments, the second transcript variant profile is determined using nucleic acids isolated from the organoid culture medium after exposure of the tumor organoid cell line to the therapeutic agent.

In some embodiments, the evaluating the difference or similarity includes determining which transcripts experienced a threshold level of change between the first organoid transcript profile and the second organoid transcript profile. In several embodiments, the evaluating the difference or similarity includes inputting the first organoid transcript profile and the second organoid transcript profile, or a difference between the first organoid transcript profile and the second organoid transcript profile, into a classifier trained to distinguish between a plurality of tumor classifications.

In certain embodiments, the method further includes assigning a therapy to the subject based on a property of the tumor organoid cell line.

In some embodiments, prior to the exposing f), the method includes confirming that the first transcript profile for the tumor organoid cell line satisfies a threshold level of similarity with the reference transcript profile. In exemplary embodiments, the threshold level of similarity is a threshold concordance between the first organoid transcript profile and the second organoid transcript profile.

In some embodiments of the method, the organoid culture medium includes: i) a plurality of organoid growth factors, wherein the plurality of organoid growth factors includes of one of the following combinations of organoid growth factors: a) Noggin, b) a combination of EGF and Noggin, c) a combination of EGF, Noggin, FGF7 and FGF10, d) a combination of EGF, Noggin, Wnt-3A, and R-spondin1, and e) a combination of EGF, Noggin, Wnt-3A, R-spondin1, FGF7 and FGF10; and ii) a plurality of molecular inhibitors that include a Rho kinase inhibitor, a transforming growth factor-beta inhibitor and a MAP kinase inhibitor.

In some embodiments, the one or more molecular inhibitors includes the Rho kinase inhibitor Y27632, the transforming growth factor-beta inhibitor A-83-01, and the MAP kinase inhibitor SB202190.

In some embodiments, of the culturing methods provided herein, the organoid culture media further includes: a) a chemically-defined, minimal culture medium; b) L-glutamine; c) a serum replacement supplement; d) N-acetyl-L-cysteine; and e) nicotinamide. In particular embodiments, the chemically-defined, minimal culture medium is Dulbecco's Modified Eagle Medium, Roswell Park Memorial Institute 1640 Medium, Ham's F-12 Medium, or a combination thereof.

In exemplary embodiments, the serum replacement supplement includes holo-transferrin, insulin, superoxide dismutase, catalase enzyme, carnitine, putrescine, glutathione, galactose, corticosterone, ethanolamine, linoleic acid, linolenic acid, selenite, tri-iodothyronine, tocopherol, and progesterone. In other embodiments, the serum replacement supplement comprises insulin and holo-transferrin.

In several embodiments, the organoid culture media further includes an antibiotic. In some embodiments, the antibiotic is penicillin streptomycin.

In another aspect, provided herein is a method for evaluating the clonal diversity of a tumor organoid cell line. The method includes the steps of: a) obtaining a tumor sample from a subject; b) culturing the tumor organoid cell line comprising at least one tumor organoid in an organoid culture medium, wherein each respective tumor organoid in the plurality of tumor organoids is derived from one or more cells of the tumor sample; c) determining an organoid genomic variant profile of the tumor organoid cell line, wherein the organoid genomic variant profile includes, for each respective somatic variant in a plurality of somatic variants identified in the tumor organoid cell line, a relative abundance value for the respective somatic variant; d) obtaining a first liquid biological sample from the subject at a first time point; e) determining a first liquid genomic variant profile from cell-free nucleic acids isolated from the first liquid biological sample, wherein the first liquid genomic variant profile includes, for each respective somatic variant in a plurality of somatic variants identified in the first liquid biological sample, a relative abundance value for the respective somatic variant; and f) evaluating a similarity or dissimilarity between the first organoid genomic variant profile and the first liquid variant profile.

In some embodiments, no cancer therapy is administered to the subject during the time period between when the tumor sample was obtained from the subject and when the first liquid biological sample was obtained from the subject.

In certain embodiments, the liquid biological sample is a blood sample or a blood plasma sample.

In some embodiments, the organoid genomic variant profile is determined using nucleic acids isolated from the at least one tumor organoid. In certain embodiments, the organoid genomic variant profile is determined using nucleic acids isolated from the organoid culture medium. In several embodiments, the nucleic acids isolated from the plurality of tumor organoids comprise DNA. In certain embodiments, the nucleic acids isolated from the plurality of tumor organoids comprise RNA.

In exemplary embodiments, the method further includes assigning a cancer therapy to the subject based on the evaluating f).

In some embodiments, this method further includes the steps of: g) obtaining a second liquid biological sample from the subject at a second time point that is after the first time point; h) determining a second liquid genomic variant profile from cell-free nucleic acids isolated from the second liquid biological sample, wherein the second liquid genomic variant profile includes, for each respective somatic variant in a plurality of somatic variants identified in the second liquid biological sample, a relative abundance value for the respective somatic variant; and i) evaluating a similarity or dissimilarity between the second liquid genomic variant profile and the first liquid genomic variant profile. In certain embodiments, the method further includes altering a cancer therapy regimen assigned to the subject based upon the evaluating i). In some embodiments the first time point and second time point are at least 1, 5, 10, 15, 20, 25, 30, 35, 40, 45, 50, 55, or 60 minutes apart. In certain embodiments, the first time point and second time point are at least 1, 2, 3, 4, 5, 6, 7, 8, 9, 10, 11, 12, 13, 14, 15, 16, 17, 18, 19, 20, 21, 22, 23, 24 hours apart. In some embodiments, the first time point and second time point are at least 1, 2, 3, 4, 5, 6, or 7 days apart. In some embodiments, the first time point and second time point are at least 1, 2, 3, or 4 weeks apart. In several embodiments, the first time point and second time point are at least 1, 2, 3, 4, 5, 6, 7, 8, 9, 10, 11 or 12 months apart. In some embodiments, the first time point and second time point are at least 1, 2, 3, 4, 5, 6, 7, 8, 9, 10 years apart.

In some embodiments, the evaluating the similarity or dissimilarity includes determining which somatic variants experienced a threshold level of change between the first liquid genomic variant profile and the second liquid genomic variant profile. In particular embodiments, the evaluating the similarity or dissimilarity includes inputting the first liquid genomic variant profile and the second liquid variant profile, or a difference between the first liquid genomic variant profile and the second liquid variant profile, into a classifier trained to distinguish between a plurality of tumor classifications.

In some embodiments of this method, the subject was administered a cancer therapeutic agent prior to obtaining the second liquid biological sample.

In some embodiments of the method, the organoid culture medium includes: i) a plurality of organoid growth factors, wherein the plurality of organoid growth factors includes of one of the following combinations of organoid growth factors: a) Noggin, b) a combination of EGF and Noggin, c) a combination of EGF, Noggin, FGF7 and FGF10, d) a combination of EGF, Noggin, Wnt-3A, and R-spondin1, and e) a combination of EGF, Noggin, Wnt-3A, R-spondin1, FGF7 and FGF10; and ii) a plurality of molecular inhibitors that include a Rho kinase inhibitor, a transforming growth factor-beta inhibitor and a MAP kinase inhibitor.

In some embodiments, the one or more molecular inhibitors includes the Rho kinase inhibitor Y27632, the transforming growth factor-beta inhibitor A-83-01, and the MAP kinase inhibitor SB202190.

In some embodiments of the culturing methods provided herein, the organoid culture media further includes: a) a chemically-defined, minimal culture medium; b) L-glutamine; c) a serum replacement supplement; d) N-acetyl-L-cysteine; and e) nicotinamide. In particular embodiments, the chemically-defined, minimal culture medium is Dulbecco's Modified Eagle Medium, Roswell Park Memorial Institute 1640 Medium, Ham's F-12 Medium, or a combination thereof.

In exemplary embodiments, the serum replacement supplement includes holo-transferrin, insulin, superoxide dismutase, catalase enzyme, carnitine, putrescine, glutathione, galactose, corticosterone, ethanolamine, linoleic acid, linolenic acid, selenite, tri-iodothyronine, tocopherol, and progesterone. In other embodiments, the serum replacement supplement comprises insulin and holo-transferrin.

In several embodiments, the organoid culture media further includes an antibiotic. In some embodiments, the antibiotic is penicillin streptomycin.

In another aspect, provided herein is a method for evaluating the clonal diversity of a cancer in a subject, the method includes: at a computer system comprising at least one processor and a memory storing at least one program for execution by the at least one processor, the at least one program comprising instructions for: a) obtaining a first plurality of sequence reads, in electronic form, of nucleic acids in an organoid culture system comprising at least one tumor organoid cultured in an organoid culture media, wherein each respective tumor organoid in the least one tumor organoid is derived from one or more cells of a tumor sample from the subject; b) determining, from the first plurality of sequence reads, an organoid genomic variant profile, wherein the organoid genomic variant profile includes, for each respective somatic variant in a plurality of somatic variants identified in the tumor organoid cell line, a relative abundance value for the respective somatic variant; c) obtaining a second plurality of sequence reads, in electronic form, of cell-free nucleic acids obtained from a first liquid biological sample from the subject, wherein the first liquid biological sample was obtained from the subject at a first time point; d) determining, from the second plurality of sequence reads, an liquid genomic variant profile, wherein the liquid genomic variant profile includes, for each respective somatic variant in a plurality of somatic variants identified in the first liquid biological sample, a relative abundance value for the respective somatic variant; and e) evaluating a similarity or dissimilarity between the first organoid genomic variant profile and the first liquid variant profile. In some embodiments the first time point and second time point are at least 1, 5, 10, 15, 20, 25, 30, 35, 40, 45, 50, 55, or 60 minutes apart. In certain embodiments, the first time point and second time point are at least 1, 2, 3, 4, 5, 6, 7, 8, 9, 10, 11, 12, 13, 14, 15, 16, 17, 18, 19, 20, 21, 22, 23, 24 hours apart. In some embodiments, the first time point and second time point are at least 1, 2, 3, 4, 5, 6, or 7 days apart. In some embodiments, the first time point and second time point are at least 1, 2, 3, or 4 weeks apart. In several embodiments, the first time point and second time point are at least 1, 2, 3, 4, 5, 6, 7, 8, 9, 10, 11 or 12 months apart. In some embodiments, the first time point and second time point are at least 1, 2, 3, 4, 5, 6, 7, 8, 9, 10 years apart.

In one aspect, provided herein is a non-transitory computer-readable storage medium having stored thereon program code instructions that, when executed by a processor, cause the processor to perform a method for evaluating the clonal diversity of a cancer in a subject according to the subject method.

In another aspect, provided herein is computer system for evaluating the clonal diversity of a cancer in a subject, the computer system comprising at least one processor and a memory storing at least one program for execution by the at least one processor, the at least one program comprising instructions for performing the subject method.

BRIEF DESCRIPTION OF THE DRAWINGS

FIG. 5B illustrates the variant allele fraction (VAF) for each somatic variant identified and verified in both the tumor sample and the tumor organoid cell line. FIG. 5C illustrates a plot of the correlation between the variant allele fraction determined from the tumor fraction and the tumor organoid cell line.

FIG. 6B illustrates the variant allele fraction (VAF) for each somatic variant identified and verified in both the tumor sample and the tumor organoid cell line. FIG. 6C illustrates a plot of the correlation between the variant allele fraction determined from the tumor fraction and the tumor organoid cell line.

FIG. 7B illustrates the variant allele fraction (VAF) for each somatic variant identified and verified in both the tumor sample and the tumor organoid cell line. FIG. 7C illustrates a plot of the correlation between the variant allele fraction determined from the tumor fraction and the tumor organoid cell line.

FIG. 8B illustrates the variant allele fraction (VAF) for each somatic variant identified and verified in both the tumor sample and the tumor organoid cell line. FIG. 8C illustrates a plot of the correlation between the variant allele fraction determined from the tumor fraction and the tumor organoid cell line.

FIG. 9B illustrates the variant allele fraction (VAF) for each somatic variant identified and verified in both the tumor sample and the tumor organoid cell line. FIG. 9C illustrates a plot of the correlation between the variant allele fraction determined from the tumor fraction and the tumor organoid cell line.

Like reference numerals refer to corresponding parts throughout the several views of the drawings.

DETAILED DESCRIPTION

I. Overview

Figure 1A:
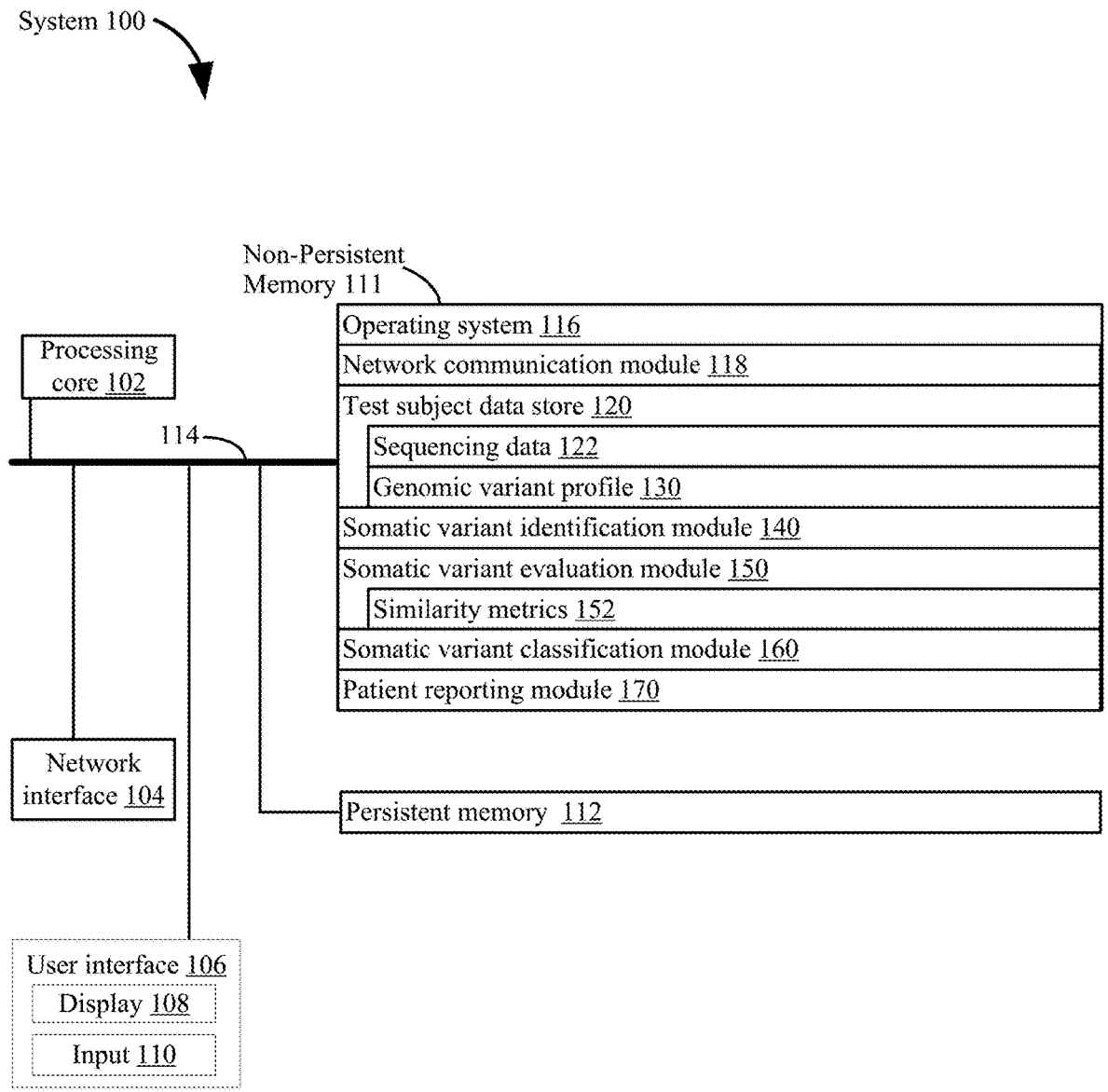
FIG. 1A, FIG. 1B, and FIG. 1C collectively illustrate a block diagram of an example of a computing device for evaluating the clonal diversity of a cancer in a subject, in accordance with some embodiments of the present disclosure.

Provided herein are novel organoid culture media, organoid culture systems, and methods of culturing tumor organoids using the subject organoid culture media. Also provided herein are tumor organoids developed using such organoid culture systems, methods for assessing the clonal diversity of the tumor organoids, and methods for using such tumor organoids, for example, for tumor modelling and drug development applications. The tumor organoid culture media provided herein advantageously can be used to culture more than one type of tumor organoid and require fewer growth factors as compared to traditional organoid culture media. In certain embodiments, the tumor organoid culture media provided herein is substantially free of R-spondins (e.g., R-spondin1). As such, the subject organoid growth media reduce problems associated with traditional organoid culture media including, for example, growth factor production, variability in activity, component costs, and large-scale use. In some embodiments, the subject organoid culture medium support the growth and development of tumor organoids that exhibit similar clonal diversity to the source cancer from which the tumor organoid is derived. Thus, the tumor organoids cultured using the methods and compositions provided herein provide useful models for the source tumors from which such tumor organoids are derived.

II. Definitions

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Furthermore, to the extent that the terms "including," "includes," "having," "has," "with," or variants thereof are used in either the detailed description and/or the claims, such terms are intended to be inclusive in a manner similar to the term "comprising."

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject," "user," and "patient" are used interchangeably herein.

As used herein, the term "subject" refers to any living or non-living human. In some embodiments, a subject is a male or female of any stage (e.g., a man, a women or a child).

As used herein, the terms "control," "control sample," "reference," "reference sample," "normal," and "normal sample" describe a sample from a subject that does not have a particular condition, or is otherwise healthy. In an example, a method as disclosed herein can be performed on a subject having a tumor, where the reference sample is a sample taken from a healthy tissue of the subject. A reference sample can be obtained from the subject, or from a database. The reference can be, e.g., a reference genome that is used to map sequence reads obtained from sequencing a sample from the subject. A reference genome can refer to a haploid or diploid genome to which sequence reads from the biological sample and a constitutional sample can be aligned and compared. An example of constitutional sample can be DNA of white blood cells obtained from the subject. For a haploid genome, there can be only one nucleotide at each locus. For a diploid genome, heterozygous loci can be identified; each heterozygous locus can have two alleles, where either allele can allow a match for alignment to the locus.

As used herein, the term "locus" refers to a position (e.g., a site) within a genome, e.g., on a particular chromosome. In some embodiments, a locus refers to a single nucleotide position within a genome, i.e., on a particular chromosome. In some embodiments, a locus refers to a small group of nucleotide positions within a genome, e.g., as defined by a mutation (e.g., substitution, insertion, or deletion) of consecutive nucleotides within a cancer genome. Because normal mammalian cells have diploid genomes, a normal mammalian genome (e.g., a human genome) will generally have two copies of every locus in the genome, or at least two copies of every locus located on the autosomal chromosomes, e.g., one copy on the maternal autosomal chromosome and one copy on the paternal autosomal chromosome.

As used herein, the term "allele" refers to a particular sequence of one or more nucleotides at a chromosomal locus.

As used herein, the term "reference allele" refers to the sequence of one or more nucleotides at a chromosomal locus that is either the predominant allele represented at that chromosomal locus within the population of the species (e.g., the "wild-type" sequence), or an allele that is predefined within a reference genome for the species.

As used herein, the term "variant allele" refers to a sequence of one or more nucleotides at a chromosomal locus that is either not the predominant allele represented at that chromosomal locus within the population of the species (e.g., not the "wild-type" sequence), or not an allele that is predefined within a reference genome for the species.

As used herein, the term "single nucleotide variant" or "SNV" refers to a substitution of one nucleotide to a different nucleotide at a position (e.g., site) of a nucleotide sequence, e.g., a sequence read from an individual. A substitution from a first nucleobase X to a second nucleobase Y may be denoted as "X>Y." For example, a cytosine to thymine SNV may be denoted as "C>T."

As used herein, the term "mutation" or "variant" refers to a detectable change in the genetic material of one or more cells. In a particular example, one or more mutations can be found in, and can identify, cancer cells (e.g., driver and passenger mutations). A mutation can be transmitted from apparent cell to a daughter cell. A person having skill in the art will appreciate that a genetic mutation (e.g., a driver mutation) in a parent cell can induce additional, different mutations (e.g., passenger mutations) in a daughter cell. A mutation generally occurs in a nucleic acid. In a particular example, a mutation can be a detectable change in one or more deoxyribonucleic acids or fragments thereof. A mutation generally refers to nucleotides that is added, deleted, substituted for, inverted, or transposed to a new position in a nucleic acid. A mutation can be a spontaneous mutation or an experimentally induced mutation. A mutation in the sequence of a particular tissue is an example of a "tissue-specific allele." For example, a tumor can have a mutation that results in an allele at a locus that does not occur in normal cells. Another example of a "tissue-specific allele" is a fetal-specific allele that occurs in the fetal tissue, but not the maternal tissue.

As used herein, the term "somatic variant" refers to a mutation in the genome of a cancerous tissue of a subject, or a tumor organoid cell line derived from a cancerous tissue of the subject, which is not present in the germline of the subject. In many instances, a somatic variant is present in only a percentage of all cancerous tissues in a subject. Likewise, in many instances, a somatic variant is present in only a percentage of all cancerous cells within a single tumor in the subject. Somatic variants include, but are not limited to, point mutations, nonsense mutations, frame shift, deletions, duplications, insertions (e.g., in frame insertions), missense mutation, repeat expansion, indels, exon duplications, fusions, translocations and splice region mutations.

As used herein the term "cancer," "cancerous tissue," or "tumor" refers to an abnormal mass of tissue in which the growth of the mass surpasses and is not coordinated with the growth of normal tissue. A cancer or tumor can be defined as "benign" or "malignant" depending on the following characteristics: degree of cellular differentiation including morphology and functionality, rate of growth, local invasion and metastasis. A "benign" tumor can be well differentiated, have characteristically slower growth than a malignant tumor and remain localized to the site of origin. In addition, in some cases a benign tumor does not have the capacity to infiltrate, invade or metastasize to distant sites. A "malignant" tumor can be a poorly differentiated (anaplasia), have characteristically rapid growth accompanied by progressive infiltration, invasion, and destruction of the surrounding tissue. Furthermore, a malignant tumor can have the capacity to metastasize to distant sites. Accordingly, a cancer cell is a cell found within the abnormal mass of tissue whose growth is not coordinated with the growth of normal tissue. Accordingly, a "tumor sample" refers to a biological sample obtained or derived from a tumor of a subject, as described herein.

As used herein, the term "organoid" refers to an in vitro three-dimensional multicellular construct that is developed from stem cells (e.g., embryonic stem cells, induced pluripotent stem cells, and somatic stem cells or tissue derived progenitor cells) or cancer cells in a specific 3D organoid culture system. Organoids contain multiple cells types of the in vivo counter parts and organize similarly to the primary tissue. In some embodiments, the organoid culture system includes an organoid culture medium and an extracellular matrix or extracellular matrix substitute. An "organoid cell line" refers to a plurality of organoids that are derived and established from the same cell or cell population. A "tumor organoid" refers to an organoid derived from a tumor cell or population of tumor cells.

As used herein, the term "clonal diversity" refers to the different cell clones present within a cell population due, at least in part, to the somatic variants that arise during cell division. In cancers, somatic variants accumulate in different populations of cells during clonal expansion over the course of disease, thereby creating a mixture of cancer cell clones in the tumor with genetic and morphological heterogeneity. Tumor clonal diversity can arise due to random mutations that occur during cell divisions of cancer cells or through mutational events stimulated by various exposures. Clonal diversity can be measured using any suitable technique. In some embodiments, clonal diversity of a defined population (e.g., a tumor organoid cell line, a source tumor or the subject of the source tumor) is determined based on the allelic frequency at one or more gene loci of interest in the population. In some embodiments, clonal diversity is inferred based on the presence and/or frequency of one or somatic variants. Somatic variants include, but are not limited to, point mutations, nonsense mutations, frame shift, deletions, duplications, insertions (e.g., in frame insertions), missense mutation, repeat expansion, indels, exon duplications, fusions, translocations and splice region mutations. In some embodiments, clonal diversity in a cell population is inferred using probabilistic reasoning, such as Bayesian or frequentist statistical approaches based, at least in part, on variant allelic frequency (VAF) data, copy number variation (CNV) data, and/or loss of heterozygosity (LOH) data from the cell population.

As used herein, the term "genomic variant profile" refers to a profile of the presence and/or frequency of one or more alleles (e.g., somatic variants) at one or more gene loci interests. Genomic variant profiles can be determined for single cells, a cell population, a single subject or a population of subjects. In some embodiments, a genomic variant profile includes allelic information relating to at least 1, 2, 5, 10, 15, 20, 25, 30, 35, 40, 45, 50, 55, 60, 65, 75, 80, 85, 90, 95, 100, 150, 200, 250, 300, 350, 400, 450, 500, 600, 700, 800, 900, 100 gene loci of interest. In some embodiments, a genomic variant profile includes allelic information relating to at least 1, 10, $1 \times 10^2$, $1 \times 10^3$, $1 \times 10^4$, $1 \times 10^5$, $1 \times 10^6$, $1 \times 10^7$, $1 \times 10^8$, $1 \times 10^9$, or $3 \times 10^9$ gene loci of interest. Genomic variant profiles can be obtained using any suitable technique in art. For example, genomic variant profiles can be obtained by genomic sequencing (e.g., next generation sequencing) and determining the variant allelic frequency (VAF) for at least two or more different gene loci of interest.

As used herein, the term "transcript profile" refers to a profile of the presence and/or frequency of one or more transcripts at one or more gene loci interests. Transcript profiles can be determined for single cells, a cell population, a single subject or a population of subjects. Transcripts that can be included in transcript profiles include, but are not limited to, single nucleotide variants, fusions, splice variants, and/or isoform variants. In some embodiments, a transcript profile includes at least 1, 2, 5, 10, 15, 20, 25, 30, 35, 40, 45, 50, 55, 60, 65, 75, 80, 85, 90, 95, 100, 150, 200, 250, 300, 350, 400, 450, 500, $1 \times 10^3$, $1 \times 10^4$, or $1 \times 10^5$ identified transcripts. Transcript profiles can be obtained using any suitable technique in art. For example, transcript profiles can be obtained by data obtained fro RNA-Seq sequencing.

As used herein, the terms "sequencing," "sequence determination," and the like as used herein refers generally to any and all biochemical processes that may be used to determine the residue order of biological macromolecules such as nucleic acids or proteins. For example, sequencing data can include all or a portion of the nucleotide bases in a nucleic acid molecule such as an mRNA transcript or a genomic locus.

As used herein, the term "sequence reads" or "reads" or "read segment" refers to nucleotide sequences produced by any sequencing process described herein or known in the art. Reads can be generated from one end of nucleic acid fragments ("single-end reads"), and sometimes are generated from both ends of nucleic acids (e.g., paired-end reads, double-end reads). The length of the sequence read is often associated with the particular sequencing technology. High-throughput methods, for example, provide sequence reads that can vary in size from tens to hundreds of base pairs (bp). In some embodiments, the sequence reads are of a mean, median or average length of about 15 bp to 900 bp long (e.g., about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. In some embodiments, the sequence reads are of a mean, median or average length of about 1000 bp, 2000 bp, 5000 bp, 10,000 bp, or 50,000 bp or more. Nanopore sequencing, for example, can provide sequence reads that can vary in size from tens to hundreds to thousands of base pairs. Illumina parallel sequencing can provide sequence reads that do not vary as much, for example, most of the sequence reads can be smaller than 200 bp. A sequence read (or sequencing read) can refer to sequence information corresponding to a nucleic acid molecule (e.g., a string of nucleotides). For example, a sequence read can correspond to a string of nucleotides (e.g., about 20 to about 150) from part of a nucleic acid fragment, can correspond to a string of nucleotides at one or both ends of a nucleic acid fragment, or can correspond to nucleotides of the entire nucleic acid fragment. A sequence read can be obtained in a variety of ways, e.g., using sequencing techniques or using probes, e.g., in hybridization arrays or capture probes, or amplification techniques, such as the polymerase chain reaction (PCR) or linear amplification using a single primer or isothermal amplification. Sequence reads can be obtained from an individual and/or nucleotide sequences derived from the initial sequence read from a sample obtained from an individual. For example, a read segment can refer to an aligned sequence read, a collapsed sequence read, or a stitched read. Furthermore, a read segment can refer to an individual nucleotide base, such as a single nucleotide variant.

As used herein, the term, "reference exome" refers to any particular known, sequenced or characterized exome, whether partial or complete, of any tissue from any organism or pathogen that may be used to reference identified sequences from a subject. Example reference exomes used for human subjects as well as many other organisms are provided in the on-line genome browser hosted by the National Center for Biotechnology Information ("NCBI").

As used herein, the term "reference genome" refers to any particular known, sequenced or characterized genome, whether partial or complete, of any organism or pathogen that may be used to reference identified sequences from a subject. Exemplary reference genomes used for human subjects as well as many other organisms are provided in the on-line genome browser hosted by the National Center for Biotechnology Information ("NCBI") or the University of California, Santa Cruz (UCSC). A "genome" refers to the complete genetic information of an organism or pathogen, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. The reference genome can be viewed as a representative example of a species' set of genes. In some embodiments, a reference genome comprises sequences assigned to chromosomes. Exemplary human reference genomes include but are not limited to NCBI build 34 (UCSC equivalent: hg16), NCBI build 35 (UCSC equivalent: hg17), NCBI build 36.1 (UCSC equivalent: hg18), GRCh37 (UCSC equivalent: hg19), and GRCh38 (UCSC equivalent: hg38).

As used herein, the term "assay" refers to a technique for determining a property of a substance, e.g., a nucleic acid, a protein, a cell, a tissue, or an organ. An assay (e.g., a first assay or a second assay) can comprise a technique for determining the copy number variation of nucleic acids in a sample, the methylation status of nucleic acids in a sample, the fragment size distribution of nucleic acids in a sample, the mutational status of nucleic acids in a sample, or the fragmentation pattern of nucleic acids in a sample. Any assay known to a person having ordinary skill in the art can be used to detect any of the properties of nucleic acids mentioned herein. Properties of a nucleic acids can include a sequence, genomic identity, copy number, methylation state at one or more nucleotide positions, size of the nucleic acid, presence or absence of a mutation in the nucleic acid at one or more nucleotide positions, and pattern of fragmentation of a nucleic acid (e.g., the nucleotide position(s) at which a nucleic acid fragments). An assay or method can have a particular sensitivity and/or specificity, and their relative usefulness as a diagnostic tool can be measured using ROC-AUC statistics.

The term "classification" can refer to any number(s) or other characters(s) that are associated with a particular property of a sample. For example, in some embodiments, the term "classification" can refer to a type of cancer in a subject or sample, a stage of cancer in a subject or sample, a prognosis for a cancer in a subject or sample, a tumor load in a subject, a presence of tumor metastasis in a subject, and the like. The classification can be binary (e.g., positive or negative) or have more levels of classification (e.g., a scale from 1 to 10 or 0 to 1). Moreover, the classification, can be expressed as a probability anywhere between "0 percent" (e.g., absence of the particular property) and "100 percent" (e.g., presence of the particular property). Thus, for example, a probability of 67% would indicate a 67% probability that the subject that originated the sample has the condition. The terms "cutoff" and "threshold" can refer to predetermined numbers used in an operation. For example, a cutoff size can refer to a size above which fragments are excluded. A threshold value can be a value above or below which a particular classification applies. Either of these terms can be used in either of these contexts.

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

III. Tumor Organoid Cultures

A. Tumor Organoid Culturing Systems

In one aspect, provided herein is a tumor organoid culturing system. The tumor organoid culturing system includes an organoid culture medium that includes one or more growth factors. In some embodiments, the growth factors are substantially free of R-spondin (e.g., R-spondin1). In addition, the tumor culturing system includes one or more extracellular matrix substitutes. Features of the subject organoid culturing systems are described in further detail below.

1. Organoid Culture Media

The organoid culture media provided herein include one or more organoid growth factors. As used herein, "organoid growth factors" are growth factors that promote the growth and development of tumor organoids in the subject culturing system. Organoid growth factors include an epidermal growth factor (EGF), a fibroblast growth factor (FGF), a hepatocyte growth factor (HGF), a Wnt, Noggin, an R-spondin, Gastrin, Prostaglandin, and Neuregulin. Organoid growth factors include ligands (natural, semi-synthetic, or synthetic, agonist or antagonist) of EGF family receptors, HGF family of receptors, Wnt family receptors, NOTCH family receptors, LRP receptor, Frizzled receptor, LGR5 receptor, insulin receptor, neuregulin family of receptors, or any growth factor receptor tyrosine kinase family member.

Organoid growth factors used in the organoid culture media described herein can be obtained or produced by any suitable technique including, for example, using prokaryotic or eukaryotic expression systems. Organoid growth factors can also be purchased from commercially available sources. See, e.g., Urbischek et al., *Scientific Reports* 9:6193 (2019).

Generally, growth factors included in organoid culture media typically differ among different tumor organoid types and generally include R-spondins (e.g., R-spondin1, Genebank Accession Numbers NP_001033722.1, NP_001229837.1, NP_001229838.1, and NP_001229839.1 (human)). R-spondin family members are secreted agonists of the canonical Wnt/β catenin signaling pathway, most likely as a ligand for Lgr4-6 receptors and an inhibitor for ZNRF3. R-spondins generally include two amino-terminal furin-like repeats, which are necessary and sufficient for Wnt signal potentiation, and a thrombospondin domain that can bind matrix glycosaminoglycans and/or proteoglycans. Lau et al., *Genome Biol.* 13(3):242 (2012). While traditional organoid culture media typically include R-spondin (see, e.g., Tuveson and Clevers Science 364:952-955 (2019). Drost and Clevers. *Nature Reviews Cancer* 18:407-418 (2018)), R-spondin producing cell lines used in the production of such media are not widely available. Further, commercially available purified R-spondin can prove expensive for medium to large-scale application.

In some embodiments, however, the organoid culture media provided herein are substantially free of R-spondin (e.g., R-spondin1). As used herein, "substantially free" with respect to any organoid growth factor in an organoid culture medium means that the organoid growth factor is present at a final concentration of less than 500 ng/ml, 450 ng/ml, 400 ng/ml, 350 ng/ml, 300 ng/ml, 250 ng/ml, 200 ng/ml, 150 ng/ml, 100 ng/ml, 50 nm/ml, 25 ng/ml, 20 ng/ml, 15 ng/ml, 10 ng/ml, 5 ng/ml, 1 ng/ml or is 0 ng/ml. In exemplary embodiments, the organoid culture media includes R-spondin (e.g., R-spondin1) at a final concentration of less than 10 ng/ml. In certain embodiments, the organoid culture medium includes at less than 1 ng/ml. In certain embodiments described herein, tumor organoids cultured in the subject organoid culture media exhibit similar clonal diversity as compared to their source tumor. Such tumor organoids can be used advantageously in studies where maintaining source tumor clonal diversity is important (e.g., drug development and screening).

In some embodiments, the organoid culture media provided herein further include one or more of the following organoid growth factors: Noggin, epidermal growth factor (EGF), a fibroblast growth factor (FGF) (e.g., FGF7 and FGF10) and is substantially free of R-spondins. In exemplary embodiments, the Noggin, EGF and FGF are human Noggin, human EGF, and human FGF. In particular embodiments, these organoid growth factors are recombinantly made.

Epidermal growth factor (EGF) is a member of the EGF family that also includes TGF-alpha, amphiregulin (AR), betacellulin (BTC), epiregulin (EPR), heparin-binding EGF-like growth factor (HB-EGF), epigen, and the neuregulins (NRG)-1 through -6. Members of the EGF family share a structural motif, the EGF-like domain, which is characterized by three intramolecular disulfide bonds that are formed by six similarly spaced conserved cysteine residues. All EGF family members are synthesized as type I transmembrane precursor proteins that may contain several EGF domains in the extracellular region. The mature proteins are released from the cell surface by regulated proteolysis. The 1207 amino acid (aa) human EGF precursor contains nine EGF domains and nine LDLR class B repeats. The mature human protein includes 53 amino acids and is generated by proteolytic excision of the EGF domain proximal to the transmembrane region. EGF is present in various body fluids, including blood, milk, urine, saliva, seminal fluid, pancreatic juice, cerebrospinal fluid, and amniotic fluid. Four ErbB (HER) family receptor tyrosine kinases including EGFR/ErbB1, ErbB2, ErbB3 and ErbB4, mediate responses to EGF family members. These receptors undergo a complex pattern of ligand induced homo- or hetero-dimerization to transduce EGF family signals. EGF binds ErbB1 and depending on the context, induces the formation of homodimers or heterodimers containing ErbB2. Dimerization results in autophosphorylation of the receptor at specific tyrosine residues to create docking sites for a variety of signaling molecules. Biological activities ascribed to EGF include epithelial development, angiogenesis, inhibition of gastric acid secretion, fibroblast proliferation, and colony formation of epidermal cells in culture.

Noggin is a signaling molecule that binds and inactivates ligands of the transforming growth factor-beta (TGF-beta) superfamily (e.g., MBP-2, -4, -7, -13, and -14) of signaling proteins.

Fibroblast growth factors (FGFs) are a family of functional proteins including 22 members. FGFs act at four different types of receptors initiating different tissue processes. FGFs are important in early development, contributing to mesoderm induction, limb development, neural induction and neural development. In mature tissues, FGFs are known to be crucial for angiogenesis, keratinocyte organization, and would healing processes.

As shown in Table 1 below, the exemplary organoid culture media provided herein include one to four growth factors selected from Noggin, EGF and FGF (e.g., FGF7 or FGF10), which is less than many commonly used organoid culture media. For example, Sachs et al., Cell 172:373-86e10 (2018), discloses an organoid culture medium for breast cancer tumor organoids that includes five organoid growth factors and includes R-spondin1. Thus, the organoid culture media provided herein are advantageously cost-effective and alleviate the batch to batch variability associated with organoid growth factor production as compared to traditional organoid culture media, as fewer growth factors are required. Further, tumor organoids cultured in the subject organoid culture media exhibit similar clonal diversity as compared to their source tumor. Such tumor organoids can be used advantageously in studies where maintaining source tumor clonal diversity is important.

In certain embodiments, the organoid growth factors included in the organoid culture medium include Noggin. In particular embodiments, the Noggin is recombinant human Noggin. In some embodiments, Noggin is included in the organoid culture media at a final concentration of at least 10, 20, 30, 40, 50, 60, 70, 80, 90 or 100 µg/ml. In exemplary embodiments, the Noggin is included in the organoid culture media at a final concentration of about 50 µg/ml. In certain embodiments, the organoid growth factors include Noggin and is substantially free of R-spondins. In particular embodiments, the organoid culture medium has less than a final concentration of 10 µg/ml R-spondin. In some embodiments, the organoid culture medium includes Noggin and is substantially free of any additional organoid growth factor, where the additional organoid growth factors are an epidermal growth factor (EGF), a fibroblast growth factor (FGF), a hepatocyte growth factor (HGF), a Wnt, an R-spondin, Gastrin, Prostaglandin, Neuregulin, ligands (natural, semi-synthetic, or synthetic, agonist or antagonist) of EGF family receptors, HGF family of receptors, Wnt family receptors, NOTCH family receptors, LRP receptor, Frizzled receptor, LGR5 receptor, insulin receptor, neuregulin family of receptors, or any growth factor receptor tyrosine kinase family member.

In some embodiments, the organoid growth factors included in the organoid culture medium include a combination of epidermal growth factor (EGF), and Noggin. In particular embodiments, the organoid growth factors are human EGF and human Noggin. In exemplary embodiments, the organoid growth factors are recombinantly made. In some embodiments, Noggin is included in the organoid culture media at a final concentration of at least 10, 20, 30, 40, 50, 60, 70, 80, 90 or 100 µg/ml. In some embodiments, EGF is included in the organoid culture medium at a final concentration of at least 10, 20, 30, 40, 50, 60, 70, 80, 90, 100, 150, 200, 250, or 300 µg/ml. In certain embodiments, the organoid culture medium includes Noggin at a final concentration of about 50 µg/ml and EGF is included at a final concentration of about 200 µg/ml. In exemplary embodiments, the organoid culture medium includes EGF and Noggin and is substantially free of R-spondins. In particular embodiments, the organoid culture medium has less than a final concentration of 10 µg/ml R-spondin. In some embodiments, the organoid culture medium includes EGF and Noggin and is substantially free of any additional organoid growth factor, where the additional organoid growth factors are a fibroblast growth factor (FGF), a hepatocyte growth factor (HGF), a Wnt, an R-spondin, Gastrin, Prostaglandin, Neuregulin, ligands (natural, semi-synthetic, or synthetic, agonist or antagonist) of EGF family receptors, HGF family of receptors, Wnt family receptors, NOTCH family receptors, LRP receptor, Frizzled receptor, LGR5 receptor, insulin receptor, neuregulin family of receptors, or any growth factor receptor tyrosine kinase family member. As described herein, organoid culture media that include Noggin and EGF and are substantially free of R-spondin are useful for culturing tumor organoids derived from squamous cancer, lung cancer, colon cancer, gastric cancer, esophageal cancer, head and neck cancer, and colon cancer.

In other embodiments, the organoid growth factors included in the organoid culture medium includes a combination of EGF, Noggin and one or more fibroblast growth factors (FGFs). In particular embodiments, the FGF is a combination of FGF7 and FGF10. In particular embodiments, the organoid growth factors are human EGF, human Noggin, human FGF7 and human FGF10. In exemplary embodiments, the organoid growth factors are recombinantly made. In some embodiments, Noggin is included in the organoid culture medium at a final concentration of at least 10, 20, 30, 40, 50, 60, 70, 80, 90 or 100 µg/ml. In some embodiments, EGF is included in the organoid culture medium at a final concentration of at least 10, 20, 30, 40, 50, 60, 70, 80, 90, 100, 150, 200, 250, or 300 µg/ml. In certain embodiments, the one or more FGFs (e.g., FGF7 and FGF10) are each included in the organoid culture medium at a final concentration of at least 10, 20, 30, 40, 50, 60, 70, 80, 90 or 100 µg/ml. In exemplary embodiments, the organoid growth factors included in the organoid culture medium includes a combination of EGF, Noggin, FGF7 and FGF10 and is substantially free of R-spondins. In particular embodiments, the organoid culture medium has less than a final concentration of 10 µg/ml R-spondin. In some embodiments, the organoid culture medium includes EGF, Noggin, FGF7 and FGF10 and is substantially free of any additional organoid growth factor, where the additional organoid growth factors are an additional fibroblast growth factor (FGF), a hepatocyte growth factor (HGF), a Wnt, an R-spondin, Gastrin, Prostaglandin, Neuregulin, ligands (natural, semi-synthetic, or synthetic, agonist or antagonist) of EGF family receptors, HGF family of receptors, Wnt family receptors, NOTCH family receptors, LRP receptor, Frizzled receptor, LGR5 receptor, insulin receptor, neuregulin family of receptors, or any growth factor receptor tyrosine kinase family member.

As described herein, organoid culture media that include Noggin, EGF, FGF7 and FGF10 and are substantially free of R-spondin are useful for culturing tumor organoids derived from breast cancer, lung cancer, gastric cancer, colon cancer, esophageal, or liver cancer.

Exemplary combinations of organoid growth factors included in the organoid culture media provided herein are summarized below in Table 1.

TABLE 1

| Exemplary Organoid Culture Medium | Organoid Growth Factors |
| --- | --- |
| B | Noggin |
| C | EGF and Noggin |
| D | EGF, Noggin, FGF7 and FGF10 |

In addition to organoid growth factors, the culture media provided herein can also include one or more additional culture media components. In some embodiments, the organoid culture medium includes a molecular inhibitor such as, for example, a Rho kinase inhibitor, a transforming growth factor-beta inhibitor and/or a MAP kinase inhibitor.

In several embodiments, the organoid culture medium includes a Rho kinase inhibitor (also referred to as "rho-associated protein kinase inhibitor" and "ROCK inhibitor"). Suitable Rho kinase inhibitors useful in the organoid culture media provided herein include, but are not limited to, Y27632, Fasudil, Ripasudil, Netarsudil, RKO-1447, GSK429286 and Y30141. In certain embodiments, the Rho kinase inhibitor is Y27632.

In several embodiments, the organoid culture medium includes a MAP kinase inhibitor. Suitable MAP kinase inhibitors useful in the organoid culture media provided herein include, but are not limited to, SB203580 (Calbiochem, 559389), SB202190 (Axon Medchem, 1364), SB220025 (Sigma, S9070), VX-745 (Philip Cohen, University of Dundee), and BIRB-796 (Axon Medchem, 1358). In exemplary embodiments, the MAP kinase inhibitor is SB202190. For more discussion of these inhibitors, see Menon et al., *Autophagy* 11(8):1425-1427 (2015), which is hereby incorporated by reference.

In some embodiments, the organoid culture medium includes a transforming growth factor-beta inhibitor. In particular embodiments, the transforming growth factor-beta inhibitor is A-83-01. In some embodiments, the transforming growth factor-beta inhibitor is galunisertib, fresolimumab, lucanix, vigil, trabedersen, fresolimumab, or XOMA089. For more information on such inhibitors, see Gramont et al., *Oncoimmunology* 6(1): e1257453 (2017), which is hereby incorporated by reference.

In some embodiments, the organoid culture medium includes a Rho kinase inhibitor, a transforming growth factor-beta inhibitor and a MAP kinase inhibitor. In exemplary embodiments, the organoid culture medium includes the Rho kinase inhibitor Y27632, the MAP kinase inhibitor SB202190, and the transforming growth factor-beta inhibitor A-83-01.

In some embodiments, the organoid culture medium further includes one or more of the following components: a) a chemically-defined, minimal culture medium; b) L-glutamine; c) a serum replacement supplement; d) N-acetyl-L-cysteine; and e) nicotinamide.

In certain embodiments, the organoid culture medium includes a chemically-defined minimal culture medium. Chemically-defined minimal culture medium that can be used in the organoid culture medium provided herein include, for example, Dulbecco's Modified Eagle Medium, Roswell Park Memorial Institute 1640 Medium, Ham's F-12 Medium, or a combination thereof. In exemplary embodiments, the chemically-defined, minimal culture medium is a 1:1 mixture of a Dulbecco's Modified Eagle Medium and a Ham's F-12 medium.

In some embodiments, the organoid culture medium includes a serum replacement supplement. Suitable replacement supplements include, for example, holo-transferrin, insulin, superoxide dismutase, catalase enzyme, carnitine, putrescine, glutathione, galactose, corticosterone, ethanolamine, linoleic acid, linolenic acid, selenite, tri-iodothyronine, tocopherol, or progesterone and combinations thereof. In some embodiments, the serum replacement supplement includes holo-transferrin, insulin, superoxide dismutase, catalase enzyme, carnitine, putrescine, glutathione, galactose, corticosterone, ethanolamine, linoleic acid, linolenic acid, selenite, tri-iodothyronine, tocopherol, and progesterone. In other embodiments, the serum replacement supplement includes insulin and holo-transferrin. Exemplary serum replacement include, for example, B-27, NS-21 and N-2 serum replacement supplement.

a. Useful Organoid Culture Media

Exemplary embodiments of the organoid culture media provided herein are depicted below in Table 2.

TABLE 2

| Organoid Culture Medium | Growth Factors | Molecular Inhibitors | Additional Components |
| --- | --- | --- | --- |
| B | Noggin | Rho kinase inhibitor, transforming growth factor-beta inhibitor, and MAP kinase inhibitor | a chemically-defined, minimal culture medium; L-glutamine; a serum replacement supplement; N-acetyl-L-cysteine; and nicotinamide |
| C | EGF and Noggin | Rho kinase inhibitor, transforming growth factor-beta inhibitor, and | a chemically-defined, minimal culture medium; L-glutamine; a serum replacement supplement; N-acetyl-L-cysteine; and nicotinamide |

TABLE 2-continued

| Organoid Culture Medium | Growth Factors | Molecular Inhibitors | Additional Components |
|---|---|---|---|
| D | EGF, Noggin, FGF7 and FGF10 | MAP kinase inhibitor Rho kinase inhibitor, transforming growth factor-beta inhibitor, and MAP kinase inhibitor | a chemically-defined, minimal culture medium; L-glutamine; a serum replacement supplement; N-acetyl-L-cysteine; and nicotinamide |

In exemplary embodiments, the Rho kinase inhibitor referred to in Table 2 is Y27632, the transforming growth factor-beta inhibitor referred to in Table 2 is A-83-01, and the MAP kinase inhibitor referred to in Table 2 is SB202190.

In some embodiments, the chemically-defined, minimal culture medium of the organoid culture media depicted in Table 2 is Dulbecco's Modified Eagle Medium, Roswell Park Memorial Institute 1640 Medium, Ham's F-12 Medium, or a combination thereof. In exemplary embodiments, the chemically-defined, minimal culture medium in the organoid culture media depicted in Table 2 is 1:1 mixture of a Dulbecco's Modified Eagle Medium and a Ham's F-12 medium.

In exemplary embodiments, the serum replacement supplement of the organoid culture media depicted in Table 2 includes holo-transferrin, insulin, superoxide dismutase, catalase enzyme, carnitine, putrescine, glutathione, galactose, corticosterone, ethanolamine, linoleic acid, linolenic acid, selenite, tri-iodothyronine, tocopherol, or progesterone and combinations thereof. In some embodiments, the serum replacement supplement includes holo-transferrin, insulin, superoxide dismutase, catalase enzyme, carnitine, putrescine, glutathione, galactose, corticosterone, ethanolamine, linoleic acid, linolenic acid, selenite, tri-iodothyronine, tocopherol, and progesterone. In other embodiments, the serum replacement supplement includes insulin and holo-transferrin. In exemplary embodiments, the serum replacement supplement of the organoid culture media depicted in Table 2 is B-27 serum replacement supplement.

Additional useful organoid culture media formulations are included in Example 2.

2. Extracellular Matrix (ECM) Components

In addition to the organoid culture media provided herein, the subject organoid culture systems can optionally include one or more extracellular matrix (ECM) components that function as a substrate for culturing the tumor organoid in the culture system. The ECM includes a large collection of biochemically distinct components include, for example, glycoproteins, proteoglycans and polysaccharides with different physical and biochemical properties. The ECM is a charged protein network rich in polysaccharide modifications and can bind to many growth factors. ECM matrix components can regulate various cellular processes, such as gene expression, differentiation, and proliferation. Preferably, the ECM components included in the subject culture system function as a substrate that supports the growth and development of tumor organoids. Moreover, the ECM components used are preferably free of growth factors other than those that are included in the organoid culture medium used. In some embodiments, the extracellular matrix components included in the organoid culture system includes recombinant collagen, laminin, fibronectin, and/or gelatin or combinations thereof. In certain embodiments, the extracellular matrix substitute includes a basement membrane extract. In exemplary embodiments, the extracellular matrix substitute is a Matrigel.

B. Tumor Organoid Culturing Methods

In another aspect, provided herein are methods for culturing tumor organoids using the subject organoid culture media and organoid culture systems provided herein. Tumor tissue is first obtained from a source cancer and the tumor tissue is subsequently dissociated into a plurality of dissociated tumor cells. Tumor tissues used in the culturing methods can be obtained from a variety of source cancers including, but are not limited to, an anal cancer, a basal cell skin cancer, a squamous cancer, a breast cancer, a bladder cancer, a cervical cancer, a colon cancer, an endometrial cancer, a head and neck cancer, a hepatobiliary cancer, a kidney cancer, a gastric cancer, a lung cancer, a mesothelial cancer of the pleural cavity, a mesothelial cancer of the peritoneal cavity, an ovarian cancer, prostate cancer, or a rectal cancer. In some embodiments, the source cancer is obtained from a human. In embodiments, where the tumor organoid is used for the development of personalized treatment for a particular subject, the source cancer is obtained from the same subject. Tumor tissue samples can be obtained by any suitable method including, for example, from a patient biopsy.

The tumor tissue is subsequently dissociated into a plurality of dissociated tumor cells. Any suitable method can be used to dissociate the tumor tissue including the dissociation methods described in the examples provided herein. In some embodiments, the tumor tissue is mechanically broken into small fragments that are subsequently washed and undergo enzymatic digestion in an enzymatic digestion buffer. In certain embodiments, the enzymatic digestion buffer includes a collagenase (e.g., collagenase type II or IV) and/or trypsin. Following dissociation the dissociated cells are washed and seeded in the subject organoid culture system provided herein.

In some embodiments, the dissociated tumor cells are seeded and cultured in an organoid culture system that includes an organoid culture medium with any of the organoid growth factors in Table 1. The organoid culture medium used is substantially free of R-spondins (e.g., R-spondin1). In one embodiment, the dissociated cells are seeded in an organoid culture system that includes Noggin and is substantially free of R-Spondin1. In certain embodiments, the dissociated cells are seeded in an organoid culture system that includes EGF and Noggin and is substantially free of R-Spondin1. In other embodiments, the dissociated cells are seeded in an organoid culture system that includes EGF, Noggin, and one or more fibroblast growth factors (FGF) and is substantially free of R-Spondin1. In particular embodiments, the one or more fibroblast growth factors are FGF7 and FGF10. In some embodiments, the dissociated tumor cells are seeded in an organoid culture system that includes any of the organoid culture media set forth in Table 2 or Example 2.

The dissociated cells can be cultured in the organoid culture system for any suitable time period to allow for the formation of tumor organoids. In some embodiments, the cells are cultured for at least 1, 2, 3, 4, 5, 6, 7, 8, 9, 10, 11, 12, 16, 18 or 24 hours. In certain embodiments, the cells are culture for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days. In exemplary embodiments, the cells are cultured for about 14 days.

In some embodiments, an optimal organoid culture medium for culturing tumor organoids from a particular source tumor is determined. In such embodiments, the dissociated cells from a source tumor are cultured in two or more of the subject organoid culture media provided herein. The cells are cultured for a set time period to allow for tumor organoid formation, e.g., 14 days, and the cultures are examined for tumor organoid formation. In some embodiments, the cells are cultured for at least 1, 2, 3, 4, 5, 6, 7, 8, 9, 10, 11, 12, 16, 18 or 24 hours. In certain embodiments, the cells are culture for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days. In some embodiments, the tumor organoids formed are tested for one or more additional properties to ensure that the tumor organoid cultured in a particular medium recapitulates the property of the source tumor (e.g., clonal diversity, gene expression, etc.). An optimal medium is selected based on the assessment of tumor organoid formation and the one or more properties examined.

Any suitable culture vessel can be used for the culturing of the tumor organoids. Appropriate culture vessels include, but are not limited to, a tissue culture plate, such as a flask, 6-well, 24-well, or 96-well plate. a flask, a Petri dish, a multi dish, a micro plate, a micro-well plate, a multi plate, a multi-well plate, a micro slide, a chamber slide, a tube, and a tray. The cells may be cultured in a volume of at least or about 0.2, 0.5, 1, 2, 5, 10, 20, 30, 40, 50 ml, 100 ml, 150 ml, 200 ml, 250 ml, 300 ml, 350 ml, 400 ml, 450 ml, 500 ml, 550 ml, 600 ml, 800 ml, 1000 ml, 1500 ml, or any range derivable therein, depending on the needs of the culture. In some embodiments, the dissociated cells are cultured using a scaffold free system that rely on cell-cell interactions. Exemplary scaffold-free methods for culturing include, for example, hang-drop, liquid overlay and spinner flask methods. See, e.g., Eder and Eder, *Methods Mol. Biol.* 1612:167-175 (2017). In some embodiments, the culturing is performed using a microfluidic system, such as a microfluidic chip, wherein the organoid culture medium is released using desired flow rates via microchannels. See, e.g., Bein et al., *Cellular and Molecular Gastroenterology and Hepatology* 5(4):659-668 (2018).

Following tumor organoid formation, the tumor organoid can be evaluated for one or more desired properties to ensure that it recapitulates the source tumor with respect to the more properties. In some embodiments, tumor heterogeneity of the tumor organoid is assessed and compared to the heterogeneity of the source tumor. In some embodiments, the property evaluated is cellular morphology, gene expression, metabolism, motility, proliferation, or metastatic potential. In exemplary embodiments, the clonal diversity of the tumor organoid is assessed and compared to the clonal diversity of the source tumor. Methods of assessing clonal diversity are discussed in further detail below.

In some embodiments, expression of one or more genes is assessed and compared with the source tumor. In particular embodiments, the tumor organoid is assessed for enrichment of a particular gene transcript set (an organoid transcript profile) known to be known to be enriched in a particular tumor type as depicted, for example, in a tumor transcript profile. Transcript profiles can be obtained using any suitable method known in the art, include methods described herein. In some embodiments, transcript profiles (e.g., organoid or tumor transcript profiles) are compiled using DNA microarray or RNA-Seq data. In some embodiments, the tumor organoid is considered similar to the source tumor if the organoid transcript profile satisfies a threshold level of similarity with the tumor transcript profile for the tumor type. In certain embodiments, a threshold level of similarity is a threshold concordance between the organoid transcript profile for the tumor organoid and the tumor transcript profile for the tumor type. In some embodiments, this threshold level of similarity is at least 30, 35, 40, 45, 50, 55, 60, 65, 70, 75, 80, 85, 90, 95, or 99 percent similarity. In certain embodiments, such an analysis is performed using gene set enrichment analysis (GSEA). See, e.g., Subramanian et al., *Proc Natl Acad Sci USA* 102(43):15545-15550 (2005); and Mootha et al. *Nature Genetics* 34(3):267-273 (2003), which is hereby incorporated by reference herein.

The tumor organoid can be used for any suitable application as described herein or maintained in culture media by passaging the tumor organoid cell line. Tumor organoids are passaged by removing the tumor organoids from the organoid culture system and mechanically disrupting the tumor organoids to obtain smaller aggregates or single cells. The cells are subsequently washed and single cells or tumor organoid are plated in a new culture vessel. Tumor organoids produced using the culture methods provided herein may also be cryopreserved and deposited in an organoid biobank for use in future studies. See, e.g., Yan et al., *Cell Stem Cell* 23(6):882-897 (2018). Cells can be passaged 1, 2, 3, 4, 5, 6, or 7 days or 1, 2, 3, or 4 weeks after culturing. In exemplary embodiments, the tumor organoids are passaged 1-2 weeks after culturing. In preferred embodiments, the tumor organoids are passaged 2 weeks after culturing.

C. Clonal Diversity Assessment

Tumor organoids developed using the subject methods provide powerful cancer research tools as these organoids maintain properties of the original tumor source. Several techniques can be used to ensure that the tumor organoids developed using the subject methods is representative of the original tumor source.

"Clonal diversity" refers to the different cell clones present within a defined population (e.g., a plurality of cells, a tumor or tumor organoid, a subject or a plurality of subjects) due, at least in part, to the somatic variants that arise during cell division. In cancers, somatic variants accumulate in different populations of cells during clonal expansion over the course of disease, thereby creating a mixture of cancer cell clones in the tumor with genetic and morphological heterogeneity. Tumor clonal diversity can arise due to random mutations that occur during cell divisions of cancer cells or through mutational events stimulated by various exposures.

While a few clones may dominate the composition of a tumor, minor subclones can determine the clinical course of disease progression and recurrence. See, e.g., Landau et al., *Cell* 152(4):714-726 (2013); Maley et al., *Nat Genet.* 38:468-73 (2006): Chowell et al., *Genome Biol.* 17:1-4 (2016); and Bozic et al., *Proc Natl Acad Sci USA* 111: 15964-8 (2014). Several studies have shown that there is a clear association between a greater number of detectable subclonal populations and poorer clinical outcome in lower grade glioma, and cancers of the prostate, kidney, head and neck, breast, and lung. See, e.g., Zhang et al., *Science* 346:256-9 (2014); Andor et al., *Nat Med.* 22:105-113 (2015); and Pereira et al., *Nat Commun.* 7:11479 (2016).

Clonal heterogeneity contributes to drug resistance; anticancer treatments can act as a strong selective pressure and drive the emergence of drug-resistant subclones that allow the tumor to persist. For example, several studies of cancer patients who have lapsed, revealed that tumor cells in the relapsed-associated clone were often present as undetected subclones in the primary tumor before the initiation of therapy, suggesting that driver mutations in these subclonal populations are selected for during therapy.

Thus, a tumor organoid that recapitulates the clonal diversity of its source tumor advantageously provides a tool for the development of anti-cancer therapies and personalized treatment regimens.

In some embodiments, the subject tumor organoid exhibits similar clonal diversity to its source tumor. See Example 3. Such tumor organoids can be used for applications where recapitulation of the clonal diversity of its source tumor is important such as, for example, drug development as well as drug screening, where different combinations and/or concentrations of drugs are applied to a plurality of tumor organoids in order to identify combinations and/or concentrations that may be therapeutically effective to a patient with cancer from which the tumor organoids were derived. The subject tumor organoids can also be used as models for understanding changes in tumor clonal diversity over time and the effects of particular agents (e.g., pathogens and environmental agents) on tumor clonal diversity in a controlled in vitro environment.

Figure 3:
FIG. 3 provides a flow chart of processes and features for evaluating the clonal diversity of a cancer in a subject, in accordance with some embodiments of the present disclosure, in accordance with some embodiments of the present disclosure.
Figure 4:
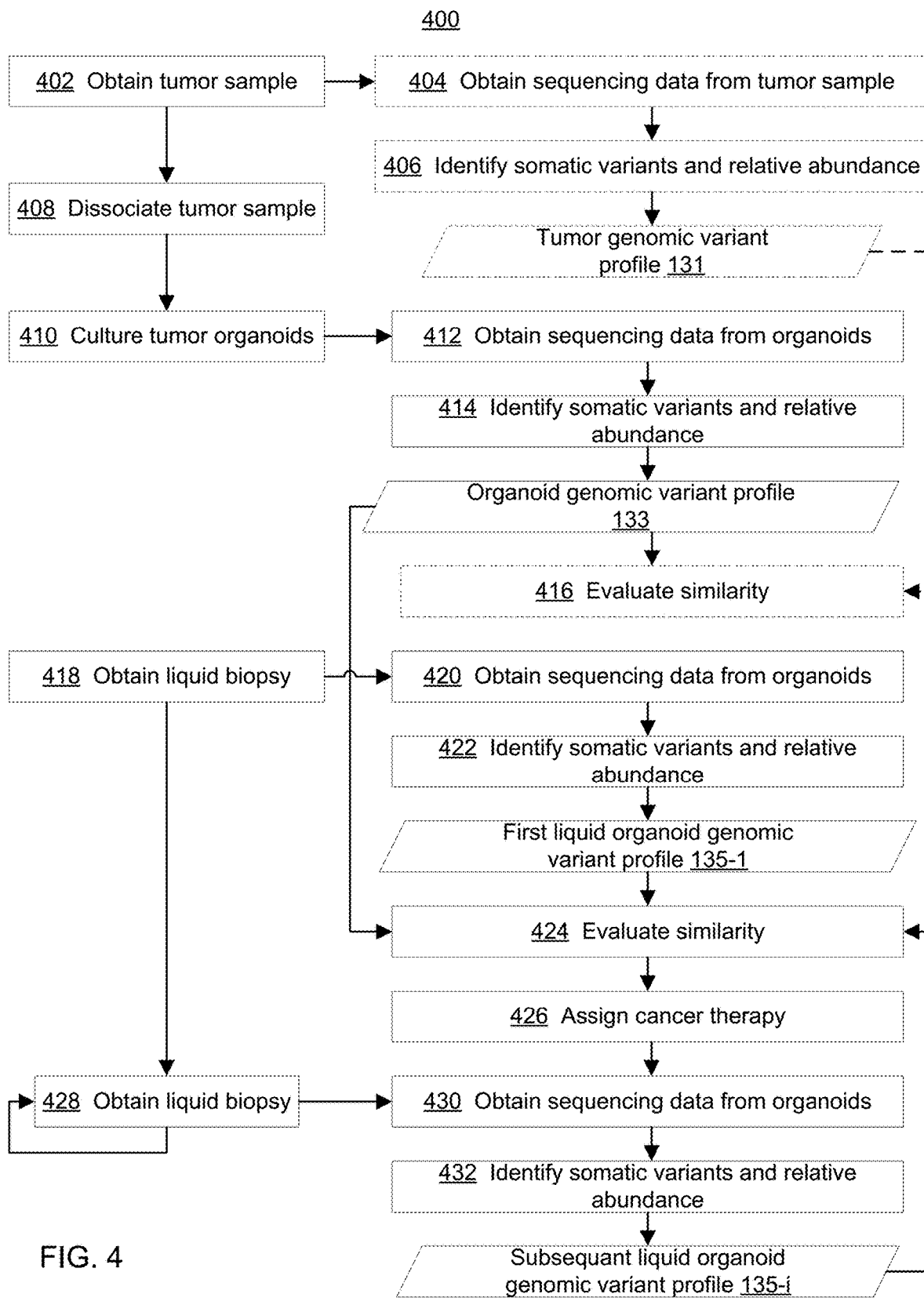
FIG. 4 provides a flow chart of processes and features for evaluating the clonal diversity of a cancer in a subject, in accordance with some embodiments of the present disclosure, in accordance with some embodiments of the present disclosure.

Any suitable method can be used to assess clonal diversity. In particular applications, where tumor organoids having clonal diversity similar to its source tumor is desired, a comparison of the clonal diversity of the tumor organoid cell line and its source tumor is first made. FIG. 3 depicts an exemplary method for making such a comparison.

As shown in FIG. 3, a genomic variant profile (131) of a reference (e.g., a source tumor or a liquid biopsy from the subject of the source tumor) is first determined. In some embodiments, the genomic variant profile (131) is determined by obtaining sequencing data from the reference (e.g., source tumor (304) or liquid biopsy) and identifying a plurality of somatic variants and relative abundance values for each of the somatic variants (306) in the plurality. Next, an organoid genomic variant profile (133-1) of the tumor organoid cell line is determined. The first organoid genomic variant profile is determined by obtaining sequencing data from the tumor organ cell line (322) and identifying somatic variants and relative abundance values for the somatic variants (324). Similarities and/or differences between the reference genomic variant profile and the first organoid genomic variant profile are then evaluated (316).

In some embodiments, transcriptomic and/or epigenetic data can be used to assess clonal diversity in combination with genomic variant profiles. Transcriptomic and/or epigenetic data are particularly useful in instances when there are there is a paucity of somatic mutations associated with a particular tumor and, therefore, genomic variant profiles provide limited information. In some instances, known variant transcripts (e.g., fusion or isoform variants) or epigenetic modifications (e.g., DNA methylation patterns, open chromatin modifications and/or histone modifications) associated with a particular subclone can assist in identifying the subclone in a sample, and resolve an evolutionary timeline of genomic events when characterizing the diversity of the tumor's growth.

In some embodiments, clonal diversity is determined by comparing transcript profiles of the reference and the tumor organoid. In such an embodiment, a transcript profile of a reference (e.g., a source tumor or a liquid biopsy from the subject of the source tumor) is first determined. In some embodiments, the transcript profile is determined by obtaining sequencing data from the reference (e.g., source tumor or liquid biopsy) and identifying a plurality of transcripts and relative abundance values for each of the transcripts in the plurality. Next, an organoid transcript profile of the tumor organoid cell line is determined. The first organoid transcript profile is determined by obtaining sequencing data from the tumor organ cell line and identifying transcripts and relative abundance values for the transcripts. Similarities and differences between the reference transcript profile and the first organoid transcript profile are then evaluated. As there are many copies of transcripts in a given sample as compared to genomic DNA, transcript profiles are sometimes more easy to construct as compared to variant genomic profiles.

In some embodiments, epigenetic information is also used to compliment or validate clonal diversity inferences based on genomic variant and/or transcript profiles. In some embodiments, clonal diversity is assessed at least in part by comparing epigenetic features such as DNA methylation patterns, open chromatin modifications and/or histone modifications (e.g., methylation, ubiquination, SUMOylation, ADP-ribosylation, deamination and proline isomerization) between the source tumor sample and tumor organoid cell line. Epigenetic profiles can be obtained using, but not limited to using techniques such as, bisulfite conversion (methylation), ATA-seq (open chromatin modifications) and CHIP-seq (histone modification) techniques. Epigenetic information is particularly useful for assessing clonal diversity in instances where transcript variants and/or somatic mutations associated with the tumor are uncommon (e.g., squamous carcinomas).

1. Genomic Variant Profiles and Transcript Profiles

In some embodiments, clonal diversity is assessed based on genomic variant profiles that include information relating to the presence and/or frequency of a plurality of somatic variants present in a particular genome. In certain embodiments, genomic variant profiles for a reference (e.g., a source tumor or liquid biopsy from the subject of the source tumor) and the tumor organoid cell line are determined. In some embodiments, a genomic variant profile includes allelic information relating to at least 2, 5, 10, 15, 20, 25, 30, 35, 40, 45, 50, 55, 60, 65, 75, 80, 85, 90, 95, 100, 150, 200, 250, 300, 350, 400, 450, 500 gene loci of interest. In some embodiments, a genomic variant profile includes somatic variant information relating to at least $1 \times 10^3$, $1 \times 10^4$, $1 \times 10^5$, $1 \times 10^6$, $1 \times 10^7$, $1 \times 10^8$, $1 \times 10^9$, or $3 \times 10^9$ gene loci of interest.

In some embodiments, the genomic variant profile includes information relating to the presence or absence for each of the somatic variants in a plurality of somatic variants. In exemplary embodiments, the genomic variant profile includes information relating to the frequency for each of the somatic variants in a plurality of somatic variants. In particular embodiments, the frequency is expressed as variant allelic frequency (VAF). VAF is determined as the percentage of sequence reads observed matching a specific nucleic acid variant (e.g., somatic variant) divided by the overall coverage at the particular locus.

In some embodiments, clonal diversity is assessed based on transcript profiles that include information relating to the presence and/or frequency of a plurality of transcripts (e.g., single nucleotide variants, fusions, splice variants, and/or isoform variants) in a particular transcriptome. In certain embodiments, transcript profiles for a reference (e.g., a source tumor or liquid biopsy from the subject of the source tumor). and the tumor organoid cell line are determined. In some embodiments, a transcript profile includes allelic information relating to at least 2, 5, 10, 15, 20, 25, 30, 35, 40, 45, 50, 55, 60, 65, 75, 80, 85, 90, 95, 100, 150, 200, 250, 300, 350, 400, 450, 500 transcripts of interest. In some embodiments, a genomic variant profile includes somatic variant information relating to at least $1\times10^3$, $1\times10^4$, or $1\times10^5$ transcripts.

Genomic variant profiles are determined for the reference (e.g., source tumor or liquid biopsy) and the tumor organoid cell line using sequencing data that is used to identify a plurality of somatic variants for each of the source tumor and the tumor organoid cell line. Transcript profiles are also similarly determined for the reference (e.g., source tumor or liquid biopsy) and the tumor organoid cell line using sequencing data (e.g., from mRNA or cDNA intermediates).

Sequencing data may be obtained from nucleic acids from the source tumor and tumor organoid cell line or from intermediates (e.g., cDNA or amplicons). For the source tumor, nucleic acids can be obtained from a plurality of cells from a sample of the source tumor. In some embodiments, the cells are obtained from a biopsy of the source tumor. In some embodiments, the sample includes different regions of the source tumor. In some embodiments, the source tumor includes a plurality of tumors from the subject. As explained below, in some embodiments, the nucleic acids for the reference are not obtained from the source tumor, but from a liquid biopsy (e.g., cell-free DNA such as circulating tumor DNA). Liquid biopsies that include circulating tumor DNA (ctDNA) allow for assessment of clonal diversity across all tumors throughout a subject, as opposed to clonal diversity of a single tumor. Thus, subject tumor organoids that exhibit similar clonal diversity to the liquid biopsy can provide a useful tool for ascertaining therapeutic response in the subject as a whole.

For tumor organoid genomic variant profiles and transcript profiles, nucleic acids used include nucleic acids isolated direct from a plurality of tumor organoids in the tumor organoid cell line or from cell-free DNA obtained from the organoid culture media in which the tumor organoid cell line is cultured. Using nucleic acids obtained from organoid culture media allows tumor organoids in the cell line to remain undisturbed. These tumor organoids can then be used for other purposes following the clonal diversity assessment (e.g., drug development).

Methods for obtaining nucleic samples of cancerous tissue are known in the art, and are dependent upon the type of cancer being sampled. For example, bone marrow biopsies and isolation of circulating tumor cells can be used to obtain samples of blood cancers, endoscopic biopsies can be used to obtain samples of cancers of the digestive tract, bladder, and lungs, needle biopsies (e.g., fine-needle aspiration, core needle aspiration, vacuum-assisted biopsy, and image-guided biopsy, can be used to obtain samples of subdermal tumors, skin biopsies, e.g., shave biopsy, punch biopsy, incisional biopsy, and excisional biopsy, can be used to obtain samples of dermal cancers, and surgical biopsies can be used to obtain samples of cancers affecting internal organs of a patient. In some embodiments, the source tumor is a solid biopsy. In some embodiments, the biological sample comprises blood or saliva. In some embodiments, the subject has cancer.

Similarly, methods for isolating nucleic acids from biological samples are known in the art, and are dependent upon the type of nucleic acid being isolated, e.g., DNA or RNA, and the type of sample from which the nucleic acids are being isolated. For instance, many techniques for DNA isolation, e.g., genomic DNA isolation, from a tissue sample are known in the art, such as organic extraction, silica adsorption, and anion exchange chromatography. Likewise, many techniques for RNA isolation, e.g., mRNA isolation, from a tissue sample are known in the art. For example, acid guanidinium thiocyanate-phenol-chloroform extraction (see, for example, Chomczynski and Sacchi, *Nat Protoc,* 1(2):581-85 (2006), which is hereby incorporated by reference herein), and silica bead/glass fiber adsorption (see, for example, Poeckh, T. et al., *Anal Biochem.* 373(2):253-62 (2008), which is hereby incorporated by reference herein). The selection of any particular DNA or RNA isolation technique for use in conjunction with the embodiments described herein is well within the skill of the person having ordinary skill in the art, who will consider the tissue type, the state of the tissue, e.g., fresh, frozen, etc. and the type of nucleic acid analysis that is to be performed.

In some embodiments, the isolated nucleic acids from the reference (e.g., source tumor) and the tumor organoid cell line are enriched for target sequences associated with cancer classification. Advantageously, enriching for target sequences prior to sequencing the nucleic acids significantly reduces the costs and time associated with sequencing, facilitates multiplex sequencing by allowing multiple samples to be mixed together for a single sequencing reaction, and significantly reduces the computation burden of aligning the resulting sequence reads, as a result of significantly reducing the total amount of nucleic acids analyzed from each sample. Accordingly, in some embodiments, the isolated nucleic acids are hybridized to a probe set, where the probe set includes a plurality of nucleic acid probes for a plurality of human genomic loci of interests.

Generally, the probes include DNA, RNA, or a modified nucleic acid structure with a base sequence that is complementary to loci of interest. Accordingly, when the probe is designed to hybridize to an mRNA molecule isolated from the biological sample, the probe will include a nucleic acid sequence that is complementary to the coding strand of the gene from which the transcript originated, e.g., the probe will include an antisense sequence of the gene. However, when the probe is designed to hybridize to a loci in a gDNA molecule or cDNA molecule, the probe can contain either a sequence that is complementary to either strand, because the molecules in the gDNA or cDNA library are double stranded. In some embodiments, each probe in the plurality of probes includes a nucleic acid sequence that is identical or complementary to at least 15 consecutive bases of a loci of interest. In some embodiments, each probe in the plurality of probes includes a nucleic acid sequence that is identical or complementary to at least 20, 25, 30, 40, 50, 75, 100, 150, 200, or more consecutive bases of a loci of interest.

In some embodiments, the probes include additional nucleic acid sequences that do not share any homology to the loci of interest. For example, in some embodiments, the probes also include nucleic acid sequences containing an identifier sequence, e.g., a unique molecular identifier (UMI), e.g., that is unique to a particular sample or subject. Examples of identifier sequences are described, for example, in Kivioja et al., *Nat. Methods* 9(1):72-74 (2011) and Islam et al., Nat. Methods 11(2):163-66 (2014), which are incorporated by reference herein. Similarly, in some embodiments, the probes also include primer nucleic acid sequences useful for amplifying the nucleic acid molecule of interest, e.g., using PCR. In some embodiments, the probes also include a capture sequence designed to hybridize to an anti-capture sequence for recovering the nucleic acid molecule of interest from the sample.

Likewise, in some embodiments, the probes each include a non-nucleic acid affinity moiety covalently attached to nucleic acid molecule that is complementary to the loci of interest, for recovering the nucleic acid molecule of interest. Non-limited examples of non-nucleic acid affinity moieties include biotin, digoxigenin, and dinitrophenol. In some embodiments, the probe is attached to a solid-state surface or particle, e.g., a dip-stick or magnetic bead, for recovering the nucleic acid of interest. In some embodiments, the methods described herein include amplifying the nucleic acids that bound to the probe set prior to further analysis, e.g., sequencing. Methods for amplifying nucleic acids, e.g., by PCR, are well known in the art.

In some embodiments, particular target sequences from the reference (e.g., source tumor or liquid biopsy) and the tumor organoid cell line are enriched for target sequences associated with cancer classification by amplification, using specific primer pairs designed to amplify the target sequences. In such embodiments, amplicons of the target sequences are subsequently sequenced and the sequencing data is used to derive the genomic variant profile for the source tumor or tumor organoid cell line.

The human genomic loci can include gene loci, e.g., exon or intron loci, as well as non-coding loci, e.g., regulatory loci and other non-coding loci, which have been found to be associated with cancer. Each genomic variant profile includes relative abundance values for a plurality of somatic variants found a plurality of human genomic loci. In some embodiments, the plurality of human genomic loci include at least 5, 10, 15, 20, 25, 50, 100, 150, 200, 250, 300, 350, 400, 500, 750, 1000, 2500, 5000, or more human genomic loci. In one embodiment, the plurality of human genomic loci include at least fifty human genomic loci.

In some embodiments, the genomic variant profile/transcript profile obtained for the reference (e.g., source tumor or liquid biopsy sample) and the tumor organoid cell line include obtaining a plurality of sequence reads, in electronic form, of nucleic acids from the source tumor and tumor organoid, respectively, or intermediates of such nucleic acids (e.g., cDNA and amplicons of enriched DNA or RNA). In some embodiments, the sequence reads are obtained from a nucleic acid sample that has been enriched for target sequences, as described above. Advantageously, as described above, sequencing a nucleic acid sample that has been enriched for target nucleic acids, rather than all nucleic acids isolated from a biological sample, significantly reduces the average time and cost of the sequencing reaction. Accordingly, in some embodiments, the method includes obtaining a plurality of sequence reads (e.g., sequence reads 128) of the nucleic acid hybridized to the probe set, e.g., as described above.

In some embodiments, the sequence reads have an average length of at least fifty nucleotides. In other embodiments, the sequence reads have an average length of at least 25, 30, 35, 40, 45, 50, 60, 70, 80, 90, 100, 150, or more nucleotides. In some embodiments, the sequence reads have an average length of less than 500, 450, or 400 nucleotides. In some embodiments the sequence reads have an average length of between 25 and 1000 nucleotides. In some embodiments the sequence reads have an average length of between 400 and 800 nucleotides.

In some embodiments, the plurality of sequence reads are DNA sequence reads. That is, the nucleic acids isolated from the biological sample are DNA molecules, e.g., genomic DNA (gDNA) molecules or fragments (such as cell-free DNA) thereof.

In some embodiments, the plurality of sequence reads are RNA sequence reads. That is, the nucleic acids isolated from the biological sample are RNA molecules, e.g., mRNA. In some embodiments, RNA sequence reads are obtained directly from the isolated RNA, e.g., by direct RNA sequencing. Methods for direct RNA sequencing are well known in the art. See, for example, Ozsolak et al., *Nature* 461:814-18 (2009), and Garalde et al., *Nat Methods,* 15(3): 201-206 (2018), which are incorporated by reference herein.

In other embodiments, RNA sequence reads are obtained through a cDNA intermediate. Accordingly, in some embodiments, the isolated RNA is used to create a cDNA library via cDNA synthesis. In some embodiments, both for direct RNA sequencing and prior to cDNA library construction, the isolated RNA is first enriched for a desired type of RNA (e.g., mRNA) or species (e.g., specific mRNA transcripts), prior to cDNA library construction.

Methods of enriching for desired RNA molecules are also well known in the art. For example, mRNA molecules can be enriched, e.g., relative to other RNA molecules in a total RNA preparation, using oligo-dT affinity techniques (see, e.g., Rio et al., *Cold Spring Harb Protoc.,* 2010(7) (2010), which is incorporated by reference herein). Specific mRNA transcripts can also be isolated, e.g., using hybridization probes that specifically bind to one or more mRNA sequences of interest.

cDNA library construction from isolated mRNAs is also well known in the art. In some embodiments, cDNA library construction is performed by first-strand DNA synthesis from the isolated mRNA using a reverse transcriptase, followed by second-strand synthesis using a DNA polymerase. Example methods for cDNA synthesis are described in McConnell and Watson, *FEBS Lett.* 195(1-2):199-202 (1986); Lin and Ying, Methods Mol Biol. 221:129-143 (2003), and Oh et al., Exp Mol Med. 35(6):586-90 (2003), which are incorporated by reference herein.

Methods for mRNA sequencing are well known in the art. In some embodiments, the mRNA sequencing is performed by whole exome sequencing (WES). Generally, WES is performed by isolating RNA from a tissue sample, optionally selecting for desired sequences and/or depleting unwanted RNA molecules, generating a cDNA library, and then sequencing the cDNA library, for example, using next generation sequencing (NGS) techniques. For a review of the use of whole exome sequencing techniques in cancer diagnosis, see, Serrati et al., *Onco Targets Ther.* 9: 7355-7365 (2016), which is incorporated by reference herein.

RNA-Seq is a methodology used for RNA profiling based on next-generation sequencing that enables the measurement and comparison of gene expression patterns across a plurality of subjects. In some embodiments, millions of short strings, called 'sequence reads,' are generated from sequencing random positions of cDNA prepared from the input RNAs that are obtained from tumor tissue of a subject. These reads can then be computationally mapped on a reference genome to reveal a 'transcriptional map', where the number of sequence reads aligned to each gene gives a measure of its level of expression (e.g., abundance). Next-generation sequencing is disclosed in Shendure, *Nat. Biotechnology*

26:1135-1145 (2008), which is incorporated by reference herein. RNA-Seq is disclosed in Nagalakshmi et al., *Science* 320:1344-1349 (2008); and Finotell and Camillo, *Briefings in Functional Genomics* 14(2):130-142 (2014), which are incorporated by reference herein. Briefly, RNA molecules isolated from a biological sample are initially fragmented and reverse-transcribed into complementary DNAs (cDNAs). The obtained cDNAs are then amplified and subjected to next-generation DNA sequencing (NGS). In principle, any NGS technology can be used for RNA-Seq. In some embodiments, the Illumina sequencer (see the Internet at illumina.com) is used. See, Wang et al., *Nat Rev Genet.* 10(1):57-63 (2009), which is incorporated by reference herein. The millions of short reads generated for each such sample are then mapped on a reference genome and the number of reads aligned to each gene, called 'counts', gives a digital measure of gene expression levels in the sample under investigation.

Methods for next generation sequencing, which can be used for either DNA or RNA sequencing, are well known in the art. These include sequencing-by-synthesis technology (Illumina), pyrosequencing (454 Life Sciences), ion semiconductor technology (Ion Torrent sequencing), single-molecule real-time sequencing (Pacific Biosciences), sequencing by ligation (SOLiD sequencing), nanopore sequencing (Oxford Nanopore Technologies), or paired-end sequencing. In some embodiments, massively parallel sequencing is performed using sequencing-by-synthesis with reversible dye terminators.

In some embodiments where genomic variant profiles are used, somatic variants to be included in the reference (e.g., source tumor or liquid biopsy) and tumor organoid genomic variant profiles are identified in each of the sequencing data from the reference (e.g., source tumor or liquid biopsy) and tumor organoid cell line, respectively. Somatic variants include, but are not limited to, single nucleotide variants, point mutations, nonsense mutations, frame shift, deletions, duplications, insertions (e.g., in frame insertions), missense mutation, repeat expansion, InDels, exon duplications, fusions, translocations and splice region mutations. In some embodiments, a genomic variant profile includes at least 1, 2, 5, 10, 15, 20, 25, 30, 35, 40, 45, 50, 55, 60, 65, 75, 80, 85, 90, 95, 100, 150, 200, 250, 300, 350, 400, 450, 500 identified somatic variants. In exemplary embodiments, the genomic variant profiles include somatic variants that are identified as driver mutations.

In some embodiments where transcript profiles are used, transcripts to be included in the reference (e.g., source tumor or liquid biopsy) and tumor organoid transcript profiles are identified in each of the sequencing data from the reference (e.g., source tumor or liquid biopsy) and organoid cell line, respectively. In some embodiments, the transcript profiles include information related to the presence and/or amount of one or more identified transcript (e.g., single nucleotide variants, fusions, splice variants, and/or isoform variants). In some embodiments, a transcript profile includes at least 1, 2, 5, 10, 15, 20, 25, 30, 35, 40, 45, 50, 55, 60, 65, 75, 80, 85, 90, 95, 100, 150, 200, 250, 300, 350, 400, 450, 500, $1 \times 10^3$, $1 \times 10^4$, or $1 \times 10^5$ identified transcripts.

In particular embodiments, relative abundance values are determined for each of the somatic variants included in the genomic variant profile or transcripts included in the transcript profile. As used here, a "relative abundance value" with respect to a particular somatic variant refers to the relative amount of a somatic variant at a particular gene locus in a defined population (e.g., a cell, plurality of cells, a patient, or a patient population). Similarly, "relative abundance value" with respect to a particular transcript refers to the relative amount of a transcript in a defined population (e.g., a cell, plurality of cells, a patient, or a patient population). The relative abundance value can be expressed in a binary manner (e.g., present or absent from the sample population) or as a fraction or percentage of the total (e.g., somatic variants at the gene locus or transcripts) in the defined population. In some embodiments, the relative abundance value for the somatic variant is the variant allele frequency (VAF), i.e., the percentage of sequence reads observed matching a specific DNA variant divided by the overall coverage at that locus.

In instances where nucleic acids isolated from a tumor biopsy is used to determine the genomic variant profile of the source tumor, the relative abundance values of somatic variants or transcripts of the tumor may be underestimated, as nucleic acids from normal cells may also be included in the tumor biopsy. In such instances, the relative abundance values can be corrected by various methods, including, but not limited to histological interpretation by a pathologist, AI review, and bioinformatics estimates.

2. Evaluating Genomic Variant Profiles

Once the tumor genomic variant profile (131) and organoid genomic variant profile (133-1) are obtained, similarities or dissimilarities between the two genomic variant profiles are evaluated to assess clonal diversity (316). In some embodiments, the clonal diversity of the tumor organoid cell line is considered similar to the clonal diversity of the reference (e.g., source tumor or liquid biopsy sample) if the genomic variant profile for the tumor organoid cell line satisfies a threshold level of similarity with the genomic variant profile for the tumor sample. In some embodiments, this threshold level of similarity is at least 30, 35, 40, 45, 50, 55, 60, 65, 70, 75, 80, 85, 90, 95, or 99 percent similarity. In some embodiments, the clonal diversity of the tumor organoid cell line is considered similar to the clonal diversity of the reference (e.g., source tumor or liquid biopsy sample) if the genomic variant profile for the tumor organoid cell line and the genomic variant profile for the tumor sample exhibit similar summary statistics. For instance, in some embodiments, the genomic variant profile for the tumor organoid cell line and the genomic variant profile for the reference (e.g., source tumor or liquid biopsy sample) exhibit similar summary statistics when they are at least 5, 10, 15, 20, 25, 30, 35, 40, 45, 50, 55, 60, 65, 70, 75, 80, 85, 90, 95, or 99 percent similar. In some embodiments, the clonal diversity of the tumor organoid cell line is considered dissimilar to the clonal diversity of the reference (e.g., source tumor or liquid biopsy sample) if the genomic variant profile for the tumor organoid cell line satisfies a threshold level of dissimilarity with the genomic variant profile for the tumor sample. In some embodiments, this threshold level of dissimilarity is at least 30, 35, 40, 45, 50, 55, 60, 65, 70, 75, 80, 85, 90, 95, or 99 percent dissimilarity. In some embodiments, the clonal diversity of the tumor organoid cell line is considered dissimilar to the clonal diversity of the reference (e.g., source tumor or liquid biopsy sample) if the genomic variant profile for the tumor organoid cell line and the genomic variant profile for the tumor sample exhibit dissimilar summary statistics. For instance, in some embodiments, the genomic variant profile for the tumor organoid cell line and the genomic variant profile for the reference (e.g., source tumor or liquid biopsy sample) exhibit dissimilar summary statistics when they are at least 5, 10, 15, 20, 25, 30, 35, 40, 45, 50, 55, 60, 65, 70, 75, 80, 85, 90, 95, or 99 percent dissimilar.

In some embodiments where the presence or amounts of particular transcripts are used to assess clonal diversity, the clonal diversity of the tumor organoid cell line is considered similar to the clonal diversity of the reference (e.g., source tumor or liquid biopsy sample) if the transcript profile for the tumor organoid cell line satisfies a threshold level of similarity with the transcript profile for the tumor sample. In some embodiments, this threshold level of similarity is at least 30, 35, 40, 45, 50, 55, 60, 65, 70, 75, 80, 85, 90, 95, or 99 percent similarity. In some embodiments, the clonal diversity of the tumor organoid cell line is considered similar to the clonal diversity of the reference (e.g., source tumor or liquid biopsy sample) if the transcript profile for the tumor organoid cell line and the transcript profile for the tumor sample exhibit similar summary statistics. For instance, in some embodiments, the transcript profile for the tumor organoid cell line and the transcript profile for the reference (e.g., source tumor or liquid biopsy sample) exhibit similar summary statistics when they are at least 5, 10, 15, 20, 25, 30, 35, 40, 45, 50, 55, 60, 65, 70, 75, 80, 85, 90, 95, or 99 percent similar.

In some embodiments where the presence or amounts of particular transcripts are used to assess clonal diversity, the clonal diversity of the tumor organoid cell line is considered dissimilar to the clonal diversity of the reference (e.g., source tumor or liquid biopsy sample) if the transcript profile for the tumor organoid cell line satisfies a threshold level of dissimilarity with the transcript profile for the tumor sample. In some embodiments, the transcript profile for the tumor organoid cell line satisfies a threshold level of dissimilarity with the transcript profile for the reference (e.g., source tumor or liquid biopsy sample) when they are at least 30, 35, 40, 45, 50, 55, 60, 65, 70, 75, 80, 85, 90, 95, or 99 percent similar. In some embodiments, the clonal diversity of the tumor organoid cell line is considered dissimilar to the clonal diversity of the reference (e.g., source tumor or liquid biopsy sample) if the transcript profile for the tumor organoid cell line and the transcript profile for the tumor sample exhibit dissimilar summary statistics. For instance, in some embodiments, the transcript profile of the tumor organoid cell line and the transcript profile for the reference (e.g., source tumor or liquid biopsy sample) exhibit dissimilar summary statistics when they are at least 5, 10, 15, 20, 25, 30, 35, 40, 45, 50, 55, 60, 65, 70, 75, 80, 85, 90, 95, or 99 percent dissimilar.

In the discussion below, clonal diversity is discussed in terms of evaluation of similarity. It will be appreciated that any of the specific embodiments provided below can be reversed to evaluate dissimilarity and all such approaches are within the scope of the present disclosure.

In certain embodiments, a threshold level of similarity is a threshold concordance between the profile (e.g., genomic variant profile or transcript profile) for the tumor organoid cell line and the profile (e.g., genomic variant profile or transcript profile) for the reference tumor. In particular embodiments, the tumor organoid cell line is considered to have similar clonal diversity to its source tumor if there is at least 30, 35, 40, 45, 50, 55, 60, 65, 70, 75, 80, 85, 90, 95, 99 or 100 percent concordance between the two profiles. In some embodiments, clonal diversity for the source tumor sample and tumor organoid is inferred using probabilistic reasoning, such as a Bayesian or frequentist statistical approaches based at least in part on variant allelic frequency (VAF) data, copy number variation (CNV) data, and/or loss of heterozygosity (LOH) data obtained from each of the genomic variant profiles. In certain embodiments, clonal diversity similarity is assessed using a multinomial test or analysis of variance (ANOVA) model.

In some embodiments, clonal diversity similarity between two samples is determined by establishing windows of discrete lengths (e.g., 1-10 bp, 1-10 kb, 1-10 mb, etc) in the nucleic acids sequenced and binning the variants identified in the sequenced genomic windows (e.g., copy number variants (CNV), InDels, somatic single nucleotide variants, rearrangements). Each such bin represents a unique portion of the reference genome. The size of the bins is application dependent. In some embodiments, the human genome is divided into between 50 and 10,000 bins, with each bin representing an independent portion of the reference genome. Then, each respective bin is associated with a count of the variants mapping to the portion of reference genome the respective bin represents. In some embodiments, each of the bins have equal sizes. That is, they each represent portions of the reference genome that are equal sizes. In alternative embodiments, each of the bins have independent sizes. That is, they each represent portions of the reference genome that are the same or different sizes. Once the counts for each bin are acquired, the counts across the plurality of bins for a given sample can be considered a vector, where each element of the vector is the count of a respective bin in the plurality of bins for the sample. In this way, each sample is associated with a vector of scores for the bin counts, which represent the variations the sample has incurred across the genome. In some embodiments, only portions of the genome are represented by the vector. For example, portions of the genome that are highly susceptive to somatic variation and the like may not be included in the vector representation of a sample. With the samples vectorized in this way, any number of distance metrics can be used to assess the similarity or dissimilarity between vectors and thus the similarity or dissimilarity between samples. As such, scores are assigned for the bins and distance (e.g., similarity measure or dissimilarity measure) between the respective bins between each sample are measured using any suitable method, including, for example, high distance in Euclidean space or high dimensional space. See, for example, Aggarwal, 2001, "On the Surprising Behavior of Distance Metrics in High Dimensional Space," Database Theory—International Conference on Database Theory 2001, pp. 420-434, which is hereby incorporated by reference for discussion of distance metrics in Euclidean and high dimensional spaces. Moreover, suitable similarity measures are discussed in Section 6.7 of Duda 1973, where it is disclosed that, for example, a nonmetric similarity function s(x, x') can be used to compare two vectors x and x'. Conventionally, s(x, x') is a symmetric function whose value is large when x and x' are somehow "similar." An example of a nonmetric similarity function s(x, x') is provided on page 218 of Duda 1973. In some embodiments, the distance measure is a cosine distance, a Euclidian distance, a Manhattan distance, a Jaccard distance, a correlation distance, a Chi-square distance, or a Mahalanobis distance. See McCune and Grace, 2002, *Analysis of Ecological Communities*, Chapter 6 "Distance Measures," MjM Software Design, Gleneden Beach, Oreg., which is hereby incorporated by reference.

In some embodiments, a property of the tumor organoid cell line is assessed. In certain embodiments, a cellular growth characteristic is evaluated over time. In some embodiments, a physiological property of the tumor organoid cell line is evaluated over time. In certain embodiments, the time period is at least 1, 5, 10, 15, 20, 25, 30, 35, 40, 45, 50, 55, or 60 minutes. In several embodiments, the time period is at least 1, 2, 3, 4, 5, 6, 7, 8, 9, 10, 11, 12, 13, 14, 15, 16, 17, 18, 19, 20, 21, 22, 23, or 24 hours. In some embodiments, the time period is at least 1, 2, 3, 4, 5, 6, or 7 days. In some embodiments, the time period is at least 1, 2, 3, or 4 weeks. In several embodiments, the time period is at least 1, 2, 3, 4, 5, 6, 7, 8, 9, 10, 11 or 12 months. In some embodiments, the time period is at least 1, 2, 3, 4, 5, 6, 7, 8, 9, 10 years.

After clonal diversity similarity is confirmed (316) between the tumor organoid cell line and the source tumor, the tumor organoid cell line can be used in subsequent applications as a model for the source tumor. Uses for such tumor organoids including drug development and tumor modeling are further discussed in detail below. Further, in some embodiments, a cancer therapy is assigned to the patient after confirming clonal diversity between the tumor organoid cell line and the source tumor.

In certain embodiments, the tumor organoid cell line is used to study the effects of a cancer therapeutic agent and subject responsiveness to the cancer therapeutic agent. In such an embodiment, the tumor organoid cell line is exposed to the cancer therapeutic agent (318), and a property of the exposed tumor organoid cell line is evaluated. In particular embodiments, the clonal diversity of the tumor organoid cell line is compared before and after exposure to the cancer therapeutic agent. As discussed herein, tumor heterogeneity and clonal diversity contributes to drug resistance. As such, understanding changes in tumor heterogeneity and clonal diversity in response to a particular drug treatment can assist in assessing treatment regimens for a particular subject.

In some embodiments, the tumor organoid from the subject is exposed to a cancer therapeutic agent (318) and the exposed tumor organoids are cultured (320). Sequencing data is obtained from the tumor organoid cell line exposed to the cancer therapeutic agent (322) or the organoid culture medium used to culture the tumor organoid cell line and the sequencing data is used to identify a plurality of somatic variants and the relative abundance of these identified somatic variants (324). In some embodiments, a second organoid genomic variant profile (133-$i$) is generated based on the relative abundance values for each respective somatic variant identified in the plurality of somatic variants identified. The first organoid genomic variant profile and the second organoid genomic variant profile are subsequently evaluated to determine changes in the two profiles (326). In certain embodiments, the evaluation includes determining what somatic variant experienced a threshold level of change between first organoid genomic variant profile and the second organoid genomic variant profile. In some embodiments, the threshold level of change is at least a 1, 2, 5, 10, 15, 20, 25, 30, 35, 40, 45, 50, 55, 60, 65, 70, 75, 80, 85, 90, 95, or 99 percent change.

In other embodiments wherein transcript profiles are used to assess clonal diversity, a second organoid transcript profile is generated based on the relative abundance values for each transcript in the plurality of transcripts identified. The first organoid transcript profile and the second organoid transcript profile are subsequently evaluated to determine changes in the two profiles.

In some embodiments, the evaluation includes inputting the first organoid profile (genomic variant profile or transcript profile) and the second organoid profile (genomic variant profile or transcript profile), or a difference between the first and second profiles, into a classifier trained to distinguish between a plurality of tumor classifications. In some embodiments, the classifier is used to determine the effectiveness of a particular treatment regimen based on differences between the first and second organoid profiles. In certain embodiments, the method further assigning a therapy or changes to an existing therapy (328) to the subject based on changes between the first and second organoid profiles.

Additional assessments of responsiveness to a cancer therapeutic can be made over the course of disease by exposing the tumor organoid cell line to the cancer therapeutic agent over several time periods and assessing for clonal diversity using the subject methods as described above. In certain embodiments, the time periods are at least 1, 5, 10, 15, 20, 25, 30, 35, 40, 45, 50, 55, or 60 minutes apart. In several embodiments, the time periods are at least 1, 2, 3, 4, 5, 6, 7, 8, 9, 10, 11, 12, 13, 14, 15, 16, 17, 18, 19, 20, 21, 22, 23, or 24 hours. In some embodiments, the time periods are at least 1, 2, 3, 4, 5, 6, or 7 days. In some embodiments, the time periods are at least 1, 2, 3, or 4 weeks. In several embodiments, the time periods are at least 1, 2, 3, 4, 5, 6, 7, 8, 9, 10, 11 or 12 months. In some embodiments, the time periods are at least 1, 2, 3, 4, 5, 6, 7, 8, 9, 10 years.

3. Liquid Biological Samples

In another aspect, clonal diversity of a tumor organoid is determined by comparing the organoid profile (genomic variant profile or transcript profile) of the tumor organoid cell line to a first liquid profile obtained (genomic variant profile or transcript profile) from cell-free nucleic acids that are isolated from a first liquid biological sample obtained from a subject. Any suitable liquid biological sample can be used including, not limited to blood, whole blood, plasma, serum, urine, cerebrospinal fluid, fecal, saliva, sweat, tears, pleural fluid, pericardial fluid, or peritoneal fluid of the subject.

Liquid biological samples include circulating tumor cells, circulating tumor DNA and exomes. As such, the liquid genomic variant profile obtained from the liquid biological sample provides information relating to all metastatic tumors throughout the subject's body, rather than information for only a single source tumor sample. Liquid biological samples have a high degree of concordance with tissue biopsy and can be used to identify both clonal and subclonal mutations. Moreover, liquid biological samples can advantageously be obtained using non-invasive methods that do not require surgery, as compared to tumor biopsies. Subject tumor organoids that exhibit similar clonal diversity to a liquid biopsy in the subject can be used to assess the responsiveness of a particular cancer therapeutic or treatment regimen in a whole subject, as opposed to only the source tumor from which the tumor organoid is derived.

In some embodiments, the organoid profile (genomic variant profile or transcript profile) of the tumor organoid cell line is obtained from sequencing of nucleic acids obtained from the organoid culture media in which the tumor organoid is cultured rather than a plurality of tumor organoids in the tumor organoid cell line. Using the nucleic acid obtained from organoid culture media allows tumor organoids in the cell line to remain undisturbed. These tumor organoids can then be used for other purposes following the clonal diversity assessment (e.g., therapeutic development and responsiveness studies).

In another aspect, provided herein is a method for evaluating the clonal diversity of a tumor organoid cell line at two different time points. In some embodiments, an organoid profile (genomic variant profile or transcript profile) is obtained at two or more different time points and compared to a reference profile (genomic variant profile or transcript profile) at the same time points to ensure that the similarity in clonal diversity between the source tumor and reference are maintained over time. Such assessments are particular useful in drug development studies to ensure that the tumor organoid model provides a useful model for drug responsiveness of the source tumor and/or subject. In some embodiments the first time point and second time point are at least 1, 5, 10, 15, 20, 25, 30, 35, 40, 45, 50, 55, or 60 minutes apart. In certain embodiments, the first time point and second time point are at least 1, 2, 3, 4, 5, 6, 7, 8, 9, 10, 11, 12, 13, 14, 15, 16, 17, 18, 19, 20, 21, 22, 23, 24 hours apart. In some embodiments, the first time point and second time point are at least 1, 2, 3, 4, 5, 6, or 7 days apart. In some embodiments, the first time point and second time point are at least 1, 2, 3, or 4 weeks apart. In several embodiments, the first time point and second time point are at least 1, 2, 3, 4, 5, 6, 7, 8, 9, 10, 11 or 12 months apart. In some embodiments, the first time point and second time point are at least 1, 2, 3, 4, 5, 6, 7, 8, 9, 10 years apart.

In some embodiments, the method is used to evaluate the effects of an agent on the tumor organoid cell line and/or on the clonal diversity of the tumor organoid cell line. In such embodiments, the agent is administered after the first time point and before the second time point. Agents that can be tested include, but are not limited to, an antibody, a small molecule, an immune cell (e.g., a CAR T-cell, NK cells or effector cells), a hormone, a growth factor, a neurotransmitter, a cytokine, a virus, a parasite, and a bacterium.

In some embodiments, a first culture medium sample is obtained from the organoid culture medium of the tumor organoid cell line. A first organoid profile (genomic variant profile or transcript profile) is determined from cell-free nucleic acids isolated from the organoid culture medium. In some embodiments, the first organoid profile (genomic variant profile or transcript profile) is determined by sequencing the cell-free nucleic acids obtained from the first culture medium sample. In some embodiments where genomic variant profiles are used to assess clonal diversity, the first liquid organoid variant profile includes, for each respective somatic variant in a plurality of somatic variants identified in the first culture medium sample, a relative abundance value for the respective somatic variant.

Next, a second culture medium sample is obtained from the organoid culture medium at a second time point that is after the first time point. A second organoid profile (genomic variant profile or transcript profile) from cell-free nucleic acids isolated from the second culture medium sample. In some embodiments, the second organoid profile (genomic variant profile or transcript profile) is determined by sequencing the cell-free nucleic acids obtained from the second culture medium sample. In some embodiments where genomic variant profiles are used to assess clonal diversity, the second liquid genomic variant profile includes, for each respective somatic variant in a plurality of somatic variants identified in the second culture medium sample, a relative abundance value for the respective somatic variant.

Similarities or differences between the second and the first organoid genomic variant profiles (genomic variant profiles or transcript profiles) are subsequently evaluated. In some embodiments, the evaluating includes determining which somatic variants experienced a threshold level of change between the first organoid genomic variant profile and the second organoid genomic variant profile. In some embodiments, the threshold level of change is at least a 1, 2, 5, 10, 15, 20, 25, 30, 35, 40, 45, 50, 55, 60, 65, 70, 75, 80, 85, 90, 95, or 99 percent change. In particular embodiments, the evaluating includes inputting the first organoid genomic variant profile and the second organoid genomic variant profile, or a difference between the first organoid genomic variant profile and the second organoid genomic variant profile, into a classifier trained to distinguish between a plurality of tumor classifications. In some embodiments, the evaluating includes determining which transcripts experienced a threshold level of change between the first organoid transcript profile and the second organoid transcript profile. In some embodiments, the threshold level of change is at least a 1, 2, 5, 10, 15, 20, 25, 30, 35, 40, 45, 50, 55, 60, 65, 70, 75, 80, 85, 90, 95, or 99 percent change. In particular embodiments, the evaluating includes inputting the first organoid transcript profile and the second organoid transcript profile, or a difference between the first organoid transcript profile and the second organoid transcript profile, into a classifier trained to distinguish between a plurality of tumor classifications.

In yet another aspect, provided herein is a method for evaluating the clonal diversity of one or more tumors in a subject at two different time points. In some embodiments, the method is used to evaluate the effects of a drug or treatment regimen on clonal diversity of the tumor(s) in the subject. In such embodiments, the drug is administered after the first time point and before the second time point. In some embodiments the first time point and second time point are at least 1, 5, 10, 15, 20, 25, 30, 35, 40, 45, 50, 55, or 60 minutes apart. In certain embodiments, the first time point and second time point are at least 1, 2, 3, 4, 5, 6, 7, 8, 9, 10, 11, 12, 13, 14, 15, 16, 17, 18, 19, 20, 21, 22, 23, 24 hours apart. In some embodiments, the first time point and second time point are at least 1, 2, 3, 4, 5, 6, or 7 days apart. In some embodiments, the first time point and second time point are at least 1, 2, 3, or 4 weeks apart. In several embodiments, the first time point and second time point are at least 1, 2, 3, 4, 5, 6, 7, 8, 9, 10, 11 or 12 months apart. In some embodiments, the first time point and second time point are at least 1, 2, 3, 4, 5, 6, 7, 8, 9, 10 years apart.

In some embodiments, a first liquid biological sample is obtained from the subject at a first time point. A first liquid profile (genomic variant profile or transcript profile) is determined from cell-free nucleic acids isolated from the first liquid biological sample. In some embodiments, the first liquid profile (genomic variant profile or transcript profile) is determined by sequencing the cell-free nucleic acids obtained from the first liquid biological sample. In some embodiments, the first liquid genomic variant profile includes, for each respective somatic variant in a plurality of somatic variants identified in the first liquid biological sample, a relative abundance value for the respective somatic variant. In other embodiments, the first liquid transcript profile includes, for each respective transcript in a plurality of transcripts identified in the first liquid biological sample, a relative abundance value for the respective transcript.

Next, a second liquid biological sample is obtained from the subject at a second time point that is after the first time point. A second liquid profile (genomic variant profile or transcript profile) from cell-free nucleic acids isolated from the second liquid biological sample. In some embodiments, the second liquid profile (genomic variant profile or transcript profile) is determined by sequencing the cell-free nucleic acids obtained from the second liquid biological sample. In some embodiments, the second liquid genomic variant profile includes, for each respective somatic variant in a plurality of somatic variants identified in the second liquid biological sample, a relative abundance value for the respective somatic variant. In other embodiments, the second liquid transcript profile includes, for each respective transcript in a plurality of transcripts identified in the second liquid biological sample, a relative abundance value for the respective transcript.

Similarities or dissimilarities between the first and second liquid profiles (genomic variant profiles or transcript profiles) are subsequently evaluated. In some embodiments, the evaluating includes determining which somatic variants experienced a threshold level of change between the first liquid genomic variant profile and the second liquid genomic variant profile. In particular embodiments, the evaluating includes inputting the first liquid genomic variant profile and the second liquid genomic variant profile, or a difference between the first liquid genomic variant profile and the second liquid variant genomic profile, into a classifier trained to distinguish between a plurality of tumor classifications. In other embodiments, the evaluating includes determining which transcripts experienced a threshold level of change between the first liquid transcript profile and the second liquid transcript profile. In particular embodiments, the evaluating includes inputting the first liquid transcript profile and the second liquid transcript profile, or a difference between the first liquid transcript profile and the second liquid transcript profile, into a classifier trained to distinguish between a plurality of tumor classifications.

Such methods of assessing clonal diversity are useful, for example, in evaluating the effects of a therapeutic on a patient. For example, cancer treatment regimens may be determined or altered based on changes in clonal diversity of the patient's tumor(s), as assessed by the subject methods.

4. Computer Systems

In another aspect, provided herein are computer systems for carrying out the subject methods for assessing clonal diversity described herein. In some embodiments, the computer system includes at least one processor and a memory storing at least one program for execution by the at least one processor, the at least one program includes instructions for carrying out the subject method. Details of an exemplary system are described in conjunction with FIG. 1.

Figure 1B:
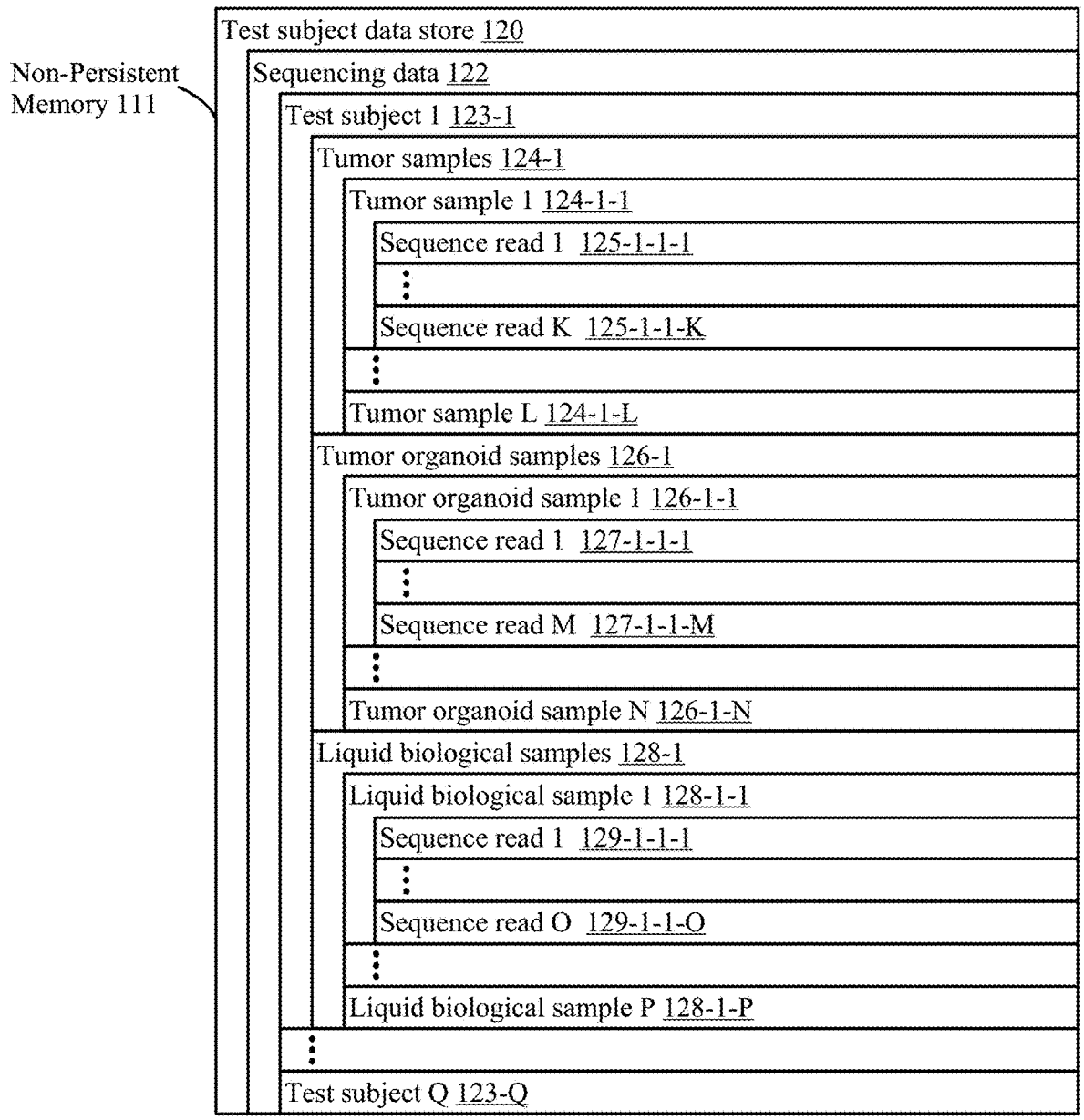
Figure 1C:
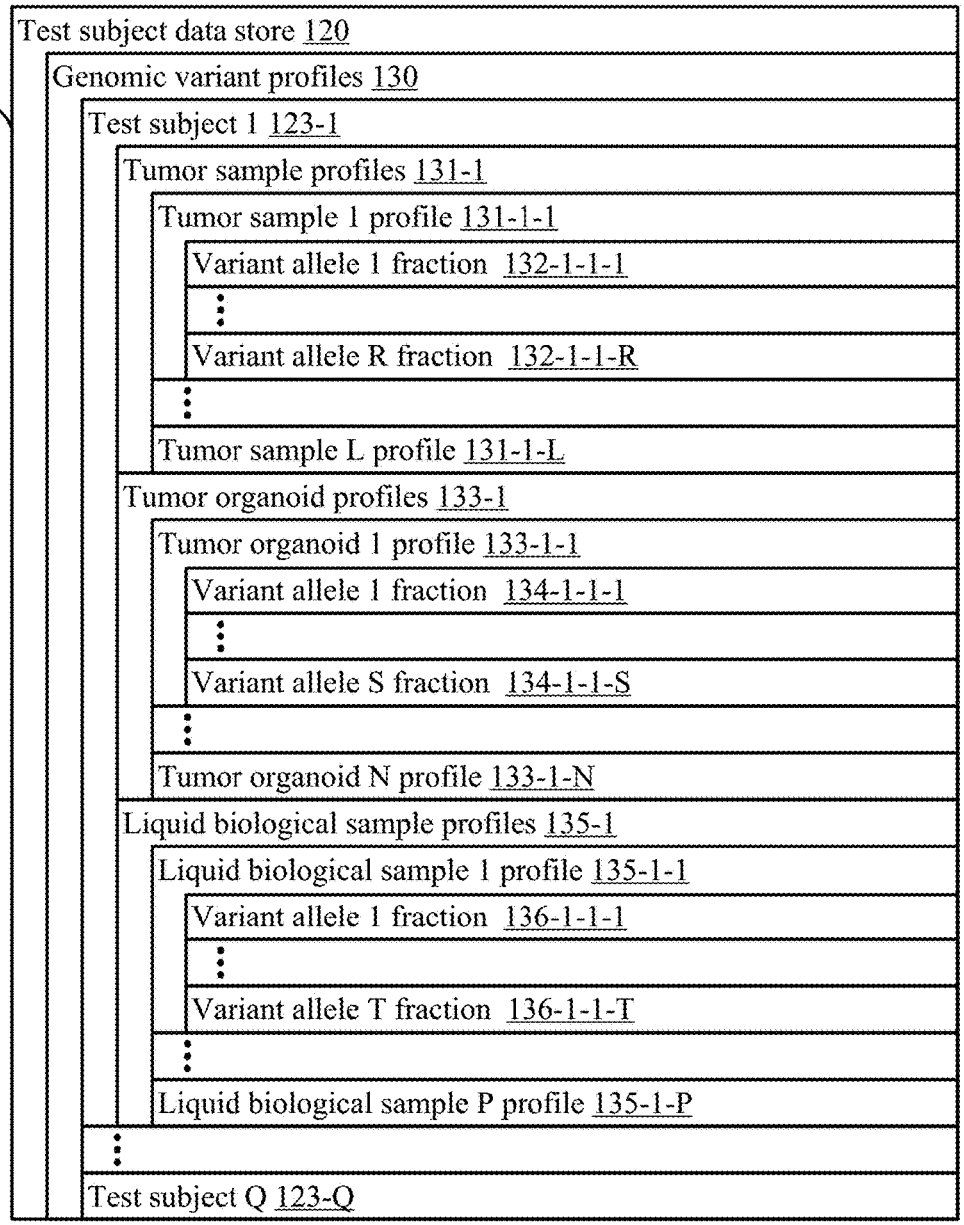

FIG. 1 is a block diagram illustrating a system 100 in accordance with some implementations. The device 100 in some implementations includes one or more processing units CPU(s) 102 (also referred to as processors), one or more network interfaces 104, a user interface 106, a non-persistent memory 111, a persistent memory 112, and one or more communication buses 114 for interconnecting these components. The one or more communication buses 114 optionally include circuitry (sometimes called a chipset) that interconnects and controls communications between system components. The non-persistent memory 111 typically includes high-speed random access memory, such as DRAM, SRAM, DDR RAM, ROM, EEPROM, flash memory, whereas the persistent memory 112 typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. The persistent memory 112 optionally includes one or more storage devices remotely located from the CPU(s) 102. The persistent memory 112, and the non-volatile memory device(s) within the non-persistent memory 112, comprise non-transitory computer readable storage medium. In some implementations, the non-persistent memory 111 or alternatively the non-transitory computer readable storage medium stores the following programs, modules and data structures, or a subset thereof, sometimes in conjunction with the persistent memory 112:

an optional operating system 116, which includes procedures for handling various basic system services and for performing hardware dependent tasks;

a test subject data store 120 for storing datasets containing biological information about test subjects, including sequencing data 122 and somatic variant profile 130. In some embodiments, the sequencing data 122 for each test subject 123 includes, sequencing reads 125 for source tumor samples 124, tumor organoid samples 126, and/or liquid biological samples 128. The sequencing reads 125 for the liquid biological samples 128 can be either liquid biological samples obtained from the test subject or the tumor organoid culture medium, depending on the method as discussed herein. In some embodiments, the genomic variant profile I 130 for each test subject 123 includes one or more tumor genomic variant profiles 131, tumor organoid genomic variant profiles 133, and/or liquid biological sample genomic variant profiles 135. Each of these tumor genomic variant profiles 131, tumor organoid genomic variant profiles 133, and liquid biological sample genomic variant profiles 135 include variant allele fractions 132, 134, and 136, respectively for one or more genomic loci of interest;

a somatic variant identification module 140 for identifying one or more somatic variants from the sequence reads of a tumor sample (124-1), tumor organoid sample (126-1) and/or liquid biological sample (128-1) in the test subject data store 120 to form a genomic variant profile (e.g., tumor genomic variant profile 131, tumor organoid genomic variant profile 133, and/or liquid biological sample genomic variant profile 135) for performing evaluations (e.g., assessing similarity in clonal diversity between a particular tumor sample from a test subject and a particular tumor organoid derived from the tumor sample);

a somatic variant evaluation module 150 for evaluating the particular genomic variant profiles (e.g., tumor genomic variant profiles 131, tumor organoid genomic variant profiles 133, and/or liquid biological sample genomic variant profiles 135) identified by the somatic variant identification module 140. In some embodiments, the somatic variant evaluation module 150 evaluates the similarities and/or dissimilarities between the particular genomic variant profiles. In certain embodiments, similarity metrics 152 are used to evaluate the similarities between or differences between the between the particular genomic variant profiles;

A somatic variant classification module 160 that includes a classifer trained to distinguish between a plurality of tumor classifications. In some embodiments, the classifier is trained to providing a course of action with respect to, for example, the use of a particular cancer therapeutic or a change in treatment regimen based on the evaluation performed by the somatic variant evaluation module 150; and an optional patient reporting module 170 for generating reports about the course of action determine for a test subject.

In various implementations, one or more of the above identified elements are stored in one or more of the previously mentioned memory devices, and correspond to a set of instructions for performing a function described above. The above identified modules, data, or programs (e.g., sets of instructions) need not be implemented as separate software programs, procedures, datasets, or modules, and thus various subsets of these modules and data may be combined or otherwise re-arranged in various implementations.

In some implementations, the non-persistent memory 111 optionally stores a subset of the modules and data structures identified above. Furthermore, in some embodiments, the memory stores additional modules and data structures not described above. In some embodiments, one or more of the above identified elements is stored in a computer system, other than that of system 100, that is addressable by system 100 so that system 100 may retrieve all or a portion of such data when needed.

Although FIG. 1 depicts a "system 100," the figure is intended more as functional description of the various features which may be present in one or more computer systems than as a structural schematic of the implementations described herein. In practice, and as recognized by those of ordinary skill in the art, items shown separately could be combined and some items could be separated. Moreover, although FIG. 1 depicts certain data and modules in non-persistent memory 111, some or all of these data and modules may be in persistent memory 112.

Figure 2:
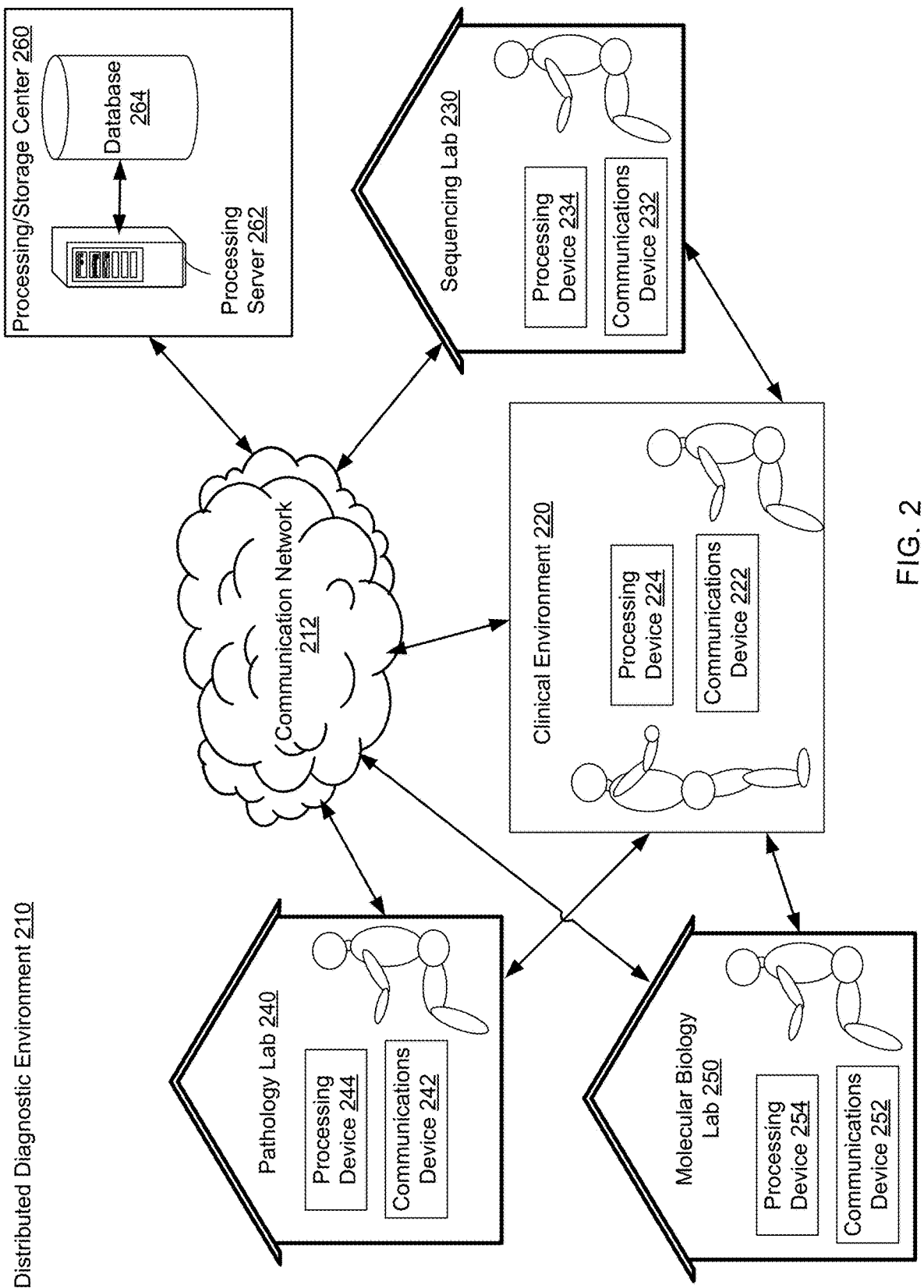
FIG. 2 illustrates an example of a distributed diagnostic environment for evaluating the clonal diversity of a cancer in a subject, in accordance with some embodiments of the present disclosure.

For instance, as depicted in FIG. 2, in some embodiments the method is performed across a distributed diagnostic environment 210, e.g., connected via communication network 212. In some embodiments, one or more biological sample, e.g., one or more tumor biopsy, liquid biological sample, or control sample, is collected from a subject in clinical environment 220, e.g., a doctor's office, hospital, or medical clinic. In some embodiments, a portion of the sample is processed within the clinical environment using a processing device 224, e.g., a nucleic acid sequencer for obtaining sequencing data. In some embodiments, the biological sample or a portion of the biological sample is sent to one or more external environments, e.g., sequencing lab 230, pathology lab 240, and molecular biology lab 250, each of which includes a processing device 234, 244, and 254, respectively, to generate biological data about the subject. In exemplary embodiments, the molecular biology lab 250 develops and maintains tumor organoid cell lines derived from the sample, as well as perform tests using the tumor organoid cell lines (e.g., treatment response). Each environment includes a communications device 222, 232, 242, and 252, respectively, for communicating biological data about the subject to a processing server 262 and/or database 264, which may located in yet another environment, e.g., processing/storage center 260. Thus, in some embodiments, different portions of the systems and methods described herein are fulfilled by different processing devices located in different physical environments.

IV. Tumor Organoid Compositions

In another aspect, provided herein are tumor organoids tumor organoids produced using the subject media and systems and compositions that include such tumor organoids. In some embodiments, the tumor organoid composition includes a three dimensional tumor organoid cell line and an organoid culture medium disclosed herein that is substantially free of R-spondins. In certain embodiments, the culture medium includes any of the growth factor combinations depicted in Table 1. In exemplary embodiments, the composition includes one of the organoid culture media depicted in Table 2.

Tumor organoid cell lines produced using the subject methods and compositions provided herein exhibit one or more properties of the source tumor from which the tumor organoid cell line was derived. In some embodiments, the tumor organoid cell lines exhibits similar clonal diversity as compared to the source tumor. As described herein, tumor clonal diversity can affect responsiveness to cancer treatments. As such, the subject tumor organoid cell lines are useful, for example, developing and screening cancer therapeutics.

The tumor organoid compositions can be derived from any source cancer including, but not limited to, an anal cancer, a basal cell skin cancer, a squamous cancer, a breast cancer, a bladder cancer, a cervical cancer, a colon cancer, an endometrial cancer, a head and neck cancer, a hepatobiliary cancer, a kidney cancer, a gastric cancer, a lung cancer, a mesothelial cancer of the pleural cavity, a mesothelial cancer of the peritoneal cavity, an ovarian cancer, prostate cancer, or a rectal cancer. In certain embodiments, the cancer source is from a human. In particular embodiments, the tumor organoid includes a heterogeneous population of cells that exhibits similar clonal diversity as compared to the source cancer. Clonal diversity can be measured by any standard methods including, for example, those described herein. Particular tumor organoids derived from such sources are described in detail below.

A. Adenoid Cystic Carcinoma (ACC) Tumor Organoid Cell Line

Provided herein is a three dimensional tumor organoid that includes cells derived from an adenoid cystic carcinoma (ACC). The ACC-derived tumor organoid includes a heterogeneous population of cells that exhibit similar clonal diversity as compared to the original adenoid cystic carcinoma. In exemplary embodiments, the tumor organoid is derived from submandibular gland tissue. In some embodiments, the ACC-derived tumor organoid exhibits similar histologic architecture as compared to the ACC. In exemplary embodiments, the ACC is cytokeratin-positive. In some embodiments, the tumor organoid includes a gene mutation, wherein the MYBL1 and NFIB genes are fused (i.e., an NFIB-NYBL1 fusion). In some embodiments, the ACC-derived tumor organoid also exhibits enriched expression for one or more of the following genes as compared to wildtype salivary gland tissue: MYB, BMPR1B, PLEKHG4B, GABRP, STMN1, MEX3A, PALM2, ABCA13, MYBL1, ANLN, PIEZO2, CENPE, FAM227A, GPR98, DNAH2, MED12L, COL9A1, FNDC1, CENPF, NETO2, ST3GAL4, KIAA1549L, FABP7, AACSP1, JRKL-AS1, PTH2R, POU3F2, HORMAD1, COL2A1, LINC01139, LINC01505, KRT81, KPNA2, MCM2, ALS2CR11, MYO16, HAPLN1, ELAVL2, SOX11, ART3, FAM178B, PRAME, EN1, MYEOV, EFNA3, CTNND2, RNF212, ZNF727P, MURC, ADAMTS16, AARD, ZNF883, FAM83H-AS1, FSTL4, SLC35F3, MDFI, AADAT, ACTR3B, TMED11P, PPM1E, MLC1, IQGAP3, KIF23, TSIX, CDCA2, CENPH, MELK, BUB1, SLX4IP, ZNF74, TPX2, RRM2, DIAPH3, KIF14, FREM2, PCDHGB2, RUNX1-IT1, LINC00865, CCNB1, GPR137C, CELSR3, SEPT3, and/or BSN or combinations thereof. In particular embodiments, the tumor organoid is enriched for a subset of these genes. In exemplary embodiments, the subset includes EN1, PRAME, SOX11, SOX4, CDK4, POU3F2 and CCNB1.

The ACC-derived tumor organoid composition may include one or more components of the organoid culture system provided herein. For example, the compositions can include a suitable organoid culture media and/or one or more ECM components that function as a substrate for culturing the tumor organoid. In exemplary embodiments, the organoid culture media is substantially free of R-spondins (e.g., R-spondin1). In some embodiments, the composition include an organoid culture media that includes a plurality of organoid growth factors, where the plurality of organoid growth factors is: a) a combination of EGF, and Noggin orb) a combination of nicotinamide, EGF, Noggin, FGF7 and FGF10. In preferred embodiments, the organoid culture media includes EGF and Noggin and is substantially free of R-spondins.

In exemplary embodiments, the ACC-derived tumor organoid is substantially free of HeLa cells. It has been observed that several known ACC cell-lines have been cross-contaminated with HeLa cells. Liu et al., *Trans Surg* 2(1):10-13 (2017). Thus, tumor organoids derived from such HeLa contaminated cell-lines may be of limited use as an ACC model. The ACC-derived tumor organoid cell-lines provided herein advantageously do not include HeLa cells. In particular embodiments, the ACC-derived tumor organoid include a plurality of cells with less than 5%, 4%, 3%, 2%, 1% HeLa cells. In exemplary embodiments, the ACC-derived tumor organoid are HeLa cell free (i.e., 0% HeLa cells).

B. Additional Tumor Organoid Cell Lines

1. Squamous Cancer

In some embodiments, the tumor organoid cell line is derived from a squamous cancer (e.g., a squamous cell non-small cell lung carcinoma). In particular embodiments, the tumor organoid composition includes an organoid culture medium that includes the following organoid growth factors: EGF and Noggin, and is substantially free of R-spondins. In certain embodiments, the composition further includes one or more ECM components.

2. Adenocarcinoma

In certain embodiments, the tumor organoid cell line is derived from an adenocarcinoma (e.g., adenocarcinoma non-small cell lung carcinoma). In particular embodiments, the tumor organoid composition includes an organoid culture medium that includes one of the following plurality of organoid growth factors: i) a combination of EGF, and Noggin, or ii) a combination of nicotinamide, EGF, Noggin, and one or more fibroblast growth factors (FGFs). In exemplary embodiments, the organoid culture medium is substantially free of R-spondins. In particular embodiments, the organoid culture medium has less than a final concentration of 10 ng/ml R-spondin. In particular embodiments, the organoid culture medium is substantially free of any additional organoid growth factors. In particular embodiments, the composition further includes one or more ECM components.

3. Ovarian Cancer

In certain embodiments, the tumor organoid cell line is derived from an ovarian cancer. In particular embodiments, the tumor organoid composition includes an organoid culture medium that includes one of the following plurality of organoid growth factors: i) a combination of EGF, and Noggin, or ii) a combination of nicotinamide, EGF, Noggin, and one or more fibroblast growth factors (FGFs). In exemplary embodiments, the organoid culture medium is substantially free of R-spondins. In particular embodiments, the organoid culture medium has less than a final concentration of 10 ng/ml R-spondin. In particular embodiments, the organoid culture medium is substantially free of any additional organoid growth factors. In particular embodiments, the composition further includes one or more ECM components.

4. Breast Cancer

In some embodiments, the tumor organoid cell line is derived from a breast cancer. In particular embodiments, the tumor organoid composition includes an organoid culture medium that includes that includes the following organoid growth factors: EGF, Noggin, and one or more fibroblast growth factors (e.g., FGF7 and FGF10). In particular embodiments, the one or more fibroblast growth factors are FGF7 and FGF10. In exemplary embodiments, the organoid culture medium is substantially free of R-spondins. In particular embodiments, the organoid culture medium has less than a final concentration of 10 ng/ml R-spondin. In particular embodiments, the organoid culture medium is substantially free of any additional organoid growth factors. In certain embodiments, the composition further includes one or more ECM components.

5. Head and Neck Cancer

In certain embodiments, the tumor organoid cell line is derived from a head and neck cancer. In particular embodiments, the tumor organoid composition includes an organoid culture medium that includes the following organoid growth factors: EGF and Noggin, and is substantially free of R-spondins. In particular embodiments, the organoid culture medium has less than a final concentration of 10 ng/ml R-spondin. In particular embodiments, the organoid culture medium is substantially free of any additional organoid growth factors. In certain embodiments, the composition further includes one or more ECM components.

6. Gastric Cancer

In some embodiments, the tumor organoid cell line is derived from a gastric cancer. In certain embodiments, the tumor organoid composition includes an organoid culture medium that includes one of the following plurality of organoid growth factors: i) a combination of EGF, and Noggin, or ii) a combination of nicotinamide, EGF, Noggin, and one or more fibroblast growth factors (FGFs). In some embodiments, the one or more FGFs are FGF7 and FGF10. In exemplary embodiments, the organoid culture medium is substantially free of R-spondins. In particular embodiments, the organoid culture medium has less than a final concentration of 10 ng/ml R-spondin. In particular embodiments, the organoid culture medium is substantially free of any additional organoid growth factors. In particular embodiments, the composition further includes one or more ECM components.

7. Colon Cancer

In certain embodiments, the tumor organoid cell line is derived from a colon cancer. In exemplary embodiments, the tumor organoid composition includes an organoid culture medium that includes one of the following plurality of organoid growth factors: i) a combination of EGF, and Noggin, or ii) a combination of nicotinamide, EGF, Noggin, and one or more fibroblast growth factors (FGFs). In some embodiments, the one or more FGFs are FGF7 and FGF10. In exemplary embodiments, the organoid culture medium is substantially free of R-spondins. In particular embodiments, the organoid culture medium has less than a final concentration of 10 ng/ml R-spondin. In particular embodiments, the organoid culture medium is substantially free of any additional organoid growth factors. In particular embodiments, the composition further includes one or more ECM components.

8. Liver Cancer

In some embodiments, the tumor organoid cell line is derived from a liver cancer. In exemplary embodiments, the tumor organoid composition includes an organoid culture medium that includes the of the following organoid growth factors: EGF, Noggin, and one or more fibroblast growth factors (FGFs). In some embodiments, the one or more FGFs are FGF7 and FGF10. In exemplary embodiments, the organoid culture medium is substantially free of R-spondins.

In particular embodiments, the organoid culture medium has less than a final concentration of 10 ng/ml R-spondin. In particular embodiments, the organoid culture medium is substantially free of any additional organoid growth factors. In particular embodiments, the composition further includes one or more ECM components.

9. Esophageal Cancer

In some embodiments, the tumor organoid cell line is derived from an esophageal cancer. In exemplary embodiments, the tumor organoid composition includes an organoid culture medium that includes one of the following plurality of organoid growth factors: i) a combination of EGF, and Noggin, or ii) a combination of nicotinamide, EGF, Noggin, and one or more fibroblast growth factors (FGFs). In exemplary embodiments, the one or more FGFs are FGF7 and FGF10. In exemplary embodiments, the organoid culture medium is substantially free of R-spondins. In particular embodiments, the organoid culture medium has less than a final concentration of 10 ng/ml R-spondin. In particular embodiments, the organoid culture medium is substantially free of any additional organoid growth factors. In particular embodiments, the composition further includes one or more ECM components.

10. Endometrial Cancer

In some embodiments, the tumor organoid cell line is derived from an endometrial cancer. In certain embodiments, the tumor organoid composition includes an organoid culture medium that includes one of the following plurality of organoid growth factors: i) a combination of EGF, and Noggin, or ii) a combination of nicotinamide, EGF, Noggin, and one or more fibroblast growth factors (FGFs). In some embodiments, the one or more FGFs are FGF7 and FGF10. In exemplary embodiments, the organoid culture medium is substantially free of R-spondins. In particular embodiments, the organoid culture medium has less than a final concentration of 10 ng/ml R-spondin. In particular embodiments, the organoid culture medium is substantially free of any additional organoid growth factors. In particular embodiments, the composition further includes one or more ECM components.

V. Methods of Using Tumor Organoid Compositions

A. Drug Development

The subject tumor organoid compositions provided find use in the development of cancer therapeutics. In particular, the subject organoid compositions can be used for drug efficacy testing, pharmacokinetic studies and/or drug toxicity testing. The tumor organoids provided herein can also be also used for high throughput drug screening. Cancer therapeutics that can be tested using the subject compositions include small molecule drug, antibodies, recombinant nucleic acids (e.g., antisense oligonucleotides) and engineered immune cells (e.g., CAR T-cells and NK cells).

Clonal diversity within a particular tumor (intra-tumor clonal diversity) can affect the development of effective therapeutics as subclonal populations within a tumor carrying driver mutations that provide drug resistance can driving cancer progression and allow the tumor to evade targeted therapy. As the subject tumor organoids provided herein exhibit similar clonal diversity to the source tumors, the subject tumor organoids provide useful models for assessing drug responsiveness. In some embodiments, the clonal diversity of the tumor organoid used for drug development is first assessed to determine that it shares a similar clonal diversity as compared to its source tumor.

In some embodiments, the cancer therapeutic is applied to a subject tumor organoid cell line provided herein. A property of the tumor organoid cell is measured after the application of the cancer therapeutic agent, thereby evaluating the effects of the cancer therapeutic. The tumor organoid cell line property that can measured include, but is not limited to: cell mortality, a transcriptional profile, a proteomic profile, clonal diversity, an epigenetic profile, cell morphology, a growth rate, an abundance of extracellular protein in the culture, 3-dimensional cell-cell architecture, biochemical changes in metabolites and non-metabolites, cellular membrane potential, mitochondrial membrane potential of the cultured cells, morphology or architectural changes, upregulation of autophagy, chromosomal changes in ploidy in cultured tumor cells, chromosomal breakage, telomere length changes, cytoskeletal and cell motility changes.

In some embodiments, tumor organoids derived from the subject are exposed to the cancer therapeutics are monitored for growth over time. Exposed tumor organoids that exhibit complete resistance to the cancer therapeutic or a reduced rate of growth inhibition are re-sequenced and somatic variants in subclonal populations that confer a selective advantage in the presence of the cancer therapeutic are determined. Identification of such somatic variants can provide insight into the effectiveness of a particular cancer therapeutic for particular patient groups, as well provide guidance for alternative treatment regimens and therapies.

In some embodiments, the method further includes comparing therapeutic effects in tumor organoids derived from cancer cells and normal cells from the same subject. For example, normal organoids and cancer organoids derived from cells of the same patient can be assessed to determine genetic and epigenetic mutations and gene expression profiles that are cancer-specific, thereby allowing the determination of gene-drug associations and optimization of treatment. Such comparisons also allow one to predict a therapeutic response and to personalize treatment in a specific patient. In another aspect of this method, clonally targeted therapies can be determined by testing the effect of a therapeutic agent on multiple organoids derived from multiple different clones of prostate cancer cells identified in the tumor tissue from a patient, and comparing to the effect of the therapeutic agent on organoids derived from normal cells of the same patient.

Inter-tumoral clonal diversity (i.e., clonal diversity between the same tumor type in different subject) can affect drug screening, as it has been shown that responses to drugs can differ in the same tumor type from different subjects. See, e.g., Jabs et al. Mol. Syst. Biol. 13:955 (2017). As the tumor organoids provided herein exhibit clonal diversity, a plurality of the subject tumor organoids that exhibit difference in clonal diversity can be used for high throughput drug screening. In another aspect, provided herein is a method of high throughput drug screening, wherein a plurality of tumor organoid cell lines that exhibit differences in clonal diversity are contacted with a plurality of candidate cancer therapeutics. The plurality of tumor organoid cell lines are assessed for changes in a property (e.g., tumor growth rate) caused by each of the candidate cancer therapeutics. Candidate cancer therapeutics that cause changes across multiple tumor organoid cell lines are selected for further development.

B. Personalized Medicine

The subject tumor organoid compositions provided also find use in personalized medicine. The subject methods and compositions can be used, for example, to assess the responsiveness of a patient to particular cancer therapeutics and design personalized treatment regimens based on the responsiveness to such cancer therapeutics.

In some embodiments, a cancer therapeutic is exposed to a tumor organoid cell line derived from tumor cells of a subject with a cancer and changes in one or more properties of the tumor organoid cell line are evaluated pre- and post-exposure. Properties that can be assessed include, but are not limited to: cell mortality, a transcriptional profile, a proteomic profile, clonal diversity, an epigenetic profile, cell morphology, a growth rate, an abundance of extracellular protein in the culture, 3-dimensional cell-cell architecture, biochemical changes in metabolites and non-metabolites, cellular membrane potential, mitochondrial membrane potential of the cultured cells, morphology or architectural changes, upregulation of autophagy, chromosomal changes in ploidy in cultured tumor cells, chromosomal breakage, telomere length changes, cytoskeletal and cell motility changes.

In some embodiments, responsiveness is evaluated over a time period. In certain embodiments, the time period is at least 1, 5, 10, 15, 20, 25, 30, 35, 40, 45, 50, 55, or 60 minutes. In several embodiments, the time period is at least 1, 2, 3, 4, 5, 6, 7, 8, 9, 10, 11, 12, 13, 14, 15, 16, 17, 18, 19, 20, 21, 22, 23, or 24 hours. In some embodiments, the time period is at least 1, 2, 3, 4, 5, 6, or 7 days. In some embodiments, the time period is at least 1, 2, 3, or 4 weeks. In several embodiments, the time period is at least 1, 2, 3, 4, 5, 6, 7, 8, 9, 10, 11 or 12 months. In some embodiments, the time period is at least 1, 2, 3, 4, 5, 6, 7, 8, 9, 10 years.

Responsiveness of the subject to the particular cancer therapeutic is then assessed based on the on the evaluation on the changes in the one or more properties and a cancer therapy regimen is designed or altered based on the assessment of responsiveness.

C. Tumor Modeling

The subject tumor organoid compositions provided also find use in tumor modeling application. In some embodiments, the subject tumor organoid is used to assess changes to one or more properties of the tumor organoid compositions over the course of a time period. In some embodiments, the changes are assessed over 2, 3, 4, 5, 6, 7, 8, 9, 10 or more different periods of time. Such models can be useful as a model for understanding in vivo changes to the source tumor from which the tumor organoid is derived. In certain embodiments, the time period is at least 1, 5, 10, 15, 20, 25, 30, 35, 40, 45, 50, 55, or 60 minutes. In several embodiments, the time period is at least 1, 2, 3, 4, 5, 6, 7, 8, 9, 10, 11, 12, 13, 14, 15, 16, 17, 18, 19, 20, 21, 22, 23, or 24 hours. In some embodiments, the time period is at least 1, 2, 3, 4, 5, 6, or 7 days. In some embodiments, the time period is at least 1, 2, 3, or 4 weeks. In several embodiments, the time period is at least 1, 2, 3, 4, 5, 6, 7, 8, 9, 10, 11 or 12 months. In some embodiments, the time period is at least 1, 2, 3, 4, 5, 6, 7, 8, 9, 10 years.

In some embodiments, aliquots of the tumor organoid cell line are taken over a period of time and one or properties are measured from the tumor organoids in each aliquot to assess changes in such properties over the time period. Properties that can be assessed include, for example, a cell mortality, a transcriptional profile, a proteomic profile, clonal diversity, an epigenetic profile, cell morphology, a growth rate, an abundance of extracellular protein in the culture, 3-dimensional cell-cell architecture, biochemical changes in metabolites and non-metabolites, cellular membrane potential, mitochondrial membrane potential of the cultured cells, morphology or architectural changes, upregulation of autophagy, chromosomal changes in ploidy in cultured tumor cells, chromosomal breakage, telomere length changes, cytoskeletal and cell motility changes.

In some embodiments, the subject tumor organoid composition is used assess the effects of one or more agents with respect to one or more properties of the tumor organoid. In some embodiments, the changes are assessed over 2, 3, 4, 5, 6, 7, 8, 9, 10 or more different periods of time. Agents that can be tested include, but are not limited to, an antibody, a small molecule, an immune cell (e.g., a CAR T-cell, NK cells or effector cells), a hormone, a growth factor, a nanoparticle, a nucleic acid, a recombinant nucleic acid, radiation (across the entire spectrum, radionuclide agents, a neurotransmitter, a cytokine, a virus, a parasite, and a bacteria.

EXAMPLES

Example 1: Dissociation of Tumors for Culturing Tumor Organoids

Surgery tumor specimens are delivered in a 50-mL conical tube filled up with RPMI 1640 medium with antibiotics. Using a 25-mL serological pipet, 25 mL of the media is removed from the conical tube without disturbing the tumor pieces and the media is discarded.

The remaining 25 mL of RPMI 1640 medium containing the tumor pieces is poured into one 10 cm cell culture dish. Four-five pieces that are approximately 5×5 mm (or the equivalent if pieces are of differing sizes) are chosen for the tumor dissociation. The tumor pieces to be dissociated is placed in a 10 cm cell culture dish containing 500 µL of the enzyme mix.

The tumor pieces are smaller pieces (small enough to fit through a 5-mL serological pipet) using sterile scalpel and forceps and transferred to one gentleMACS C tube previously labeled with the sample ID using a 5-mL serological pipet.

The 10-cm cell culture dish is washed with the enzyme mix where the tumor was processed and transferred to the gentleMACS C tube.

The C-tube is placed in the Miltenyi gentleMACS Octo Dissociator to dissociate the tumor pieces. Following dissociation, dissociated cells are washed and cell suspension is kept on ice until plating of the cells.

Example 2: Organoid Culture Media Preparation

Tumor organoids are grown in cell culture medium which contains all the specific nutrients. Each medium allows for the fine control of the medium components.

Type B Medium

Stocks were prepared of the different medium components using aseptic techniques and following the indications in Table 3. The specified volume of media components in Table 4 was added to prepare 100 ml of Media Type B. The medium was subsequently filtered through a 0.22µ SteriCup. Medium can be stored up to 2 weeks at 4° C.

TABLE 3

| Reagent | Solvent | Reagent amount | Volume to prepare | Stock Concentration | Storage conditions |
|---|---|---|---|---|---|
| N-acetyle Cysteine | mQ H2O | 8.16 g | 100 mL | 500 mM | −20° C. |
| Nicotinamide | mQ H2O | 12.2 g | 100 mL | 1 M | −20° C. |
| Y-27632 | DMSO | 50 mg | 15.6 mL | 10 mM | −20° C. |
| A83-01 | DMSO | 10 mg | 4.75 mL | 5 mM | −20° C. |
| SB202190 | DMSO | 10 mg | 6.04 mL | 5 mM | −20° C. |
| Recombinant human Noggin | PBS | 100 μg | 2 mL | 50 μg/mL | −20° C. |

TABLE 4

| Component | Stock Concentration | Final Concentration | Volume of component for 100 mL of Media |
|---|---|---|---|
| Advanced DMEM/F12 | 1x | 1x | 93.320 mL |
| HEPES | 1M | 1 mM | 100 μL |
| GlutaMax | 100x | 1x | 1 mL |
| B-27 suppl. w/o vit A | 50x | 1x | 2 mL |
| Penicillin-Streptomycin | 100x | 1x | 1 mL |
| N-acetyl-L-cysteine | 500 mM | 1 mM | 200 μL |
| Nicotinamide | 1M | 10 mM | 1 mL |
| Y-27632 | 10 mM | 5 μM | 50 μL |
| A83-01 | 5 mM | 0.5 μM | 10 μL |
| SB202190 | 5 mM | 0.5 μM | 10 μL |
| Recombinant human Noggin | 50 μg/mL | 100 ng/ml | 200 μL |

NOTE:
* Primocin at a final concentration of 100 μg/ml (stock concentration of 50 mg/mL (500x)) is added to the medium for the first week of tumor organoid culture after tumor tissue dissociation Type C Medium Stocks were prepared of the different medium components using aseptic techniques and following the indications in Table 5. The specified volume of media components in Table 6 was added to prepare 100 ml of Media Type C. The medium was subsequently filtered through a 0.22μ SteriCup. Medium can be stored up to 2 weeks at 4° C.

TABLE 5

| Reagent | Solvent | Reagent amount | Volume to prepare | Stock Concentration | Storage conditions |
|---|---|---|---|---|---|
| N-acetyle Cysteine | mQ H2O | 8.16 g | 100 mL | 500 mM | −20° C. |
| Nicotinamide | mQ H2O | 12.2 g | 100 mL | 1 M | −20° C. |
| Y-27632 | DMSO | 50 mg | 15.6 mL | 10 mM | −20° C. |
| A83-01 | DMSO | 10 mg | 4.75 mL | 5 mM | −20° C. |
| SB202190 | DMSO | 10 mg | 6.04 mL | 5 mM | −20° C. |
| Recombinant human EGF | PBS | 1 mg | 5 mL | 200 μg/mL | −20° C. |
| Recombinant human Noggin | PBS | 100 μg | 2 mL | 50 μg/mL | −20° C. |

TABLE 6

| Component | Stock Concentration | Final Concentration | Volume of component for 100 mL of Media |
|---|---|---|---|
| Advanced DMEM/F12 | 1x | 1x | 93.320 mL |
| HEPES | 1M | 1 mM | 100 μL |
| GlutaMax | 100x | 1x | 1 mL |
| B-27 suppl. w/o vit A | 50x | 1x | 2 mL |
| Penicillin-Streptomycin | 100x | 1x | 1 mL |
| N-acetyl-L-cysteine | 500 mM | 1 mM | 200 μL |
| Nicotinamide | 1M | 10 mM | 1 mL |
| Y-27632 | 10 mM | 5 μM | 50 μL |
| A83-01 | 5 mM | 0.5 μM | 10 μL |
| SB202190 | 5 mM | 0.5 μM | 10 μL |
| Recombinant human EGF | 200 μg/mL | 50 ng/ml | 25 μL |
| Recombinant human Noggin | 50 μg/mL | 100 ng/ml | 200 μL |

NOTE:
* Primocin at a final concentration of 100 μg/ml (stock concentration of 50 mg/mL (500x)) is added to the medium for the first week of tumor organoid culture after tumor tissue dissociation Type D Medium Stocks were prepared of the different medium components using aseptic techniques and following the indications in Table 7. The specified volume of media components in Table 8 was added to prepare 100 ml of Media Type D. The medium was subsequently filtered through a 0.22μ SteriCup. Medium can be stored up to 2 weeks at 4° C.

TABLE 7

| Reagent | Solvent | Reagent amount | Volume to prepare | Stock Concentration | Storage conditions |
|---|---|---|---|---|---|
| N-acetyle Cysteine | mQ H2O | 8.16 g | 100 mL | 500 mM | −20° C. |
| Nicotinamide | mQ H2O | 12.2 g | 100 mL | 1 M | −20° C. |
| Y-27632 | DMSO | 50 mg | 15.6 mL | 10 mM | −20° C. |
| A83-01 | DMSO | 10 mg | 4.75 mL | 5 mM | −20° C. |
| SB202190 | DMSO | 10 mg | 6.04 mL | 5 mM | −20° C. |
| Recombinant human EGF | PBS | 1 mg | 5 mL | 200 μg/mL | −20° C. |
| Recombinant human Noggin | PBS | 100 μg | 2 mL | 50 μg/mL | −20° C. |
| Recombinant human FGF7 | PBS | 50 μg | 1 mL | 50 μg/mL | −20° C. |
| Recombinant human FGF10 | PBS | 25 μg | 500 μL | 50 μg/mL | −20° C. |

*rh Wnt-3A is ordered in vials of either 10 μg or 500 μg.

TABLE 8

| Component | Stock Concentration | Final Concentration | Volume of component for 100 mL of Media |
|---|---|---|---|
| Advanced DMEM/F12 | 1x | 1x | 94.420 mL |
| HEPES | 1M | 1 mM | 100 μL |
| GlutaMax | 100x | 1x | 1 mL |
| B-27 suppl. w/o vit A | 50x | 1x | 2 mL |
| Penicillin-Streptomycin | 100x | 1x | 1 mL |
| N-acetyl-L-cysteine | 500 mM | 1 mM | 200 μL |
| Nicotinamide | 1M | 10 mM | 1 mL |
| Y-27632 | 10 mM | 5 μM | 50 μL |
| A83-01 | 5 mM | 0.5 μM | 10 μL |
| SB202190 | 5 mM | 0.5 μM | 10 μL |
| Recombinant human EGF | 200 μg/mL | 50 ng/ml | 25 μL |
| Recombinant human Noggin | 50 μg/mL | 100 ng/ml | 200 μL |
| Recombinant human FGF7 | 50 μg/mL | 25 ng/mL | 50 μL |
| Recombinant human FGF10 | 50 μg/mL | 100 ng/mL | 200 μL |

NOTE:
* Primocin at a final concentration of 100 μg/ml (stock concentration of 50 mg/mL (500x)) is added to the medium for the first week of tumor organoid culture after tumor tissue dissociation Type E Medium Stocks were prepared of the different medium components using aseptic techniques and following the indications in Table 9. The specified volume of media components in Table 10 was added to prepare 100 ml of Media Type E. The medium was subsequently filtered through a 0.22μ SteriCup. Medium can be stored up to 2 weeks at 4° C.

TABLE 9

| Reagent | Solvent | Reagent amount | Volume to prepare | Stock Concentration | Storage conditions |
|---|---|---|---|---|---|
| N-acetyle Cysteine | mQ H2O | 8.16 g | 100 mL | 500 mM | −20° C. |
| Nicotinamide | mQ H2O | 12.2 g | 100 mL | 1 M | −20° C. |
| Y-27632 | DMSO | 50 mg | 15.6 mL | 10 mM | −20° C. |
| A83-01 | DMSO | 10 mg | 4.75 mL | 5 mM | −20° C. |
| SB202190 | DMSO | 10 mg | 6.04 mL | 5 mM | −20° C. |
| Recombinant human EGF | PBS | 1 mg | 2 mL | 500 μg/mL | −20° C. |
| Recombinant human Noggin | PBS | 100 μg | 2 mL | 50 μg/mL | −20° C. |
| Recombinant human Wnt-3A* | PBS | 10 μg | 1 mL | 10 μg/mL | −20° C. |
| Recombinant human R-Spondin1 | PBS | 1 mg | 2 mL | 500 μg/mL | −20° C. |

*rh Wnt-3A is ordered in vials of either 10 ug or 500 ug.

TABLE 10

| Component | Stock Concentration | Final Concentration | Volume of component for 100 mL of Media |
|---|---|---|---|
| Advanced DMEM/F12 | 1x | 1x | 93.320 mL |
| HEPES | 1M | 1 mM | 100 μL |
| GlutaMax | 100x | 1x | 1 mL |
| B-27 suppl. w/o vit A | 50x | 1x | 2 mL |
| Penicillin-Streptomycin | 100x | 1x | 1 mL |
| N-acetyl-L-cysteine | 500 mM | 1 mM | 200 μL |
| Nicotinamide | 1M | 10 mM | 1 mL |
| Y-27632 | 10 mM | 5 μM | 50 μL |
| A83-01 | 5 mM | 0.5 μM | 10 μL |
| SB202190 | 5 mM | 0.5 μM | 10 μL |
| Recombinant human EGF | 500 μg/mL | 50 ng/ml | 10 μL |
| Recombinant human Noggin | 50 μg/mL | 100 ng/ml | 200 μL |
| Recombinant human Wnt-3A | 10 μg/mL | 100 ng/ml | 1 mL |
| Recombinant human R-Spondin1 | 500 μg/mL | 500 ng/ml | 100 μL |

NOTE:
* Primocin at a final concentration of 100 μg/ml (stock concentration of 50 mg/mL (500x)) is added to the medium for the first week of tumor organoid culture after tumor tissue dissociation Type F Medium Stocks were prepared of the different medium components using aseptic techniques and following the indications in Table 11. The specified volume of media components in Table 12 was added to prepare 100 ml of Media Type F. The medium was subsequently filtered through a 0.22μ SteriCup. Medium can be stored up to 2 weeks at 4° C.

TABLE 11

| Reagent | Solvent | Reagent amount | Volume to prepare | Stock Concentration | Storage conditions |
|---|---|---|---|---|---|
| N-acetyle Cysteine | mQ H2O | 8.16 g | 100 mL | 500 mM | −20° C. |
| Nicotinamide | mQ H2O | 12.2 g | 100 mL | 1 M | −20° C. |
| Y-27632 | DMSO | 50 mg | 15.6 mL | 10 mM | −20° C. |
| A83-01 | DMSO | 10 mg | 4.75 mL | 5 mM | −20° C. |
| SB202190 | DMSO | 10 mg | 6.04 mL | 5 mM | −20° C. |
| Recombinant human EGF | PBS | 1 mg | 5 mL | 200 μg/mL | −20° C. |
| Recombinant human Noggin | PBS | 100 μg | 2 mL | 50 μg/mL | −20° C. |
| Recombinant human Wnt-3A* | PBS | 10 μg | 1 mL | 10 μg/mL | −20° C. |
| Recombinant human R-Spondin1 | PBS | 1 mg | 5 mL | 200 μg/mL | −20° C. |
| Recombinant human FGF7 | PBS | 50 μg | 1 mL | 50 μg/mL | −20° C. |
| Recombinant human FGF10 | PBS | 25 μg | 500 μL | 50 μg/mL | −20° C. |

*rh Wnt-3A is ordered in vials of either 10 μg or 500 μg. Check vial label carefully for amounts

TABLE 12

| Component | Stock Concentration | Final Concentration | Volume of component for 100 mL of Media |
|---|---|---|---|
| Advanced DMEM/F12 | 1x | 1x | 93.320 mL |
| HEPES | 1M | 1 mM | 100 μL |
| GlutaMax | 100x | 1x | 1 mL |
| B-27 suppl. w/o vit A | 50x | 1x | 2 mL |
| Penicillin-Streptomycin | 100x | 1x | 1 mL |
| N-acetyl-L-cysteine | 500 mM | 1 mM | 200 μL |
| Nicotinamide | 1M | 10 mM | 1 mL |
| Y-27632 | 10 mM | 5 μM | 50 μL |

TABLE 12-continued

| Component | Stock Concentration | Final Concentration | Volume of component for 100 mL of Media |
|---|---|---|---|
| A83-01 | 5 mM | 0.5 µM | 10 µL |
| SB202190 | 5 mM | 0.5 µM | 10 µL |
| Recombinant human EGF | 200 µg/mL | 50 ng/ml | 25 µL |
| Recombinant human Noggin | 50 µg/mL | 100 ng/ml | 200 µL |
| Recombinant human Wnt-3A | 10 µg/mL | 100 ng/ml | 1 mL |
| Recombinant human R-Spondin1 | 200 µg/mL | 500 ng/ml | 250 µL |
| Recombinant human FGF7 | 50 µg/mL | 25 ng/mL | 50 µL |
| Recombinant human FGF10 | 50 µg/mL | 100 ng/mL | 200 µL |

NOTE:
* Primocin at a final concentration of 100 µg/ml (stock concentration of 50 mg/mL (500x) is added to the medium for the first week of tumor organoid culture after tumor tissue dissociation Example 3: Culturing of Tumor Organoids Tumor tissue from different cancer sources, including squamous cancer, breast cancer, lung cancer, colon cancer, ovarian cancer, prostate cancer, gastric cancer, esophageal cancer and endometrial cancers were obtained. Tumor cells from the various tumor tissue were dissociated using the method described in Example 1. The disassociated cells where plated in extracellular matrix and subsequently cultured in the various organoid culture media as described in Example 2. Tumor organoid growth and development were assessed using time lapse brightfield microscopy as a "Niche Factor" assay in the different culture media the and media with the fewest components (i.e., minimal essential media) to support adequate growth for each tumor organoid was determined, as shown in Table 13.

TABLE 13

| Tumor organoid source cancer | Minimal essential medium |
|---|---|
| Squamous cancer | Type C |
| Breast cancer | Type D |
| Lung cancer | Type C/D/E |
| Colon cancer | Type E2* |
| Ovarian cancer | Type E |
| Prostate cancer | Type C/D/E |
| Esophageal Cancer | Type C/D/E |
| Endometrial cancer | Type E2* |

*Type E2 is similar to Type E except serum replacement is N21 instead of B27

Assessing Clonal Diversity of Tumor Organoid

Clones were preserved by plating in partially digested tumor suspensions i.e. not single cell suspensions to prevent anoikis.

To determine clonal population abundance (i.e. clonal diversity) from the tumor, an aliquot representing 60,000 cells from the tumor is reserved for deep sequencing, representing a theoretical minimum allele fraction of $1/120,000$ assuming a diploid genome. The remainder cells are cultured at log-phase indefinitely within basement membrane matrix simulating common epithelial tissue ground substance. Log-phase implies a plating density to support slow growing clones and avoid a scenario where nutrients, growth factors, and matrix are constrained.

Clonal diversity was assessed at time points representing 8 doublings which is assessed by visual examination of the cellular content of tumor organoid cultures before harvesting. Harvesting of cultures involves partial digestion of the entirety of the culture and again sampling approximately 60,000 cells in three separate aliquots to account for sampling error. Again, assuming a diploid genome, $1/120,000$ allele fraction is the theoretical limit of sensitivity.

Total nucleic acid was extracted from the tumor and tumor organoid, followed by DNA isolation. Library prep was achieved using the xT sequencing platform. DNA from the native tumor was sequenced and used as a gold standard to compare the tumor organoids. Genomic concordance to ascertain preservation of clonal diversity was achieved by pairwise comparison of the allelic fraction variants between the tumor and tumor organoid.

Figure 5A:
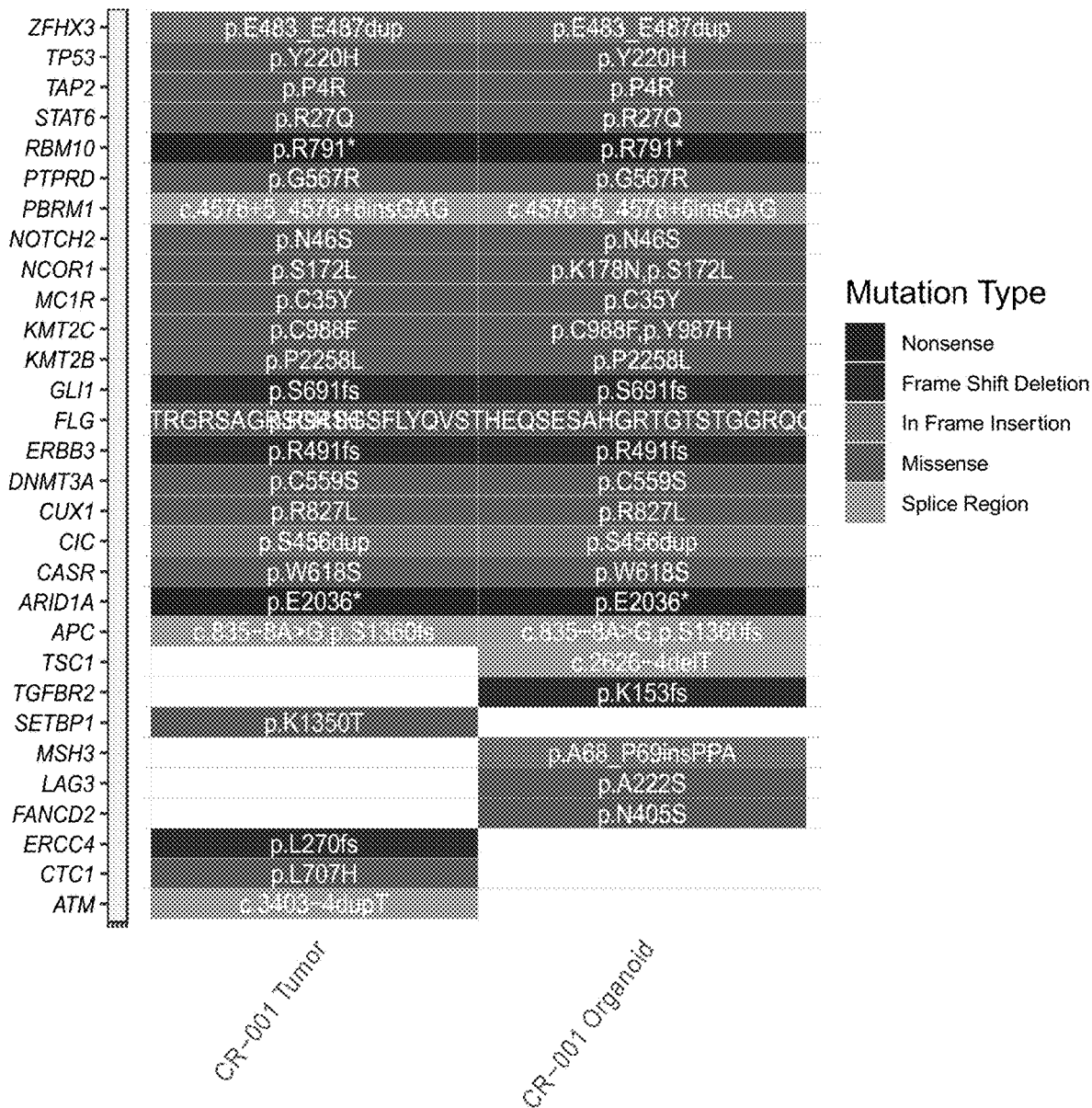
FIG. 5A, FIG. 5B, and FIG. 5C collectively show the similarity of somatic variant profiles determined from a tumor sample and a corresponding tumor organoid cell line derived from the same tumor, in accordance with some embodiments of the present disclosure. Specifically, FIG. 5A lists all of the somatic variants identified and validated from sequence reads of nucleic acids isolated from the tumor sample and the tumor organoid cell line, as well as several measures of concordance between the corresponding somatic variant profiles.
Figure 5B:
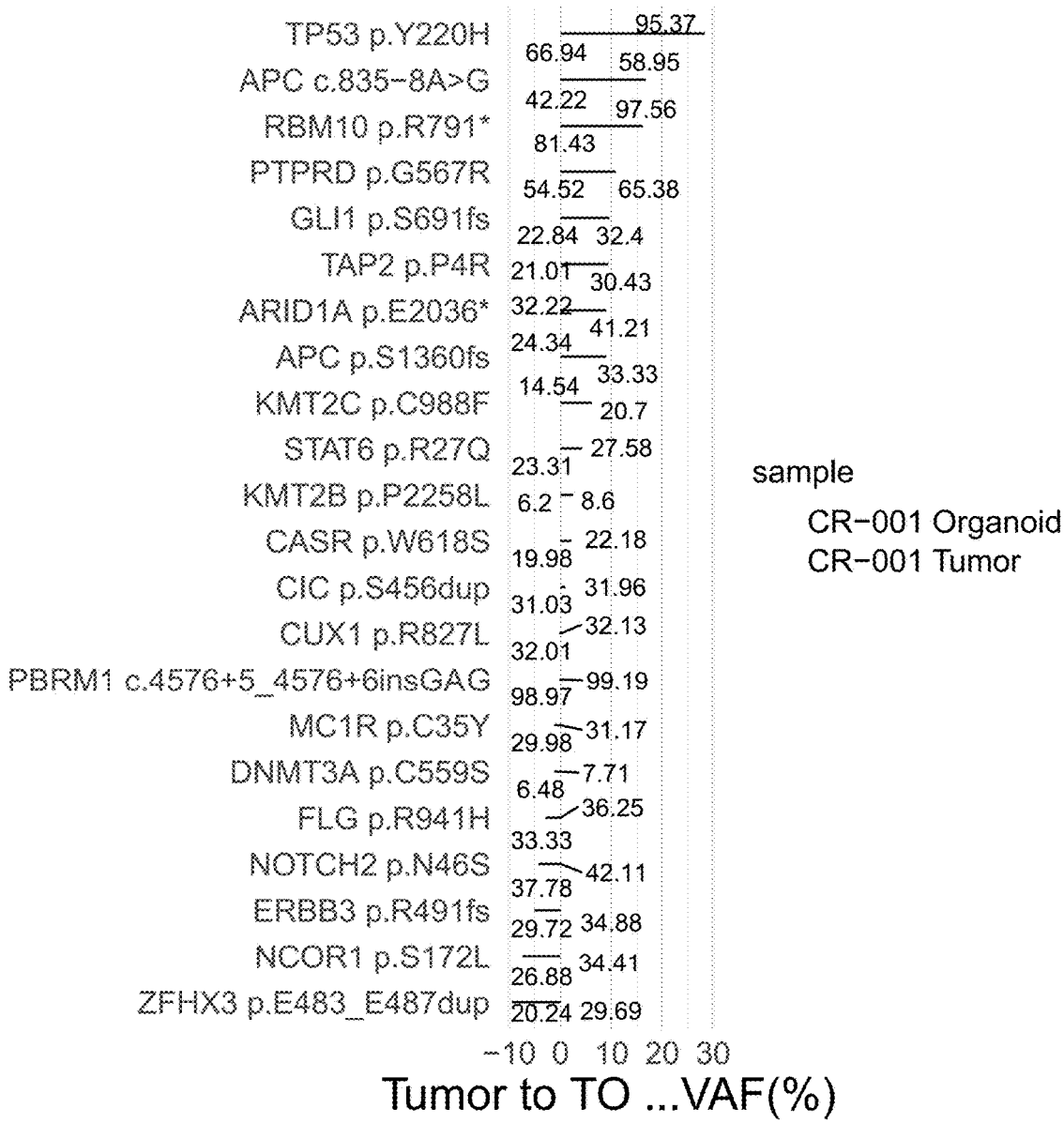
Figure 5C:
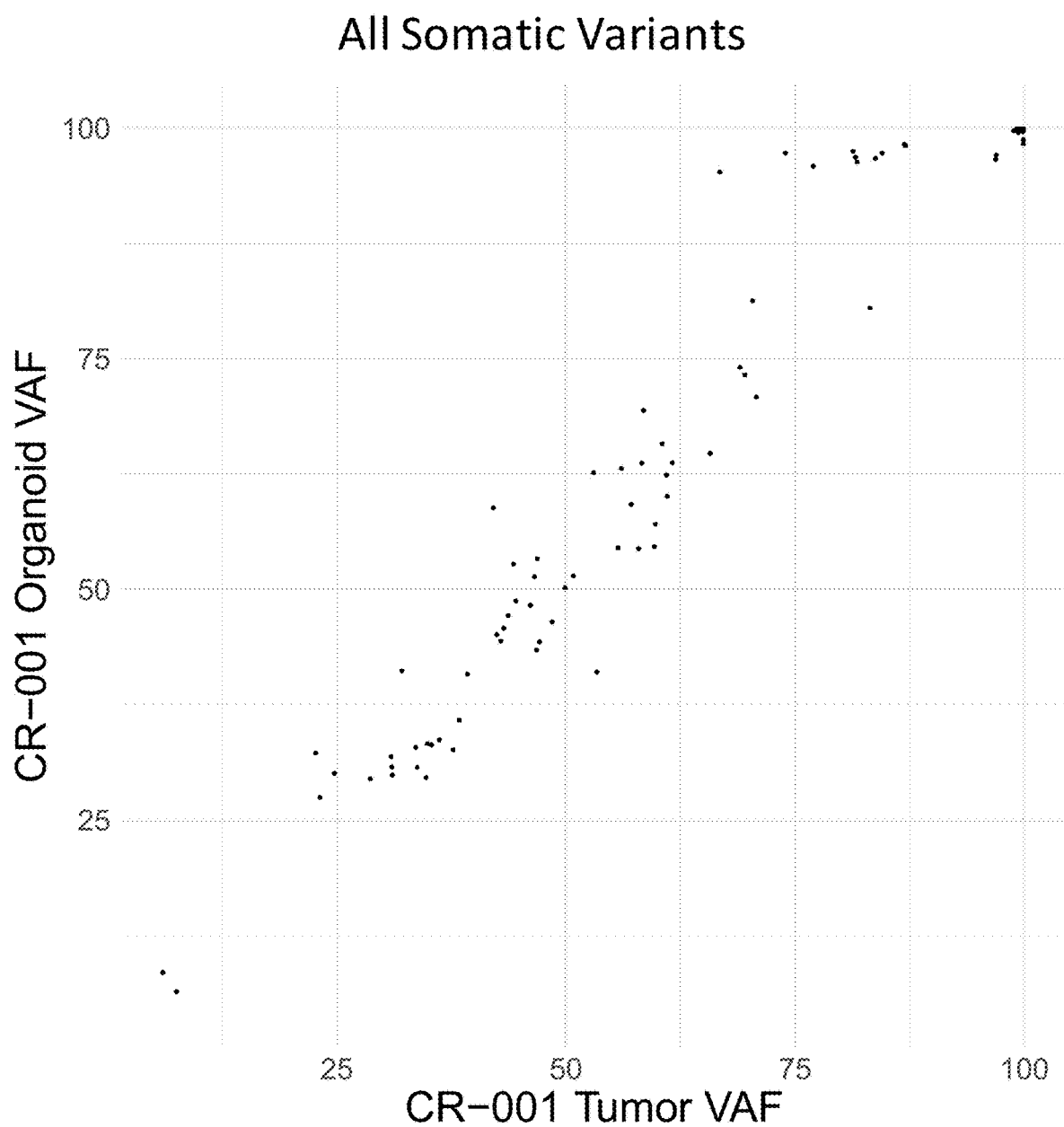
Figure 6A:
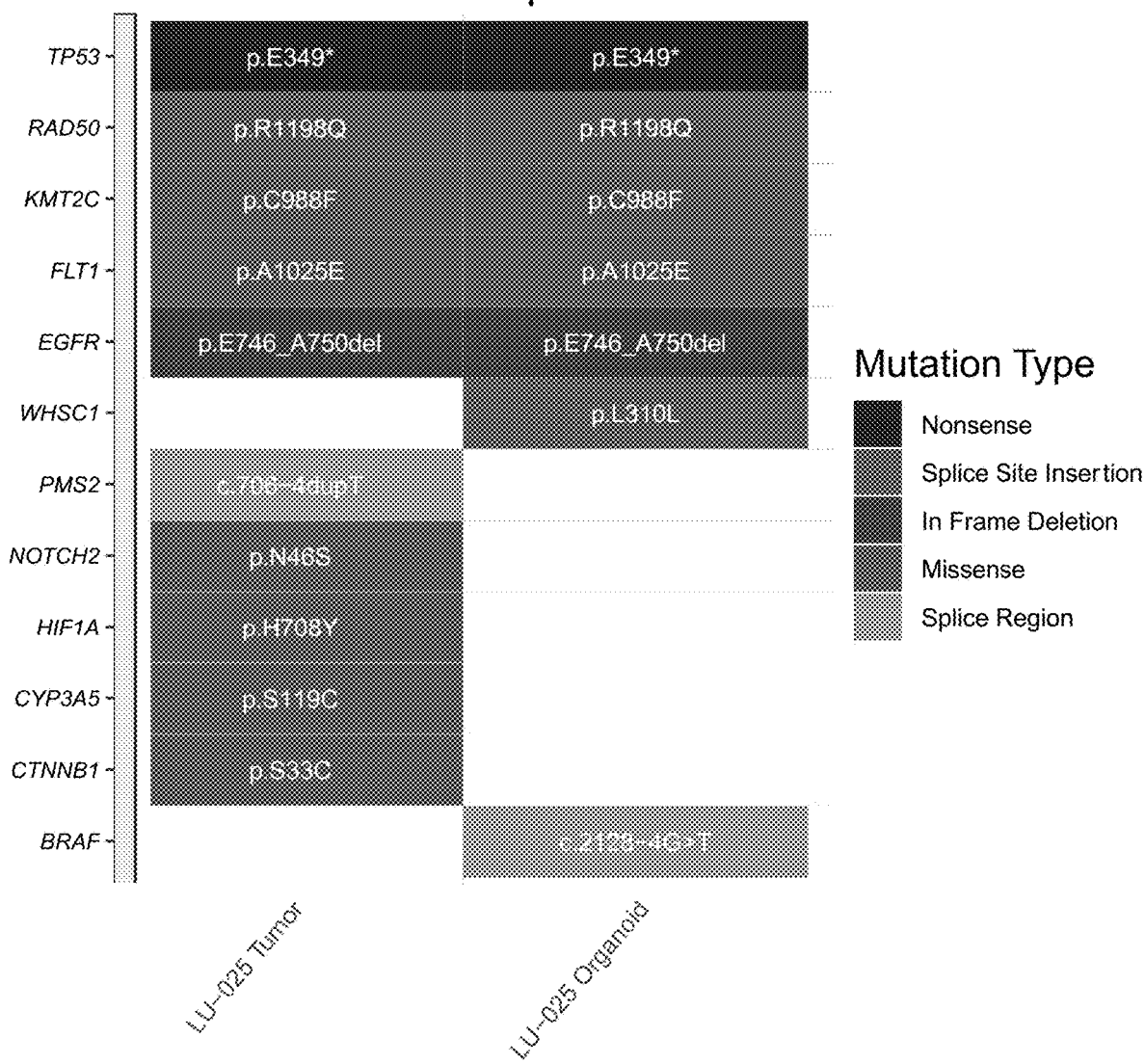
FIG. 6A, FIG. 6B, and FIG. 6C_collectively show the similarity of somatic variant profiles determined from a tumor sample and a corresponding tumor organoid cell line derived from the same tumor, in accordance with some embodiments of the present disclosure. Specifically, FIG. 6A lists all of the somatic variants identified and validated from sequence reads of nucleic acids isolated from the tumor sample and the tumor organoid cell line, as well as several measures of concordance between the corresponding somatic variant profiles.
Figure 6B:
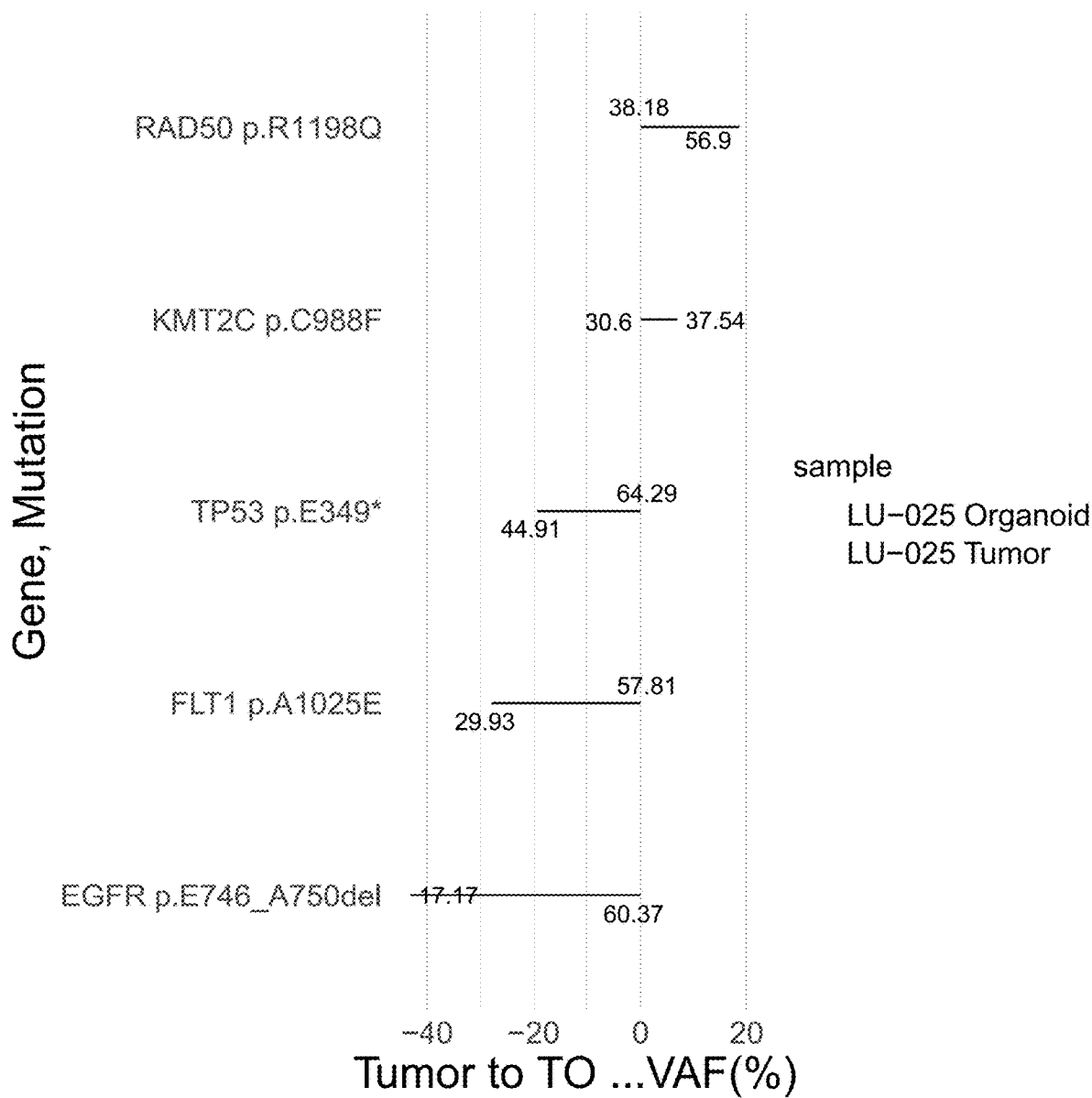
Figure 6C:
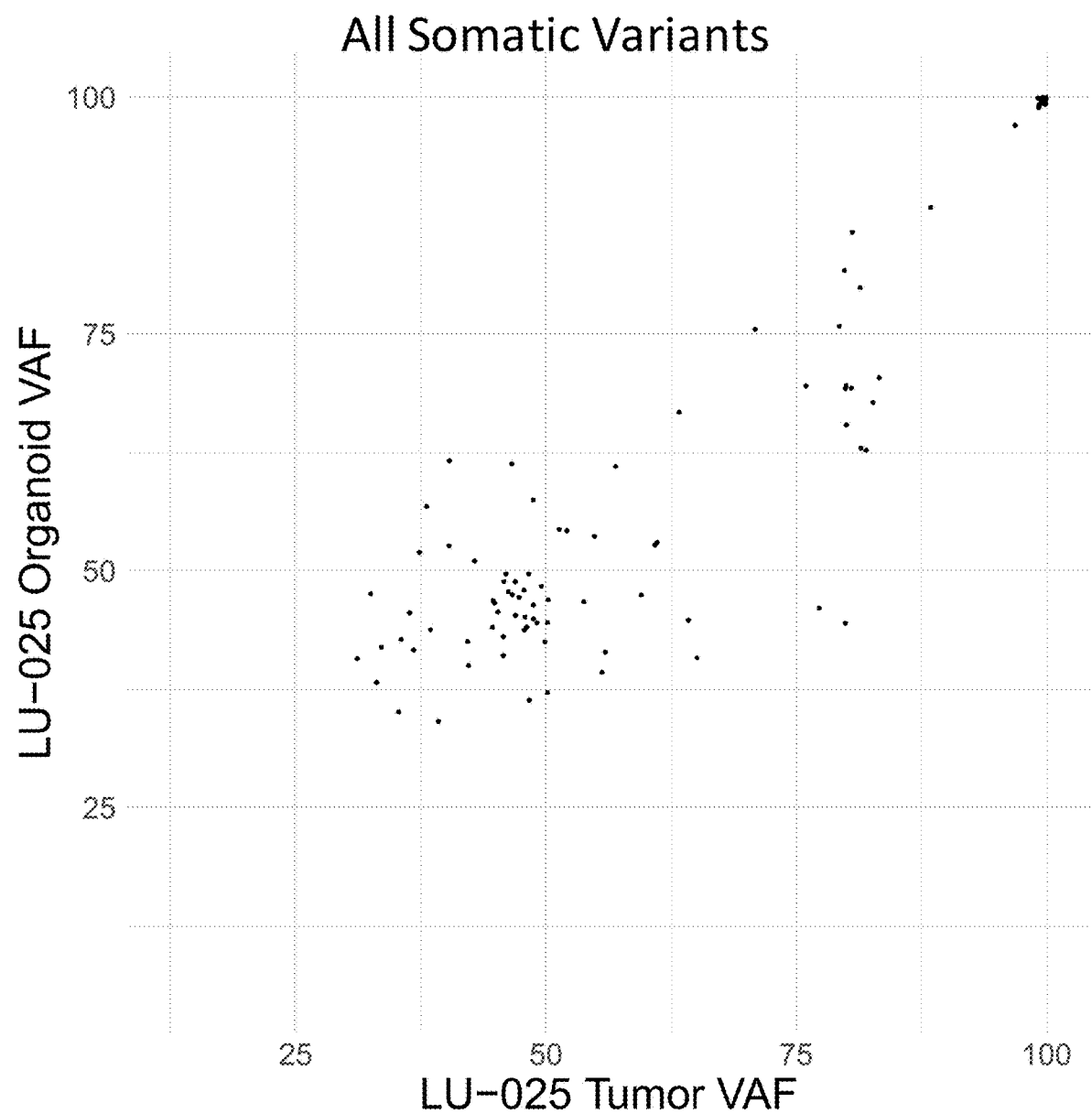
Figure 7A:
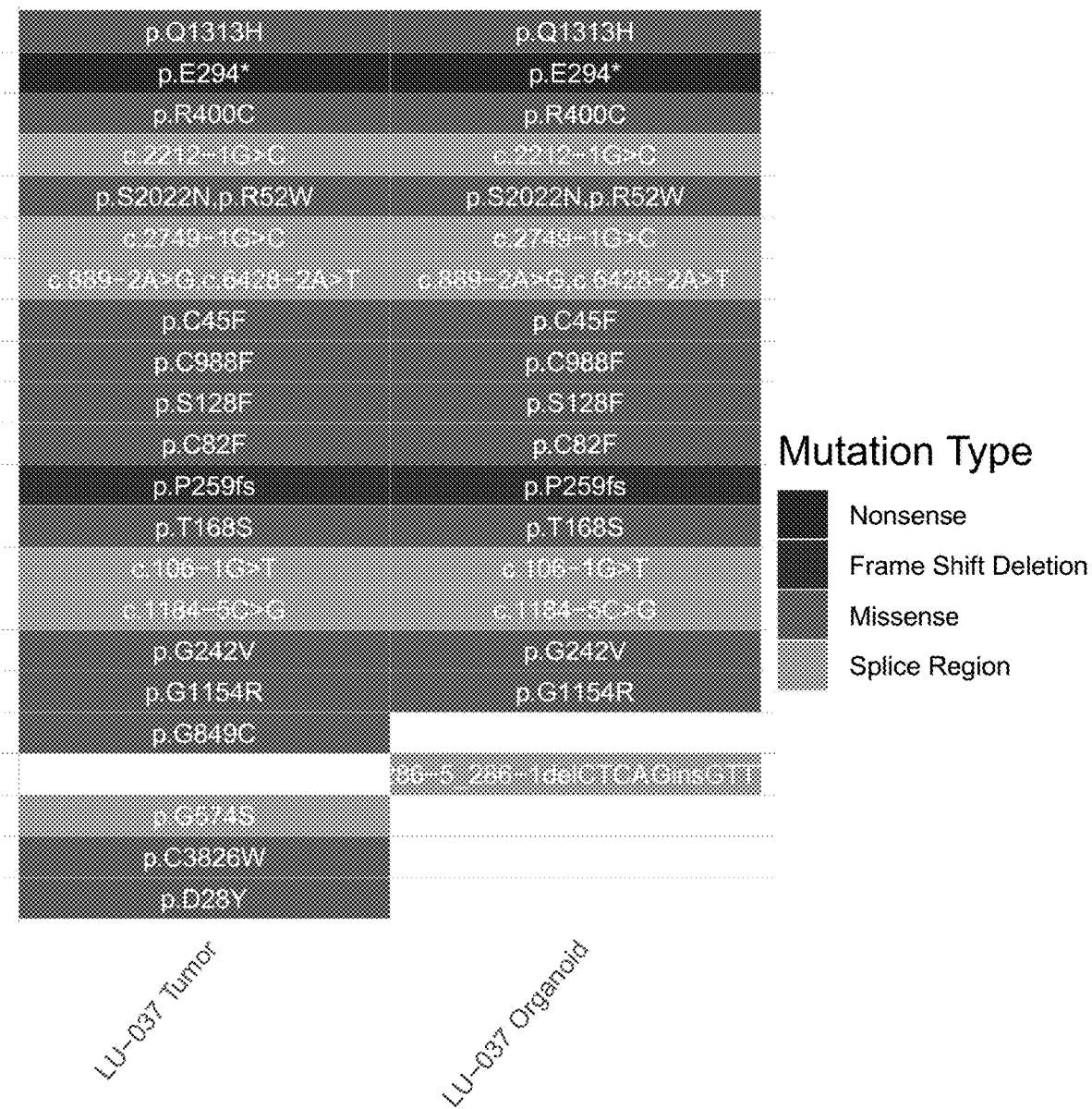
FIG. 7A, FIG. 7B, and FIG. 7C collectively show the similarity of somatic variant profiles determined from a tumor sample and a corresponding tumor organoid cell line derived from the same tumor, in accordance with some embodiments of the present disclosure. Specifically, FIG. 7A lists all of the somatic variants identified and validated from sequence reads of nucleic acids isolated from the tumor sample and the tumor organoid cell line, as well as several measures of concordance between the corresponding somatic variant profiles.
Figure 7B:
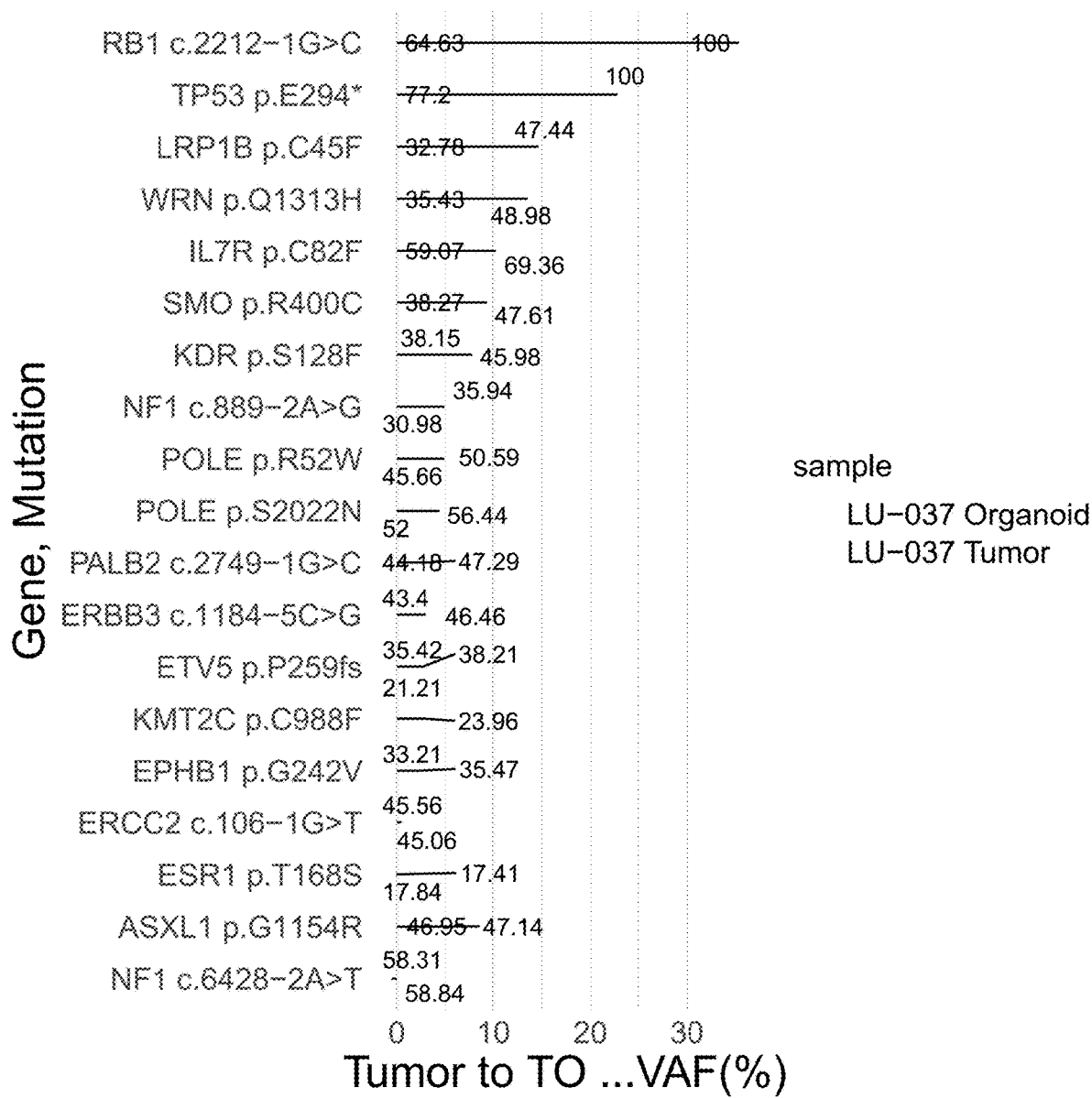
Figure 7C:
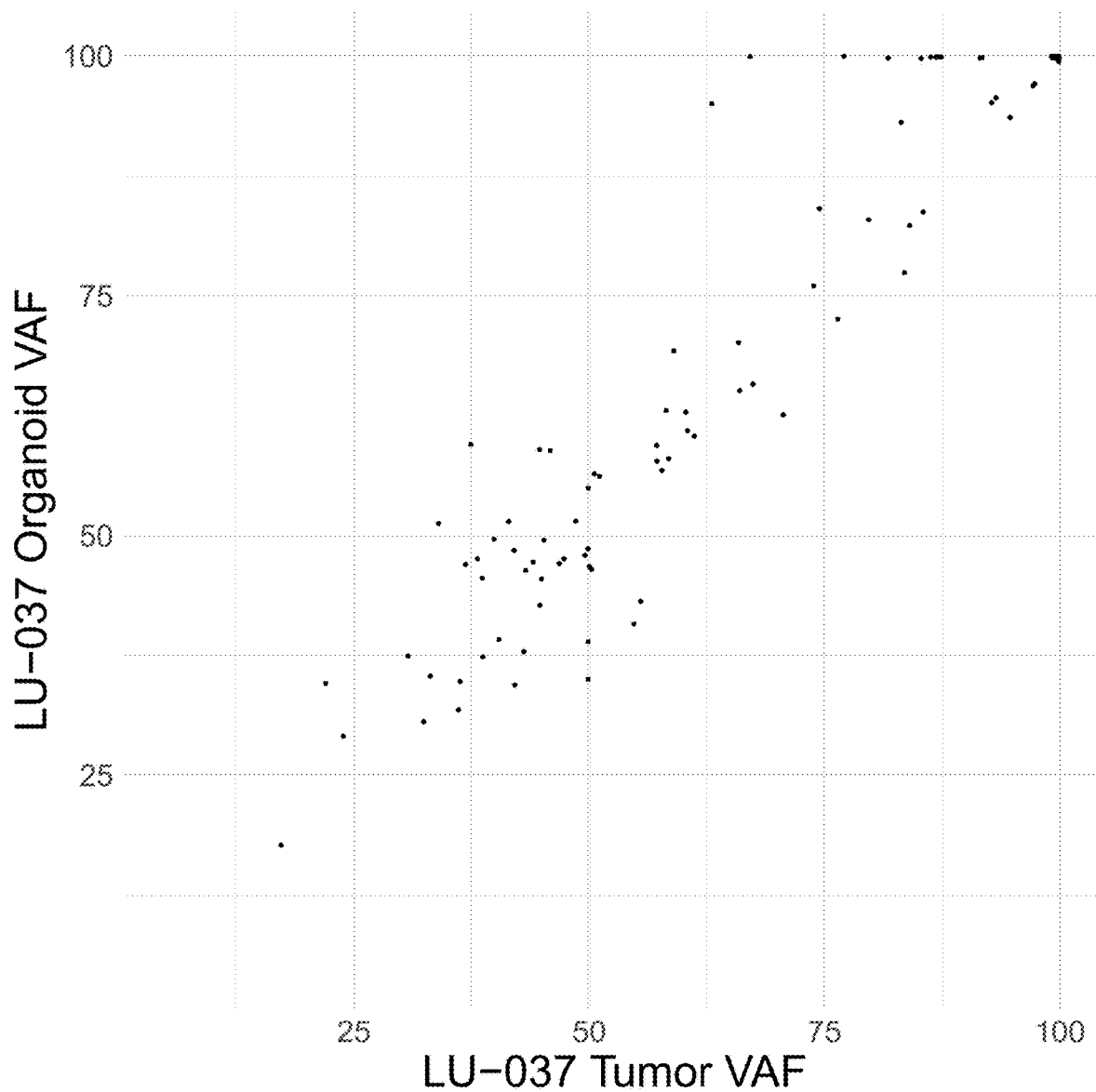
Figure 8A:
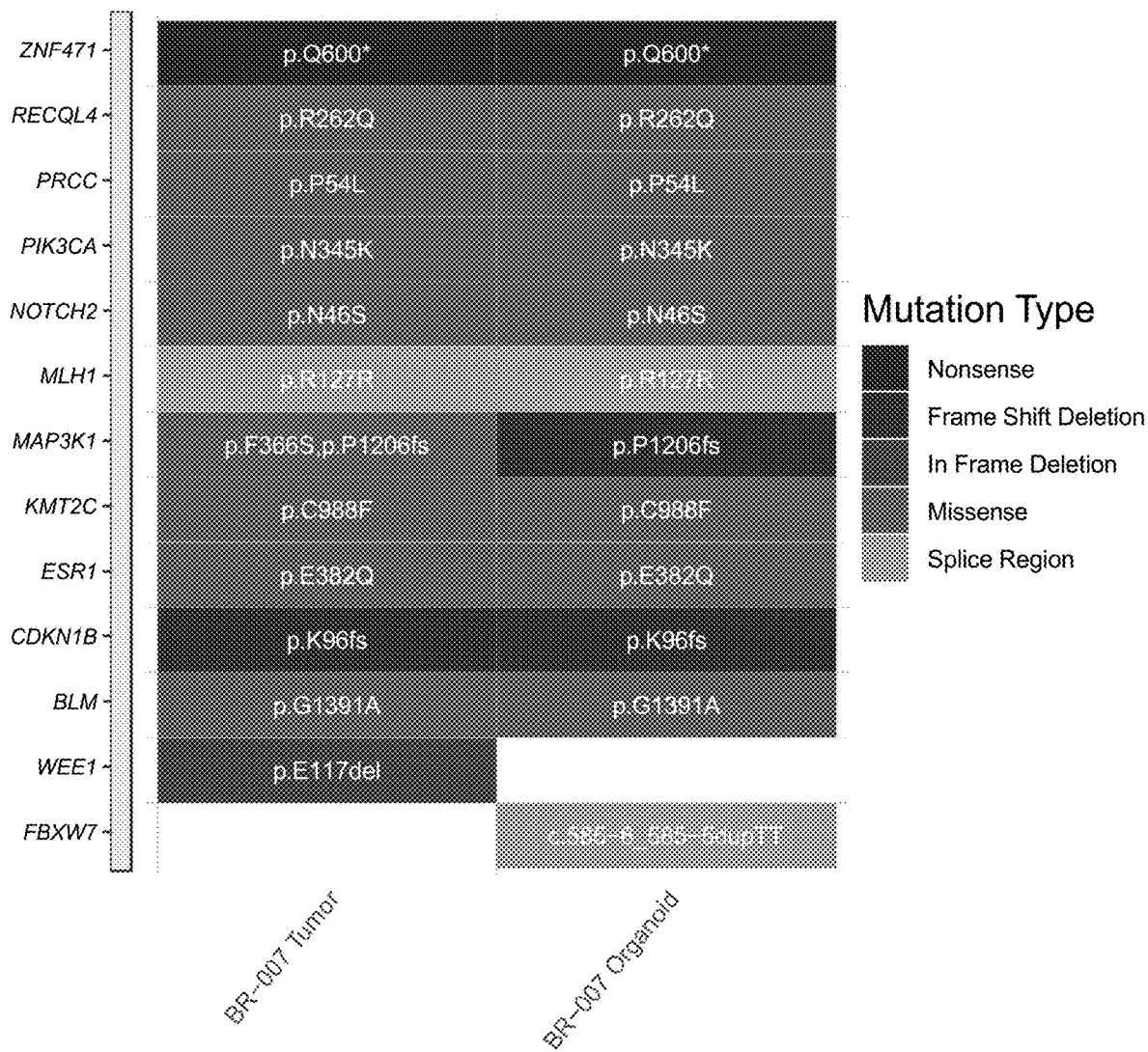
FIG. 8A, FIG. 8B, and FIG. 8C collectively show the similarity of somatic variant profiles determined from a tumor sample and a corresponding tumor organoid cell line derived from the same tumor, in accordance with some embodiments of the present disclosure. Specifically, FIG. 8A lists all of the somatic variants identified and validated from sequence reads of nucleic acids isolated from the tumor sample and the tumor organoid cell line, as well as several measures of concordance between the corresponding somatic variant profiles.
Figure 8B:
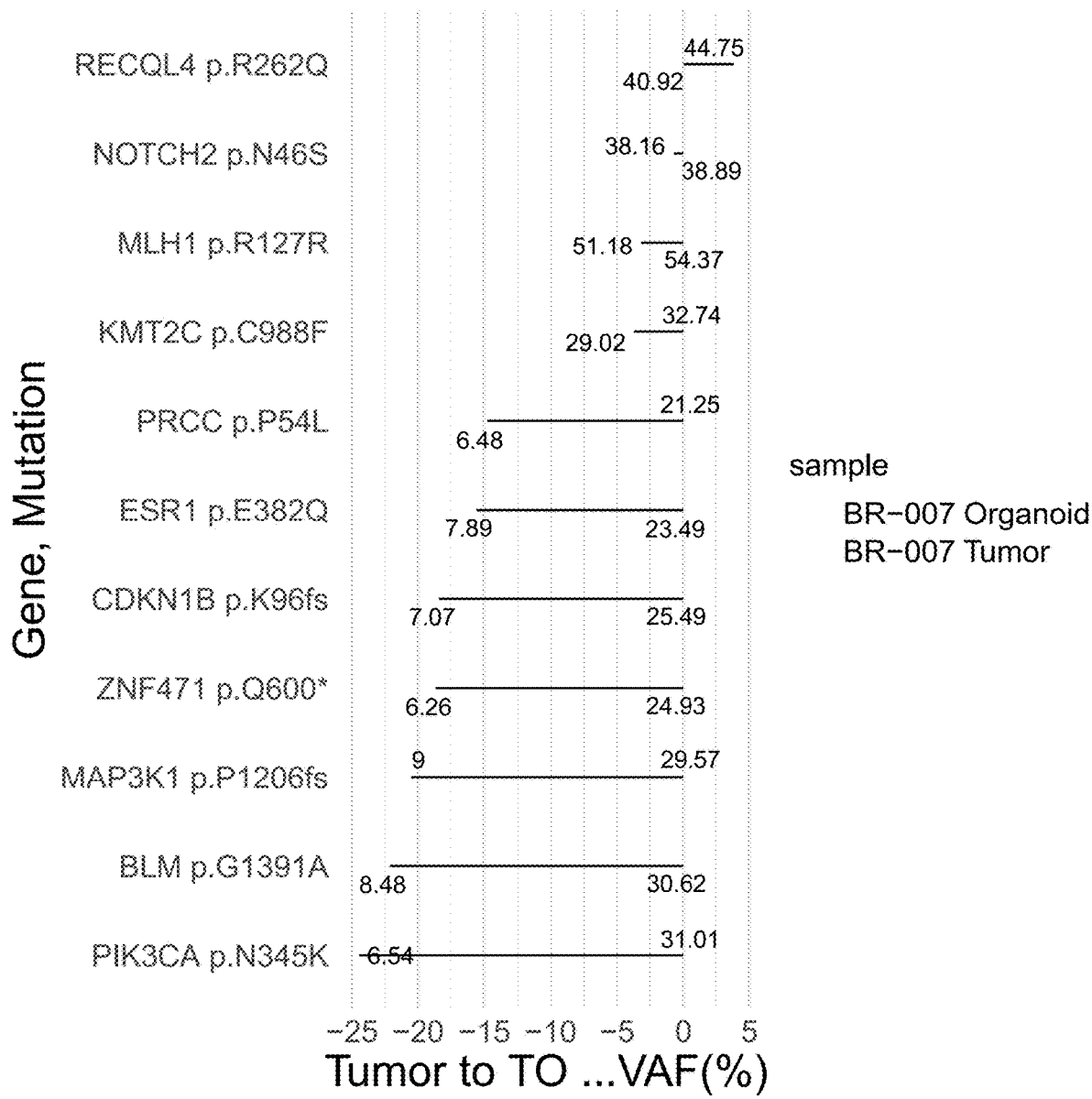
Figure 8C:
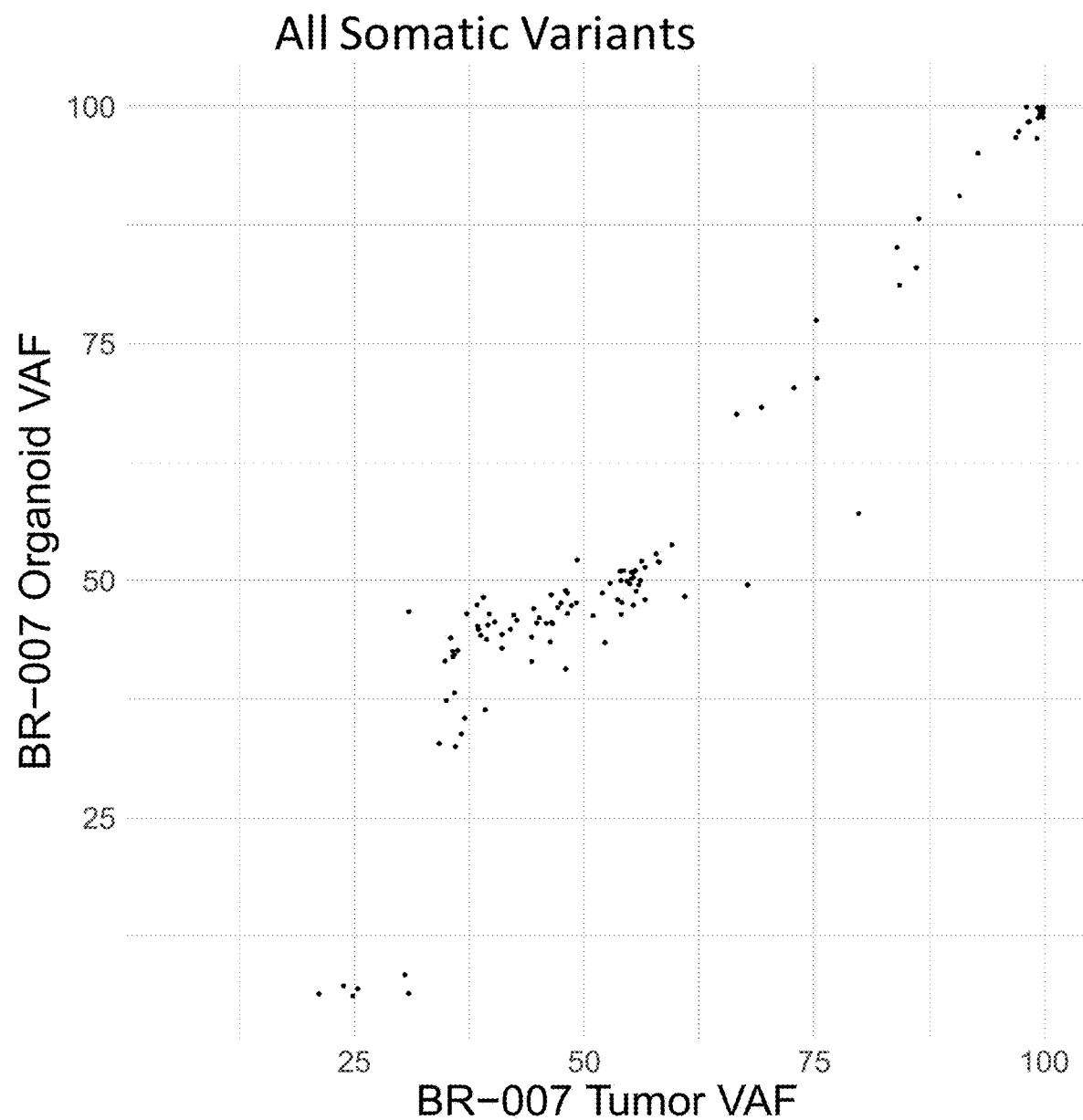
Figure 9A:
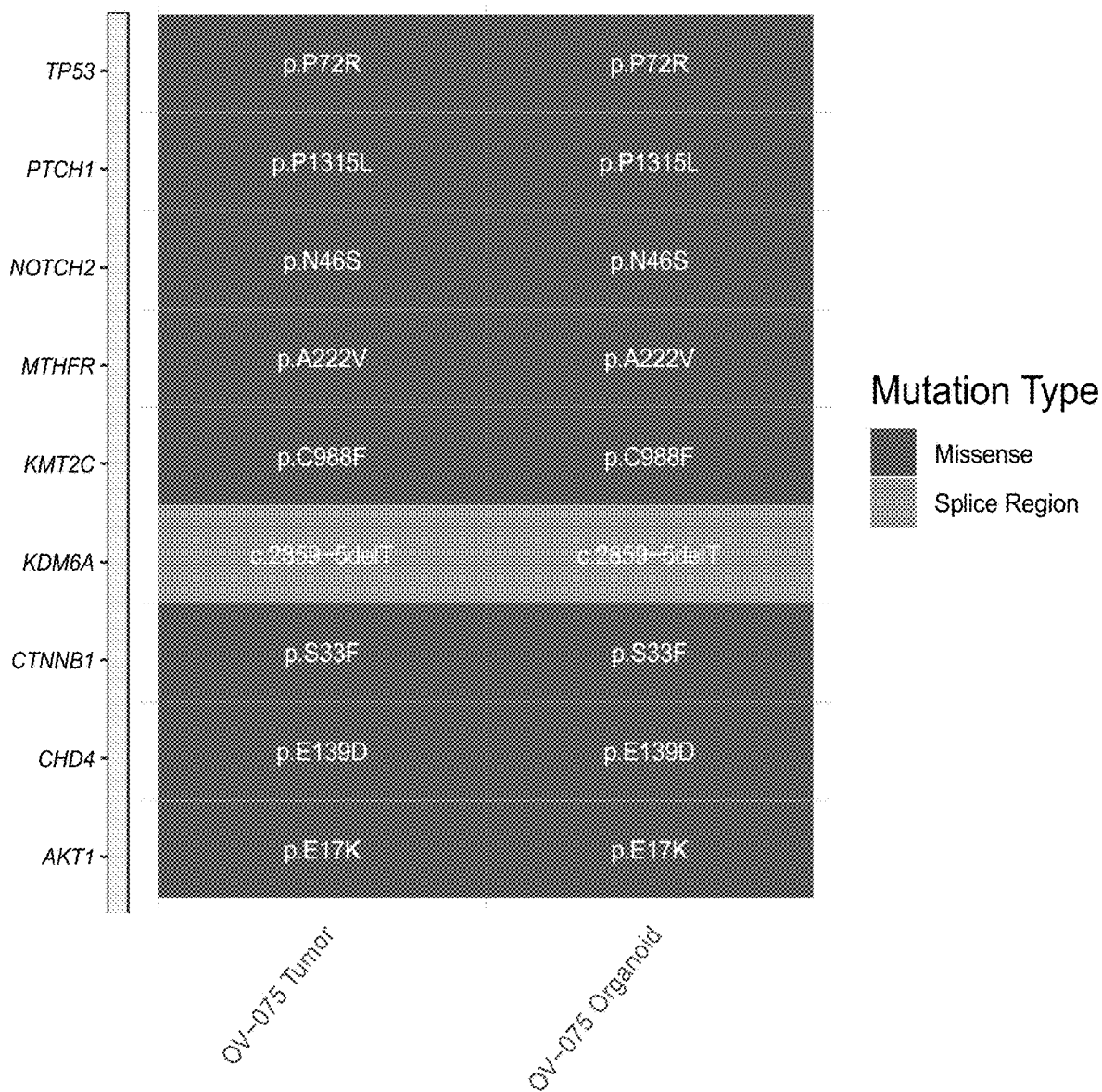
FIG. 9A, FIG. 9B, and FIG. 9C collectively show the similarity of somatic variant profiles determined from a tumor sample and a corresponding tumor organoid cell line derived from the same tumor, in accordance with some embodiments of the present disclosure. Specifically, FIG. 9A lists all of the somatic variants identified and validated from sequence reads of nucleic acids isolated from the tumor sample and the tumor organoid cell line, as well as several measures of concordance between the corresponding somatic variant profiles.
Figure 9B:
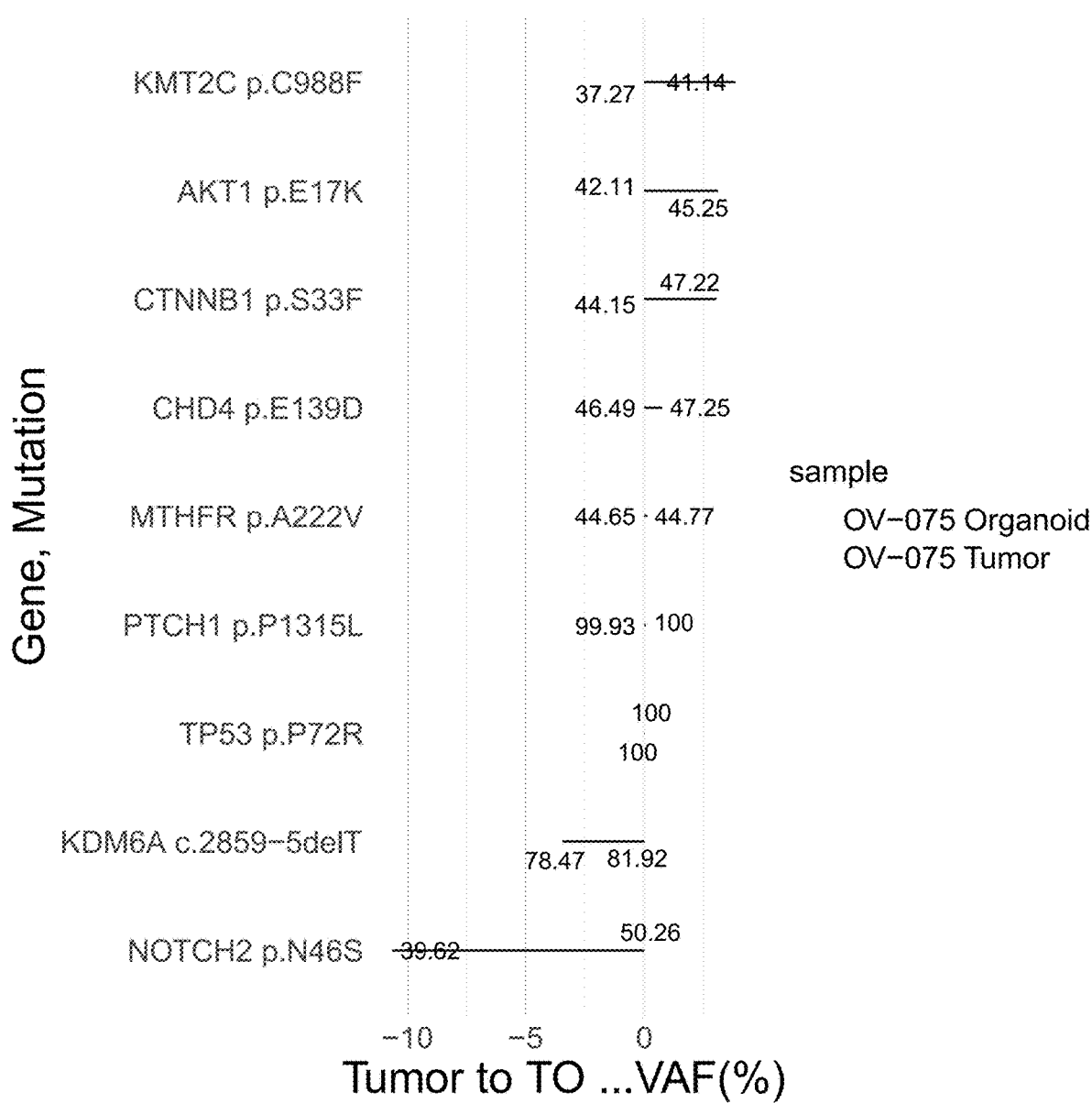
Figure 9C:
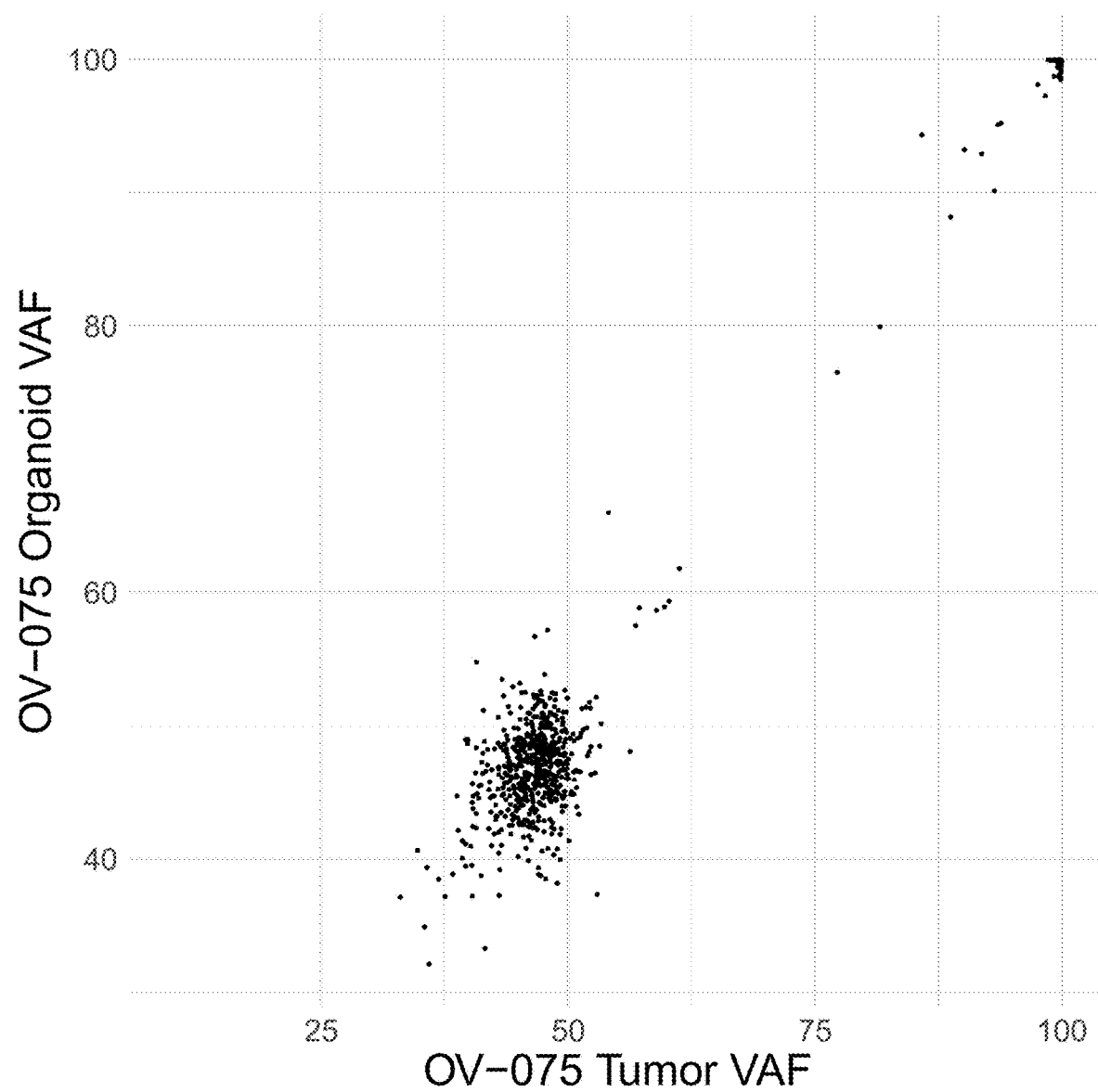

Clonal diversity was compared between tumor organoids cultured in the subject media provided herein and the source tumor from which the tumor organoids were derived, as shown in FIGS. 5-9. FIGS. 5-7 show a comparison of the clonal diversity of three different tumor organoid cell lines (CR-001, LU-025, LU-037, respectively) cultured in Type E media and the source tumors from which the lines were derived. FIGS. 5A, 6A and 7A depict somatic variants that are present in clones within both the tumor organoid cell line and respective source tumor. The somatic variants depicted are more likely to be driver mutations. Such variants, for example, are capable of altering the resultant protein encoded by the variant. As shown in FIGS. 5A, 6A and 7A, these tumor organoid cell lines exhibited concordance with their respective source tumors for such somatic variants. FIGS. 5B, 6B and 7B depict the VAFs of the somatic variants depicted in FIGS. 5A, 6A and 7A, respectively. For each of FIGS. 5B, 6B and 7B, the VAFs of the source tumor are shown in the left column and the VAFs for the tumor organoid are show in the right column. As shown in FIG. 5B for example, KMT2B p. P225 8L has a 6.2% VAF for CR-001 source tumor, meaning that 12.4% of the CR-001 tumor sample express the somatic variant. KMT2B p. P225 8L has a 8.6% VAF, meaning that 17.2% of tumor organoid cells express the somatic variant. Difference in the VAF between tumor organoid and corresponding source tumor sample can be attributed to normal specimen present in the tumor sample, which can be corrected by various methods including histologic interpretation by a pathologist, AI review, and bioinformatics estimates. A higher VAF for somatic variants in the source tumor sample compared to the corresponding tumor organoid cell line suggests using a different organoid culture medium for culturing the tumor organoid cell line. FIGS. 5C, 6C and 7C provide scatter plots of the VAFs depicted in FIGS. 5B, 6B and 7B, respectively. FIG. 8 further shows a comparison of the clonal diversity of a tumor organoid cell lines cultured in Type D media (R-spondin1-free) and the source tumor from which it was derived. As shown in FIGS. 5-7, tumor organoids cultured in Type E medium exhibit similar clonal diversity as compared to source tumors, based on concordance metrics. Further, FIG. 8 shows that a tumor organoid cell line cultured in R-spondin-free Type D media also exhibits similar clonal diversity as compared to source tumors. As such, tumor organoids that exhibit similar clonal diversity to the original tumor source can be cultured using the subject organoid culture media provided herein.

Preserving and Manipulating Clonal Populations in Organoid Cultures

Based on somatic variant signatures from sequencing, gain of function or loss of function alleles can be preserved or generated by the following environmental perturbations:

Withdrawal of specific niche factors to promote clonal proliferation of clones with downstream pathway mutations resulting in gain of function activation (e.g., withdrawal of receptor signaling ligands to promote EGFR, ERBB2, KRAS, BRAF, PIK3CA mutations).

Cytotoxicity via activation of pathways reliant on functional copies of a gene of interest. For example, TP53 mutations can be enriched for by the use of wild type p53 stabilizing agents (e.g., MDM2 antagonists).

Immune editing via co-culture of cytotoxic effector cells. For example, HLA loss can be promoted by co-culture of cytotoxic T-cells primed against antigen presentation via a specific HLA class. For example, HLA-A.2 presentation of peptides from viral onco-proteins.

Genetic engineering via exogenous nucleases (e.g., CRISPR-Cas9)

Stromal co-culture and deprivation

Xenografting of tumor culture cells into an immunodeficient animal model

For all of these manipulations, the tumor organoid cultures will be cultured in standard media types (refer to media recipe attachment).

These media types consist of a base media of a base aqueous nutrient mixture consisting of essential and non-essential amino acids, vitamins, minerals, carbohydrates, lipids, buffering agent, and electrolytes. Additional components are supplemented with B27 supplement with or without vitamin A.

Example 4: Adenoid Cystic Carcinoma (ACC)-Derived Tumor Organoid Cell Line

Tumor organoid (TO) was derived from a freshly resected tumor biopsy of a head and neck cancer of unknown origin. The tissue was later identified as ACC of the submandibular gland. Briefly, tumor tissue was dissociated using standard techniques described in Example 1. After plating in extracellular matrix, the dissociated tissue was cultured in types C, D, and E media as defined in Example 2. Upon completion of passage one, type C medium was determined to be the media type with the fewest components to support adequate growth. As such, all further passages and cryo-recovery were cultured in Type-C medium.

Eleven vials of TOs (~0.5-1×10E6 cells/vial) were cryo-preserved after seventeen days in passage three. Cell pellets were also collected for formalin-fixed paraffin embedding (FFPE) and nucleic acid extraction at that time. A diagnosis of ACC was later confirmed by in house pathological review of the hematoxylin/eosin (H & E) stained FFPE of the TO. Additionally, next generation sequencing (NGS) data from isolated TO RNA confirmed a NFIB-MYBL1 fusion—a canonical marker of ACC. Furthermore, a gene-set enrichment analysis (GSEA) was performed using TO derived RNAseq data versus two gene lists of differentially expressed genes found in Brayer et al., *Cancer Discov* 6(2):176-187 (2016), which describes the molecular characteristics of 20 ACC tumors, as shown in Table 14 below.

TABLE 14

| Gene List 1 | Gene List 2 |
|---|---|
| 'EN1', 'PRAME,' 'SOX11', 'SOX4', 'SMO','CDK4', 'POU3F2', 'CCNB1' | 'MYB', 'BMPR1B', 'PLEKHG4B', 'GABRP', 'STMN1', 'MEX3A', 'PALM2', 'ABCA13', 'MYBL1', 'ANLN', 'PIEZO2', 'CENPE', 'FAM227A', 'GPR98', 'DNAH2', 'MED12L', 'COL9A1', 'FNDC1', 'CENPF', 'NETO2', 'ST3GAL4', 'KIAA1549L', 'FABP7', 'AACSP1', 'JRKL-ASF, 'PTH2R', 'POU3F2', 'HORMAD1', 'COL2A1', 'LINC01139', 'LINC01505', 'KRT81', 'KPNA2', 'MCM2', 'ALS2CR11', 'MYO16', 'HAPLN1', 'ELAVL2', 'SOX11', 'ART3', 'FAM178B', 'PRAME, 'EN1', 'MYEOV', 'EFNA3', 'CTNND2', 'RNF212', 'ZNF727P', 'MURC, 'ADAMTS16', 'AARD', 'ZNF883', 'FAM83H-AS1', 'FSTL4', 'SLC35F3', 'MDFI', 'AADAT', 'ACTR3B', 'TMED11P', 'PPM1E', 'MLC1', 'IQGAP3', 'KIF23', 'TSIX', 'CDCA2', 'CENPH', 'MELK', 'BUB1', 'SLX4IP', 'ZNF74', 'TPX2', 'RRM2', 'DIAPH3', 'KIF14', 'FREM2', 'PCDHGB2', 'RUNX1-IT1', 'LINC00865', 'CCNB1', 'GPR137C', 'CELSR3', 'SEPT3', 'BSN' |

GSEA analysis shows strong correlation between both reported gene-lists and RU-HN-039-TO RNAseq data (rho=1.74 for the shorter gene list (gene list 1), and rho=0.74 for the longer list (gene list 2), respectively).

All references cited herein are incorporated herein by reference in their entirety and for all purposes to the same extent as if each individual publication or patent or patent application was specifically and individually indicated to be incorporated by reference in its entirety for all purposes.

Aspects of the present invention can be implemented as a computer program product that comprises a computer program mechanism embedded in a non-transitory computer readable storage medium. For instance, the computer program product could contain the program modules shown in any combination in FIGS. 1-4. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A method for culturing a tumor organoid cell line, the method comprising:
   a) obtaining a tumor sample from a subject, wherein the tumor sample is an anal cancer, a basal cell skin cancer, a squamous cancer, a breast cancer, a bladder cancer, a cervical cancer, an endometrial cancer, a head and neck cancer, a hepatobiliary cancer, a kidney cancer, a gastric cancer, a lung cancer, a mesothelial cancer of the pleural cavity, a mesothelial cancer of the peritoneal cavity, an ovarian cancer, or a prostate cancer;
   b) isolating nucleic acids from the tumor sample and sequencing a plurality of alleles for a plurality of loci of interests from the isolated nucleic acids of the tumor sample to identify a plurality of tumor sample somatic variants, wherein the sequencing is performed by next-generation sequencing;
   c) culturing the tumor organoid cell line comprising at least one tumor organoid in an organoid culture medium substantially free of R-spondins, wherein each respective tumor organoid in the tumor organoid cell line is derived from one or more cells of the tumor sample;
   d) isolating nucleic acids from the tumor organoid cell line and sequencing a plurality of alleles for a plurality of loci of interests from the isolated nucleic acids to identify a plurality of tumor organoid somatic variants, wherein the sequencing is performed by next generation sequencing;
   e) determining a reference genomic variant profile, wherein the reference genomic variant profile comprises, for each respective somatic variant in the plurality of tumor sample somatic variants identified in step b), a variant allele fraction for the respective somatic variant of the tumor sample;
   f) determining a first organoid genomic variant profile of the tumor organoid cell line, wherein the first organoid genomic variant profile comprises, for each respective somatic variant in the plurality of tumor organoid somatic variants identified in step d), a variant allele fraction for the respective somatic variant; and
   g) confirming at least a 65% concordance in the clonal diversity of the tumor organoid cell line and the tumor sample by comparing each variant allele fraction for each respective somatic variant of the tumor sample to the corresponding variant allele fraction for the corresponding somatic variant of the tumor organoid cell line, across a plurality of somatic variants found in both the reference genomic profile and the first organoid genomic variant profile.

2. The method of claim 1, wherein the tumor sample comprises biopsied material from a plurality of regions of a tumor.

3. The method of claim 1, wherein the tumor sample comprises biopsied material from a plurality of tumors from the subject.

4. The method of claim 1, further comprising evaluating a property of the tumor organoid cell line.

5. The method of claim 1, wherein the organoid culture medium comprises:
   i) a plurality of organoid growth factors, wherein the plurality of organoid growth factors consists of one of the following combinations of organoid growth factors:
      a) Noggin,
      b) a combination of EGF and Noggin, and
      c) a combination of EGF, Noggin, FGF7 and FGF10; and
   ii) a plurality of molecular inhibitors comprising a Rho kinase inhibitor, a transforming growth factor-beta inhibitor and a MAP kinase inhibitor.

6. The method of claim 1, wherein the method further comprises:
   h) exposing the tumor organoid cell line to a therapeutic agent; and
   i) after exposing the tumor organoid cell line to a therapeutic agent, evaluating a property of the exposed tumor organoid cell line.

7. The method of claim 6, wherein the evaluating in i) comprises:
   determining a second organoid genomic variant profile of the tumor organoid cell line after exposure of the tumor organoid cell line to the therapeutic agent, wherein the second organoid genomic variant profile comprises, for each respective somatic variant identified in a plurality of somatic variants identified in the tumor organoid cell line after exposure to the therapeutic agent, a relative abundance value for the respective somatic variant; and
   evaluating a difference or similarity between the first organoid genomic variant profile and the second organoid genomic variant profile.

8. The method of claim 7, wherein the second organoid genomic variant profile is determined using nucleic acids isolated from the at least one tumor organoid in the tumor organoid cell line after exposure of the tumor organoid cell line to the therapeutic agent.

9. The method of any of claims claim 7, wherein the second organoid genomic variant profile is determined using nucleic acids isolated from the organoid culture medium after exposure of the tumor organoid cell line to the therapeutic agent.

10. The method of claim 7, wherein the evaluating the difference or similarity includes determining which somatic variants experienced a threshold level of change between the first organoid genomic variant profile and the second organoid genomic variant profile.

11. The method of claim 7, wherein the method further comprises assigning a therapy to the subject based on a property of the tumor organoid cell line.

12. The method of claim 1, wherein the d) isolating nucleic acids is performed during log phase growth of the tumor organoid cell line.

13. The method of claim 1, wherein in g) the confirming is of at least a 70% concordance in the clonal diversity of the tumor organoid cell line and the tumor sample.

14. The method of claim 1, wherein in g) the confirming is of at least a 80% concordance in the clonal diversity of the tumor organoid cell line and the tumor sample.

15. The method of claim 1, wherein in g) the confirming is of at least a 90% concordance in the clonal diversity of the tumor organoid cell line and the tumor sample.

16. The method of claim 1, wherein in g) the confirming is of at least a 95% concordance in the clonal diversity of the tumor organoid cell line and the tumor sample.

17. The method of claim 1, wherein the plurality of somatic variants found in both the reference genomic profile and the first organoid genomic variant profile includes a single nucleotide variant.

18. The method of claim 1, wherein the plurality of somatic variants found in both the reference genomic profile and the first organoid genomic variant profile includes a point mutation or a nonsense mutation.

19. The method of claim 1, wherein the plurality of somatic variants found in both the reference genomic profile and the first organoid genomic variant profile includes a frame shift mutation.

20. The method of claim 1, wherein the plurality of somatic variants found in both the reference genomic profile and the first organoid genomic variant profile includes a deletion mutation, an insertion mutation, or a duplication mutation.

* * * * *